US011690831B2

(12) United States Patent
Chandraratna et al.

(10) Patent No.: US 11,690,831 B2
(45) Date of Patent: Jul. 4, 2023

(54) TREATMENT OF AUTOIMMUNE DISEASES WITH COMBINATIONS OF RXR AGONISTS AND THYROID HORMONES

(71) Applicant: IO THERAPEUTICS, INC., Houston, TX (US)

(72) Inventors: Roshantha A. Chandraratna, San Juan Capistrano, CA (US); Martin E. Sanders, Seattle, WA (US)

(73) Assignee: IO Therapeutics, Inc., Spring, TX (US)

( * ) Notice: Subject to any disclaimer, the term of this patent is extended or adjusted under 35 U.S.C. 154(b) by 0 days.

(21) Appl. No.: 17/150,646

(22) Filed: Jan. 15, 2021

(65) Prior Publication Data

US 2021/0161874 A1    Jun. 3, 2021

Related U.S. Application Data

(62) Division of application No. 16/083,799, filed as application No. PCT/US2016/059772 on Oct. 31, 2016, now Pat. No. 10,946,001.

(60) Provisional application No. 62/306,479, filed on Mar. 10, 2016.

(51) Int. Cl.
A61K 31/4418    (2006.01)
A61P 37/00    (2006.01)
A61K 9/00    (2006.01)
A61K 45/06    (2006.01)

(52) U.S. Cl.
CPC .......... A61K 31/4418 (2013.01); A61P 37/00 (2018.01); A61K 9/0043 (2013.01); A61K 9/0053 (2013.01); A61K 45/06 (2013.01)

(58) Field of Classification Search
CPC .............. A61K 31/4418; A61K 9/0043; A61K 9/0053; A61K 45/06; A61P 37/00
See application file for complete search history.

(56) References Cited

U.S. PATENT DOCUMENTS

| | | |
|---|---|---|
| 4,756,911 A | 7/1988 | Drost |
| 5,378,475 A | 1/1995 | Smith |
| 5,455,265 A | 10/1995 | Chandraratna |
| 5,466,861 A | 11/1995 | Dawson et al. |
| 5,663,367 A | 9/1997 | Vuligonda et al. |
| 5,675,033 A | 10/1997 | Vuligonda et al. |
| 5,728,846 A | 3/1998 | Vuligonda et al. |
| 5,739,338 A | 4/1998 | Beard et al. |
| 5,763,635 A | 6/1998 | Vuligonda et al. |
| 5,773,594 A | 6/1998 | Johnson et al. |
| 5,776,699 A | 7/1998 | Klein et al. |
| 5,780,647 A | 7/1998 | Vuligonda et al. |
| 5,817,836 A | 10/1998 | Vuligonda et al. |
| 5,856,490 A | 1/1999 | Teng |
| 5,877,207 A | 3/1999 | Klein et al. |
| 5,917,082 A | 6/1999 | Vuligonda et al. |
| 5,919,970 A | 7/1999 | Song et al. |
| 5,952,345 A | 9/1999 | Klein et al. |
| 5,958,954 A | 9/1999 | Klein et al. |
| 5,965,606 A | 10/1999 | Teng |
| 5,998,655 A | 12/1999 | Vuligonda et al. |
| 6,008,204 A | 12/1999 | Klein et al. |
| 6,048,873 A | 1/2000 | Vasudevan et al. |
| 6,034,242 A | 3/2000 | Vuligonda et al. |
| 6,037,488 A | 3/2000 | Song et al. |
| 6,043,381 A | 3/2000 | Vuligonda et al. |
| 6,063,768 A | 5/2000 | First |
| 6,087,505 A | 7/2000 | Vuligonda et al. |
| 6,090,810 A | 7/2000 | Klein et al. |
| 6,114,533 A | 9/2000 | Vuligonda et al. |
| 6,117,987 A | 9/2000 | Johnson et al. |
| 6,147,224 A | 11/2000 | Vuligonda et al. |
| 6,187,750 B1 | 2/2001 | Chein |
| 6,211,385 B1 | 4/2001 | Vuligonda et al. |
| 6,218,128 B1 | 4/2001 | Klein et al. |
| 6,225,494 B1 | 5/2001 | Song et al. |
| 6,228,848 B1 | 5/2001 | Klein et al. |
| 6,235,923 B1 | 5/2001 | Song et al. |
| 6,313,163 B1 | 11/2001 | Vuligonda et al. |
| 6,313,168 B1 | 11/2001 | Pacifici et al. |
| 6,387,950 B2 | 5/2002 | Nehme |
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |

(Continued)

FOREIGN PATENT DOCUMENTS

EP    2322147 A1    5/2011
EP    2556827 A1    2/2013

(Continued)

OTHER PUBLICATIONS

Van de Kerkhof and Franssen Am J Clin Dermatol 2001; 2 (3): 159-16 (Year: 2001).*
Inoue et al., Rexinoids isolated from Sophora tonkinensis with a gene expression profile distinct from the synthetic rexinoid bexarotene. J. Nat. Prod. 77:1670-1677 (2014).
"Intranasal medication delivery—brief overview of the concept." Intranasal.net. Accessed Feb. 24, 2017.
Io Therapeutics, Inc. Brochure for the Symposium on IRX4204 at The 11th International Conference on Alzheimer's and Parkinson's Diseases (2013).

(Continued)

Primary Examiner — Jeffrey S Lundgren
Assistant Examiner — William Y Lee
(74) Attorney, Agent, or Firm — K&L Gates LLP; Louis C. Cullman; Michelle Glasky Bergman

(57) ABSTRACT

The present specification provides methods of treating autoimmune diseases with a combination of a RXR agonist and a thyroid hormone.

17 Claims, 21 Drawing Sheets

(56) References Cited

U.S. PATENT DOCUMENTS

| | | |
|---|---|---|
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 10,039,731 B2 | 8/2018 | Chandraratna |
| 10,188,618 B2 | 1/2019 | Chandraratna |
| 10,590,059 B2 | 3/2020 | Chandraratna et al. |
| 10,596,133 B2 | 3/2020 | Chandraratna |
| 10,806,713 B2 | 10/2020 | Chandraratna et al. |
| 10,835,507 B2 | 11/2020 | Chandraratna et al. |
| 10,857,117 B2 | 12/2020 | Chandraratna et al. |
| 10,966,950 B2 | 4/2021 | Sanders et al. |
| 10,973,791 B2 | 4/2021 | Chandraratna et al. |
| 10,980,759 B2 | 4/2021 | Chandraratna et al. |
| 11,065,219 B2 | 7/2021 | Chandraratna et al. |
| 2001/0037025 A1 | 11/2001 | Murray |
| 2002/0156022 A1 | 10/2002 | Edwards et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0130341 A1 | 7/2003 | Li et al. |
| 2003/0144330 A1 | 7/2003 | Spiegelman |
| 2003/0219832 A1 | 11/2003 | Klein et al. |
| 2004/0005304 A1 | 1/2004 | Brudnak |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0004213 A1 | 1/2005 | Sinha et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1 | 8/2007 | Jiang |
| 2007/0265449 A1 | 11/2007 | Vuligonda et al. |
| 2009/0004291 A1 | 1/2009 | Song |
| 2009/0136470 A1 | 5/2009 | Hilde et al. |
| 2009/0203720 A1 | 8/2009 | Zhao et al. |
| 2009/0209601 A1 | 8/2009 | Nagpal et al. |
| 2009/0227674 A1 | 9/2009 | Richon et al. |
| 2010/0112079 A1 | 5/2010 | Mousa et al. |
| 2010/0298434 A1 | 11/2010 | Rouillard |
| 2011/0008437 A1 | 1/2011 | Altman |
| 2012/0115912 A1 | 5/2012 | Landreth |
| 2012/0238623 A1 | 9/2012 | Chandraratna |
| 2012/0309833 A1 | 12/2012 | Wagner et al. |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1 | 2/2015 | Chandraratna et al. |
| 2015/0196517 A1 | 7/2015 | Chandraratna et al. |
| 2015/0342917 A1 | 12/2015 | Chandraratna et al. |
| 2016/0263189 A1 | 9/2016 | Burstein |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2018/0064670 A1 | 3/2018 | Chandraratna et al. |
| 2018/0116985 A1 | 5/2018 | Chandraratna et al. |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0083441 A1 | 3/2019 | Chandraratna et al. |
| 2019/0117603 A1 | 4/2019 | Chandraratna et al. |
| 2019/0125705 A1 | 5/2019 | Chandraratna et al. |
| 2019/0201358 A1 | 7/2019 | Chandraratna et al. |
| 2019/0231726 A1 | 8/2019 | Chandraratna et al. |
| 2019/0298678 A1 | 10/2019 | Chandraratna et al. |
| 2019/0365681 A1 | 12/2019 | Chandraratna et al. |
| 2019/0381022 A1 | 12/2019 | Chandraratna et al. |
| 2020/0155488 A1 | 5/2020 | Chandraratna et al. |
| 2020/0155489 A1 | 5/2020 | Chandraratna et al. |
| 2020/0163915 A1 | 5/2020 | Chandraratna et al. |
| 2020/0170985 A1 | 6/2020 | Chandraratna et al. |
| 2020/0190008 A1 | 6/2020 | Chandraratna et al. |
| 2020/0390736 A1 | 12/2020 | Sanders et al. |
| 2021/0077445 A1 | 3/2021 | Chandraratna et al. |
| 2021/0128503 A1 | 5/2021 | Chandraratna et al. |
| 2021/0128504 A1 | 5/2021 | Chandraratna et al. |
| 2021/0205243 A1 | 7/2021 | Chandraratna et al. |
| 2022/0117922 A1 | 4/2022 | Chandraratna et al. |
| 2022/0143000 A1 | 5/2022 | Chandraratna et al. |
| 2022/0151964 A1 | 5/2022 | Chandraratna et al. |

FOREIGN PATENT DOCUMENTS

| | | |
|---|---|---|
| JP | 2010-280585 A | 12/2010 |
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/008992 A1 | 2/1999 |
| WO | 1999/033821 A1 | 7/1999 |
| WO | 1999/063980 A1 | 12/1999 |
| WO | 2000/020370 A1 | 4/2000 |
| WO | 2001/007028 A2 | 2/2001 |
| WO | 2002/089781 A2 | 11/2002 |
| WO | 2002/089842 | 11/2002 |
| WO | 2003/027090 A2 | 4/2003 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2005/013949 A2 | 2/2005 |
| WO | 2005/027895 A2 | 3/2005 |
| WO | 2007/022408 A2 | 2/2007 |
| WO | 2007/041076 A2 | 4/2007 |
| WO | 2007/041398 | 4/2007 |
| WO | 2008/157394 A2 | 12/2008 |
| WO | 2010/041149 A2 | 4/2010 |
| WO | 2010/041449 | 4/2010 |
| WO | 2010/132671 A1 | 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2015/066197 A2 | 5/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |
| WO | 2019/046591 A1 | 3/2019 |
| WO | 2019/060600 A1 | 3/2019 |

OTHER PUBLICATIONS

Jassem et al., A randomized phase III trial comparing bexarotene/cisplatin/vinorelbine versus cisplatin/vinorelbine in chemotherapy-naïve-patients with advanced or metastatic non-small cell lung cancer (NSCLC). Journal of Clinical Oncology, 2005 ASCO Annual Meeting Proceedings, vol. 23, No. 16S, Part I of II (Jun. 1 Suplement), Abstract 7024 (2005).

Johnson et al., Synthesis and biological activity of high-affinity retinoic acid receptor antagonists. Bioorganic & Medicinal Chemistry, vol. 7, No. 7, pp. 1321-1338 (1999).

Kagechika et al., Synthetic retinoids: recent developments concerning structure and clinical utility. Journal of Medicinal Chemistry, vol. 48, No. 19: 5875-5883, (2005).

(56) References Cited

OTHER PUBLICATIONS

Kawata et al., RXR partial agonist produced by side chain repositioning of alkoxy RXR full agonist retains antitype 2 diabetes activity without the adverse effects. J. Med. Chem. 58(2):912-926 (2015).
Kimura et al., IL-6: Regulator of Treg/Th 17 balance. Eur. J. Immunol., 40:1830-1835 (2010).
Kim et al., Immunopathogenesis and therapy of cutaneous T cell lymphoma. Science in Medicine, The JCI Textbook of Molecular Medicine. Editors Marks et al., p. 164 (2007).
Klein et al., Cardiovascular involvement in general medial conditions. Thyroid disease and the heart. Circulation, 116:1725-1735 (2007).
Klein et al., Identification and functional separation of retinoic acid receptor neutral antagonists and inverse agonists. The Journal of Biological Chemistry, vol. 271, No. 37, pp. 22692-22696, 1996.
Knol et al., Absence of modulation of CD4+CD25high regulatory T cells in CTCL patients treated with bexarotene. Experimental Dermatology, 19:e95-e102 (2010).
Kotani et al., A naturally occurring rexinoid, honokiol, can serve as a regulator of various retinoid X receptor heterodimers. Biol. Pharm. Bull. 35(1):1-9 (2012).
Laclair et al., Treatment with bexarotene, a compound that increases apolipoprotein-E, provides no cognitive benefit in mutant APP/PS1 mice, Molecular Neurodegeneration 8:18 (10pp) (2013).
Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).
Lefebvre et al., Retinoid X receptors: common heterodimerization partners with distinct functions. Trends Endocrinol. Metab. 21:676-683 (2010).
Levasque et al., Nur77 and retinoid X receptors: crucial factors in dopamine-related neuroadaptation. Trends in Neuroscience, vol. 30, No. 1, pp. 22-30 (2007).
Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.
Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).
Lowenthal et al., The Ethics of Early Evidence—Preparing for a Possible Breakthrough in Alzheimer's Disease, N Engl J Med., 367(6):488-490 (2012).
Macchia et al., RXR receptor agonist suppression of thryoid function: central effects in the absence of thyroid hormone receptor. Am. J. Physiol. Endocrinol. Metab., vol. 283, pp. E326-E331 (2002).
Mangelsdorf et al., Characterization of three RXR genes that mediate the action of 9-cis retinoic acid. Genes and Development 6:329-344 (1992).
Marketwire 2012: IRX4204 as a Potential Disease-Modifying Treatment for Alzheimer's Disease.
Marks et al., Science in Medicine: The JCI textbook of Molecular Medicine, p. 164 (2007).
Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).
Mcfarland et al., Low dose bexarotene treatment rescues dopamine neurons and restores behavioral function in models of Parkinson's disease. ACS Chem. Neurosci. 4:1430-1438 (2013).
Migliore, Intranasal Delivery of GDNF for the Treatment of Parkinson's Disease. Doctoral Thesis, Pharmaceutical Sciences, Northeastern University, Boston, MA (2008).
Miller et al., Initial clinical trial of a selective retinoid X receptor ligand, LGD1069. J Clin Oncol., 15(2):790-795 (1997).
Monahan et al., Neuroinflammation and peripheral immune infiltration in Parkinson's disease: an autoimmune hypothesis. Cell Transplant, 17:363-372 (2008).
Morris & Burns, Insulin: An Emerging Treatment for Alzheimer's Disease Dementia? Curr. Neurol. Neurosci. Rep. 12(5):520-527 (2012).
Munhoz et al., Parkinson's disease and thyroid dysfunction. Parkinsonism & Related Disorders, 10(6):381-383 (2004).
National Multiple Sclerosis Society, Medications, accessed May 12, 2017, pp. 1-5.
Natrajan et al., Retinoid X receptor activation reverses age-related deficiencies in myelin debris phagocytosis and remyelination. Brain A Journal of Neurology, 138:3581-3597 (2015).
Nishimaki-Mogami et al., The RXR agonists PA024 and HX630 have different abilities to activate LXR/RXR and to induce ABCA1 expression in macrophage cell lines. Biochemical Pharmacology, 76: 1006-1013 (2008).
Ohsawa et al., Modification of the lipophilic domain of RXR agonists differentially influences activation of RXR heterodimers. ACS Med Chem Lett., 1:521-525 (2010).
Olson et al., Immunomodulation as a neuroprotective and therapeutic strategy for Parkinson's disease. Curr Opin Pharmacol. 26:87-95 (2016).
Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).
Perlmann et al., A novel pathway for vitamin A signaling mediated by RXR heterodimerization with NGFI-B and NURR1. Genes & Develop. 9:769-782 (1995).
Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (Jun. 1 Supplement) Abstract 7243 (2005).
Pierrot et al., Targretin Improves Cognitive and Biological Markers in a Patient with Alzheimer's Disease. Journal of Alzheimer's Disease, 49:271-276 (2016).
Price et al., Comment on ApoE-directed Therapeutics Rapidly Clear beta-Amyloid and Reverse Deficits in AD Mouse Models. Science 340:924-d (2013).
Ramaswamy et al., Trophic factors therapy in Parkinson's disease. Prog. Brain Res., 175:201-216 (2009).
Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: Spirit I. J. Clin. Oncol., 26:1886-1892 (2008).
Reynolds et al., Regulatory T cells attenuate Th17 cell-mediated nigrostriatal dopaminergic neurodegeneration in a model of Parkinson's disease. J. Immunol., vol. 184, pp. 2261-2271 (2010).
Riancho et al., Neuroprotective effect of bexarotene in SOD1G93A mouse model of amyotrophic lateral sclerosis. Frontiers in Cellular Neuroscience 9:Article 250 (2015).
Rigas et al., Emerging role of rexinoids in non-small cell lung cancer: Focus on bexarotene. The Oncologist, 10:22-33 (2005).
Rizvi et al., A phase I study of LGD1069 in adults with advanced cancer. Clin. Cancer Res., 5:1658-1664 (1999).
Sacchetti et al., Requirements for heterodimerization between orphan nuclear receptor Nurr1 and Retinoid X Receptors. The Journal of Biological Chemistry, 277(38):35088-35096 (2002).
Salama et al., Role of L-thyroxin in counteracting rotenone induced neurotoxocity in rats. Environmental Toxicology and Pharmacology, 35:270-277 (2013).
Sherman et al., Central hypothyroidism associated with retinoid X receptor-selective ligands. The New England Journal of Medicine, vol. 340, No. 14, pp. 1075-1079 (1999).
Aranami et al., Th17 cells and autoimmune encephalomyelitis (EAE/MS). Allergology International, 57:115-120 (2008).
Certo et al., Activation of RXXR/PPARγ underlies neuroprotection by bexarotene in ischemic stroke. Pharm. Resc. 102:298-307 (2015).

(56) References Cited

OTHER PUBLICATIONS

Chinese Office Action, dated May 21, 2020, for Chinese Patent Application No. 201680083364.8 (original and translation included).
Extended European Search Report for EP 16861057, dated Jul. 6, 2019.
Graeppi-Dulac et al., Endocrine Side-Effects of Anti-Cancer Drugs: The impact of retinoids on the thryoid axis. European Journal of Endocrinology, 170(6), R253-R262 (2014).
Lalloyer et al., Rexinoid bexarotene modulates triglyceride but not cholesterol metabolism in the liver. Arterioscler Thromb Vasc Biol 29(10):1488-1495 (2009).
Liby et al., A new rexinoid, NXR194204, prevents carcinogenesis in both the lung and mammary gland. Clin Cancer Res, 13(20):6237-6243 (2007).
Mor et al., Autoimmune encephalomyelitis and uveitis induced by T cell immunity to self beta-synuclein. The Journal of Immunology, 170:628-634 (2003).
Reagan-Shaw et al., Dose translation from animal to human studies revisted. FASEB J, 22:659-661 (2007).
U.S. Appl. No. 16/898,230, filed Jun. 10, 2020.
U.S. Appl. No. 17/064,969, filed Oct. 7, 2020.
U.S. Appl. No. 17/126,714, filed Dec. 18, 2020.
U.S. Appl. No. 17/126,787, filed Dec. 18, 2020.
Waite et al., Review Article: Th17 response and inflammatory autoimmune diseaes. International Journal of Inflammation, vol. 2012, Article ID 819467, 10 pp (2011).
Wikipedia, Experimental autoimmune encephalomyelitis, https://en.wikipedia.org/wiki/Experimental_autoimmune_encephalomyelitis, accessed Jul. 1, 2019 (last edited on Feb. 10, 2019).
Zhao et al., Application of thyroid hormone in animal models of multiple sclerosis. Drug Evaluation Research, 39(1):148-151 (2016).
Andreaone et al., Cerebral atrophy and white matter disruption in chronic schizophrenia. EUR Arch Psychiatry Clin Neurol 257:3-11 (Feb. 2007).
Andreaone et al., Cortical white-matter microstructure in schizophrenia. British J Psychiatry 191:113-119 (Aug. 2007).
Banati et al., Inflammatory reaction in experimental autoimmune encephalomyelitis (EAE) is accompanied by a microglial expression of the betaA4-amyloid precursor protein (APP). Gila 14:209-215 (1995).
Becher et al., Th17 cytokines in autoimmune neuro-inflammation. Curr Opin Immunol 23(6):707-712 (2011).
Bettelli et al., Induction and effector functions of Th17 cells. Nature 453(7198):1051-1057 (2008).
Chandraratna et al., Treatment with retinoid X receptor agonist IRX4204 ameliorates experimental autoimmune encephalomyelitis. Am J Transl Res 8(2):1016-1026 (2016).
Davis et al., White matter changes in schizoprenia—Evidence for myelin-related dysfunction. Arch Gen Psychiatry 60:443-456 (2003).
Debnath & Berk, Functional implications of the IL-23/IL-17 immune axis in schizophrenia. Mol Neurobiol, 54:8170-8178 (2017).
Ding et al., Activation of Th17 cells in drug naive, first episode schizophrenia. Progress in Neuro-Pyschopharmacology & Biological Psychiatry, 51:78-82 (2014).
Domingues et al., Functional and pathogenic differences of Th1 and Th17 cells in experimental autoimmune encephalomyelitis. PLOS One, 5(11):e15531 (2010).
Drexhage et al., An activated set point of T-cell monocyte inflammatory networks in recent-onset schizophrenia patients involves both pro- and anti-inflammatory forces. International Journal of Neuropsychopharmacology, 14:746-755 (2011).
Flygt et al., Myelin loss and oligodendrocyte pathology in white matter tracts following traumatic brain injury in the rat. European Journal of Neuroscience 38:2153-2165 (2013).
Flynn et al., Abnormalities of myelination in schizophrenia detected in vivo with MRI, and post-mortem with analysis of oligodendrocyte proteins. Molecular Psychiatry, 8:811-820 (2003).
Gilgun-Sherki et al., Riluzole suppresses experimental autoimmune encephalomyelitis: implications for the treatment of multiple sclerosis. Brain Research, 989:196-201 (2003).

Haqqani et al., Intercellular interactomics of human brain endothelial cells and Th17 lymphocytes: a novel strategy for identifying therapeutic targets of CNS inflammation. Cardiovascular Psychiatry and Neurology 2011: ID175364 (2011).
Inglese et al., Therapeutic strategies in multiple sclerosis: A focus on neuroprotection and repair and relevance to schizophrenia. Schizophrenia Research, 161:94-101 (2015).
Johnson et al., Axonal pathology in traumatic brain injury. Exp Nuerol, 246:35-43 (2013).
Kebir et al., Human Th17 lymphocytes promote blood-brain barrier disruption and central nervous system inflammation. Nat Med 13(10):1173-1175 (2007).
Komiyama et al., IL-17 plays an important role in the development of experimental autoimmune encephalomyelitis. J. Immunol., 177:566-573 (2006).
Koster et al., Emerging drugs for schizophrenia: an update. Expert Opin Emerging Drugs, 19(4):511-531 (2014).
Li et al., Plasma levels of Th17-related cytokines and complement C3 correlated with aggressive behavior in patients with schizophrenia Psychiatry Research, 246:700-706 (2016).
Mai et al., T helper 17 cells interplay with CD4+CD25highFoxp3+ Tregs in regulation of inflammations and autoimmune diseases. Front Biosci, 15:986-1006 (2010).
Miller et al., Meta-analysis of cytokine alterations in schizophrenia: Clinical status and antipsychotic effects. Biol Psychiatry, 70(7):663-671 (2011).
Miller et al., Meta-analysis of lymphocytes in schizophrenia: Clinical status and antipsychotic effects. Biol Psychiatry, 73(10):993-999 (2013).
Moriya et al., Edaravone, a free radical scavenger, ameliorates experimental autoimmune encephalomyelitis. Neuroscience Letters, 440:323-326, 2008.
Murphy et al., Infiltration of Th1 and Th17 cells and activation of microglia in the CNS during the course of experimental autoimmune encephalomyelitis. Brain Behavior and Immunity, 24:641-651 (2010).
Pastemak et al., The extent of diffusion MRI markers of neuroinflammation and white matter deterioration in chronic schizophrenia. Schizophrenia Research, 161(1):113-118 (2015).
Rostami et al., Role of Th17 cells in the pathogenesis of CNS inflammatory demyelination. J. Neurol Sci, 330:76-87 (2013).
Saresella et al., T helper-17 activation dominates the immunologic milieu of both amyotrophic lateral sclerosis and progressive multiple sclerosis. Clincal Immunology, 148:79-88 (2013).
Schneider et al., Hyperphosphorylation and aggregation of Tau in experimental autoimmune encephalomyelitis. J Biol Chem 279(53):55833-55839 (2004).
Segal, Th17 cells in autoimmune demyelinating disease. Semin Immunopathol, 32(1):71-77 (2010).
Smith, A comprehensive macrophage-T-lymphocyte theory of schizophrenia. Medical Hypotheses, 39:248-257 (1992).
Stromnes et al., Differential regulation of central nervous system autoimmunity by TH1 and TH17 cells. Nat Med, 14(3):337-342 (2008).
Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Suh et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).

(56) References Cited

OTHER PUBLICATIONS

Tesseur et al., Comment on ApoE-directed Therapeutics Rapidly Clear beta-Amyloid and Reverse Deficits in AD Mouse Models. Science, 340:924-e (2013).
Tovar-y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
Assaf et al., Minimizing adverse side-effects of oral bexarotene in cutaneous T-cell lymphoma: an expert opinion. British Journal of Dermatology, 155, pp. 261-266 (2006).
Diab et al., Ligands for the peroxisome proliferator-activated receptor-gamma and the retinoid X receptor exert additive anti-inflammatory effects on experimental autoimmune encephalomyelitis. Journal of Neuroimmunology, 148, pp. 116-126 (2004).
Extended European Search Report, dated Oct. 1, 2019, for European Application No. 16893789.4 filed Oct. 31, 2016.
Farmer et al., Retinoic acid receptor ligands based on the 6-cyclopropyl-2,4-hexadienoic acid. Bioorganic & Medicinal Chemistry Letters, 13:261-264 (2003).
Hsu et al., Generation and characterization of monoclonal antibodies directed against the surface antigens of cervical cancer cells. Hybrid Hybridomics, vol. 23, No. 2, pp. 121-125 (2004)—abstract.
Uslu et al., Doxazosin: a new cytotoxic agent for prostate cancer? BJU International, vol. 85, pp. 672-675 (2000).
Veeraraghavalu et al., Comment on ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci., 35(42):14370-14385 (2015).
Walkley et al., Retinoic acid receptor anatagonism in vivo expands the numbers of precursor cells during granulopoiesis. Leukemia, vol. 16, No. 9, pp. 1763-1772 (2002).
Wallen-Mackenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7(7):7469-7479 (2016).
Wang, (2013) Slide presentation at the Symposium on IRX4204 at The 11th International Conference on Alzheimer's and Parkinson's Diseases: The Novel RXR agonist IRX4204 as a Potential Disease-Modifying Agent in Alzheimer's Disease.
WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181: 2277-2284 (2008).
Xiao et al., Adenomatous polyposis coli (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive effects on dendritic cells by RXR-dependent activation: inhibition of peroxisome proliferator-activated receptor gamma blocks some of the 9cRA activities, and precludes them to mature phenotype development The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).

Jones et al., Animal models of schizophrenia. British Journal of Pharmacology, 164:1162-1194 (2011).
Kabbinavar et al., An open-label phase II clinical trial of the RXR agonist IRX4204 in taxane-resistant, castration-resistant metastatic prostate cancer (CRPC). Journal of Clinical Oncology, vol. 32, No. 15 Suppl, p. 5073 (2014).
Kim, Chang H. Regulation of FoxP3+ regulatory T cells and Th17 cells by retinoids. Clinical and Developmental Immunology, vol. 2008, 12 pages (2008).
Koivusalo et al., The cytotoxicity of chemotherapy drugs varies in cervical cancer cells depending on the p53 status. Cancer Biology and Therapy, vol. 3278(11):1177-1183 (2004).
Liu et al., Mechanism of selective retinoid X receptor agonist-induced hypothroidism in the rat. Endocrinology, 143(8):2880-2885 (2002).
Singaporean Written Opinion, dated Sep. 26, 2019, for Singaporean Application No. 11201807250P filed on Oct. 31, 2016.
Singaporean Written Opinion, dated Sep. 16, 2019, for Singaporean Application No. 11201807255Y filed on Oct. 31, 2016.
Supplementary European Search Report for European Patent Application No. 16861057 dated May 22, 2019.
Supplementary European Search Report for European Patent Application No. 16861059 dated May 16, 2019.
Vuligonda et al., Enantioselective syntheses of potent retinoid X receptor ligands: Differential biological activities of individual antipodes. J. Med. Chem., 44. pp. 2298 2303 (2001).
Trapp et al., Axonal transection in the lesions of multiple sclerosis. N Engl J Med 338:278-785 (1998).
Wikipedia, Schizophrenia, https://www.nimh.nih.gov/health/statistics/schizophrenia.html, accessed Feb. 20, 2020.
Bendele, Animal models of rheumatoid arthritis. J Musculoskel Neuron Interact, 1(4):377-385 (2001).
Harris, Retinoid therapy for rheumatoid arthritis. Annals of Internal Medicine, vol. 100(1), pp. 146-147 (1984).
Mucida et al., Supplemental Online Material: Reciprocal Th-17 and regulatory T cell differentiation mediated by retinoic acid. Retrieved on Mar. 5, 2021. Retrieved from internet, url:www.sciencemag.org/cgi/conent/full/1145697/DC1>(Year:2007).
Mucida et al., Reciprocal Th-17 and regulatory T cell differentiation mediated by retinoic acid. Science, vol. 317 (5835), pp. 256-260 (2007).
Science Daily [online] (2007), Potential role for retinoic acid in autoimmune and inflammatory diseases identified, La Jolla Institute for Allergy and Immunology p. 1-3 Retrieved from the internet, Retrieved on Mar. 5, 2021, <url:www.sciencedaily.com/releases/2007/06/070614151809.htm> (Year:2007).
Alcala-Barraza et al., Intranasal delivery of neurotrophic factors BDNF, CNTF, EPO, and NT-4 to the CNS. Journal of Drug Targeting, 18(3):179-190 (2009).
Altucci L et al., RAR and RXR modulation in cancer and metabolic disease. Nature Review Drug Discovery, vol. 6: 793-810 (2007).
Alzforum 2013: Can Cancer Therapy Be Neurodegenerative Wonder Drug?
Annerbo et al., Review Article: A clinical review of the association of thyroid stimulating hormone and cognitive impairment. ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).
Bilbao et al., Insulin-like growth factor-1 stimulates regulatory T cells and suppresses autoimmune disease. EMBO Mol. Med., 6(11):1423-1435 (2014).
Blumenschein et al., A randomized phase III trial comparing bexarotene/carboplatin/paclitaxel versus carboplatin/paclitaxel in chemotherapy-naive patients with advanced or metastatic non-small cell lung

(56) References Cited

OTHER PUBLICATIONS cancer (NSCLC). Journal of Clinical Oncology, 2005 ASCO Annual Meeting Proceedings, vol. 23, No. 16S, Part I of II, Abstract 7001 (2005).

Bordoni et al., Bexarotene improves TTP in untreated, advanced NSCLC, when given in combination with carboplalin/paclitaxel. Journal of Clinical Oncology, ASCO 2005 Annual Meeting, Abstract 7270.

Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).

Cal et al., Doxazosin: a new cytotoxic agent for prostate cancer? BJU Int. 85:672-675 (2000).

Calza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).

Coya et al., Retinoic Acid Inhibits In Vivo Thyroid-Stimulating Hormone Secretion, Life Sciences, Pharmacology Letters, 60:247-50, 1997.

Cramer et al., ApoE-directed therapeutics rapidly clear β-amyloid and reverse deficits in AD mouse models. Science, 335(6075): 1503-1506 (2012).

Crowe et al., A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).

Cummings et al., Double-blind, placebo-controlled, proof-of-concept trial of bexarotene Xin moderate Alzheimer's disease. Alzheimer's Research & Therapy, 8:4 (2016).

Debnath & Berk, Th17 Pathway-Mediated Immunopathogenesis of Schizophrenia: Mechanisms and Implications. Schizophrenia Bulletin, 40(6):1412-1421 (2014).

Dell'Acqua ML et al., Functional and molecular evidence of myelin- and neuroprotection by thyroid hormone administration in experimental allergic encephalomyelitis. Neuropath. Appl. Neurobiol., 38:454-470 (2012).

D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).

Dore et al., Insulin-like growth factor I protects and rescues hippocampal neurons against beta-amyloid- and human amylin-induced toxicity. Proc. Natl. Acad. Sci. USA, 94:4772-4777 (1997).

Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.

Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).

Elias et al., Retinoic acid inhibits TH17 polarization and enhances FoxP3 expression through a Stat-3/Stat-5 independent signaling pathway. Blood, vol. 111, No. 3, pp. 1013-1020 (2008).

Fitz et al., Comment on ApoE-directed Therapeutics Rapidly Clear beta-Amyloid and Reverse Deficits in AD Mouse Models. Science 340:924-c (2013).

Franco et al., Thyroid hormones promote differentiation of oligodendrocyte progenitor cells and improve remyelination after cuprizone-induced demyelination. Experimental Neurology, 212, pp. 458-467, 2008 (2008).

Freiherr et al., Intranasal Insulin as a Treatment for Alzheimer's Disease: A Review of Basic Research and Clinical Evidence. CNS Drugs 27:505-514 (2013).

Friling et al., Activation of retinoid X receptor increases dopamine cell survival in models for Parkinson's disease. BMC Neuroscience, 10: 146 (2009).

Fu et al., Thyroid hormone prevents cognitive deficit in a mouse model of Alzheimer's disease. Neuropharmacology, 58:722-729 (2010).

Gibb et al., The substantia nigra and ventral tegmental area in Alzheimer's disease and Down's sydrome. J. Neurol. Neurosurg. and Psychiatry, 52:193-200 (1989).

Golub et al., Molecular classification of cancer: Class discovery and class prediction by gene expression monitoring. Science, vol. 286, Oct. 15, 1999, pp. 531-537.

Gonzalez et al., T-cell-mediated regulation of neuroinflammation involved in neurodegenerative diseases. J Neuroinflam 11:201-212 (2014).

Govindan et al., Phase II trial of bexarotene capsules in patients with non-small-cell lung cancer (NSCLC) who have failed at least 2 prior systemic therapies for Stage IIIB/IV disease. Journal of Clinical Oncology, 2005 ASCO Annual Meeting Proceedings, vol. 23, No. 16S, Part I of II, Abstract 7116 (2005).

Graber et al., Protective autoimmunity in the nervous system. Pharmacol. Therapeut., 121:147-159 (2009).

Haugen et al., The Thyrotrope-Restricted Isoform of the Retinoid-X Receptor-y1 Mediates 9-cis-Retinoic Acid Suppression of Thyrotropin-beta Promoter Activity. Molecular Endocrinology 11:481-9, 1997.

Henkel et al., Regulatory T-lymphocytes mediate amyotrophic lateral sclerosis progression and survival. EMBO Mol. Med., 5:64-79 (2012).

Hu et al., Imbalance between IL-17A-Producing Cells and Regulatory T Cells during Ischemic Stroke. Mediators of Inflammation 2014: Article ID 813045, 2014.

Huang et al., Retinoid X receptor gamma signaling accelerates CNS remyelination, Nature Neuroscience, 14(1):45-53, 2011 (Epub Dec. 5, 2010).

International Search Report and Written Opinion dated Mar. 28, 2013 for International Application Serial No. PCT/US2012/069566 filed on Dec. 13, 2012.

International Search Report and Written Opinion dated Jan. 5, 2017 for International Application Serial No. PCT/US2016/059770 filed Oct. 31, 2016.

International Search Report for PCT/US2007/011730 dated May 2, 2008.

International Search Report and Written Opinion dated Sep. 25, 2007 for International Application No. PCT/US2006/038252 filed on Oct. 2, 2006.

International Search Report and Written Opinion dated Dec. 29, 2016 for International Application No. PCT/US2016/059775 filed on Oct. 31, 2016.

International Search Report and Written Opinion dated Jan. 10, 2017 for International Application No. PCT/US2016/059776 filed on Oct. 31, 2016.

International Search Report and Written Opinion dated Dec. 29, 2016 for International Application No. PCT/US2016/059779 filed on Oct. 31, 2016.

International Search Report and Written Opinion dated May 22, 2017 for International Application No. PCT/US2016/059772 filed on Oct. 31, 2016.

International Search Report and Written Opinion dated Jan. 18, 2019 for International Application No. PCT/US2018/052031 filed on Sep. 20, 2018.

International Search Report and Written Opinion dated Dec. 11, 2018 for International Application No. PCT/US2018/048876 filed on Aug. 30, 2018.

Alsudais et al., Retinoid X receptor-selective signaling in the regulation of Akt/protein kinase B isoform-specific expression. The Journal of Biological Chemistry, vol. 291, No. 6, pp. 3090-3099 (2015).

Rittenhouse et al., Thyroxine administration prevents streptococcal cell wall-induced inflammatory responses. Endocrinology, 138(4):1434-1439 (1997).

Singaporean Written Opinion, dated Apr. 22, 2021, for Singaporean Application No. 11201807255Y filed on Oct. 31, 2016.

(56) References Cited

OTHER PUBLICATIONS

Hueber et al., Effects of AIN457, a fully human antibody to interleukin-17A, on psoriasis, rheumatoid arthritis, and uveitis. Science Translational Medicine, vol. 2, Issue 52, 52ra72 (2010).

Sugiyama et al., Dysfunctional blood and target tissue CD4+ CD25high regulatory T cells in psoriasis: Mechanism underlying unrestrained pathogenic effector T cell proliferation. J. Immunol, 174:164-173 (2005).

Yin et al. (2014) PLoS One 9(4): e93960. doi:10.1371/joural.pone.0093960.

Castillo Al, et al. "A permissive retinoid X receptor/thyroid hormone receptor heterodimer allows stimulation of prolactin gene transcription by thyroid hormone and 9-cis-retinoid acid" Mol Cell Biol 24:502-513, 2004.

Kliewer SA, et al. "Retinoid X receptor interacts with nuclear receptors in retinoic acid, thyroid hormone and vitamin D3 signaling" Nature 355:446-449, 1992.

Li D, et al. "Functional evidence for retinoid X receptor (RXR) as a nonsilent partner in the thyroid hormone receptor/RXR heterodimer" Mol Cell Biol 22:5782-5792, 2002.

Yin et al. (2014) PLoS One 9(4): e93960. doi:10.1371/journal.pone.0093960.

\* cited by examiner

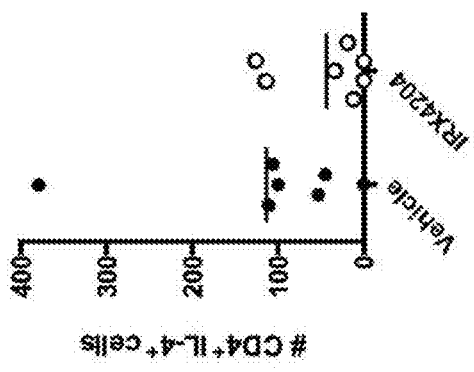
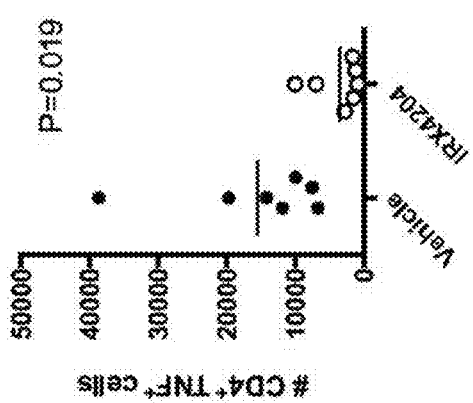
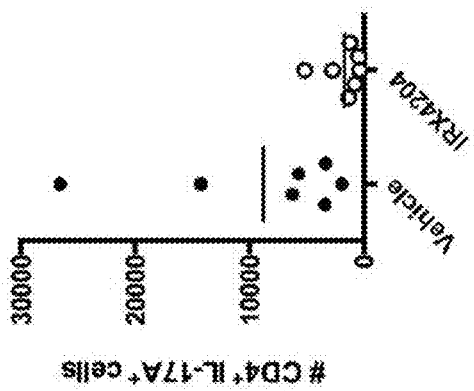
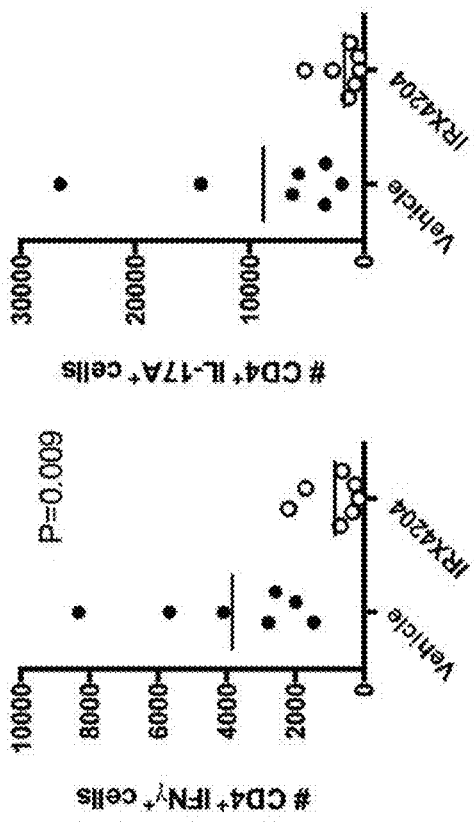

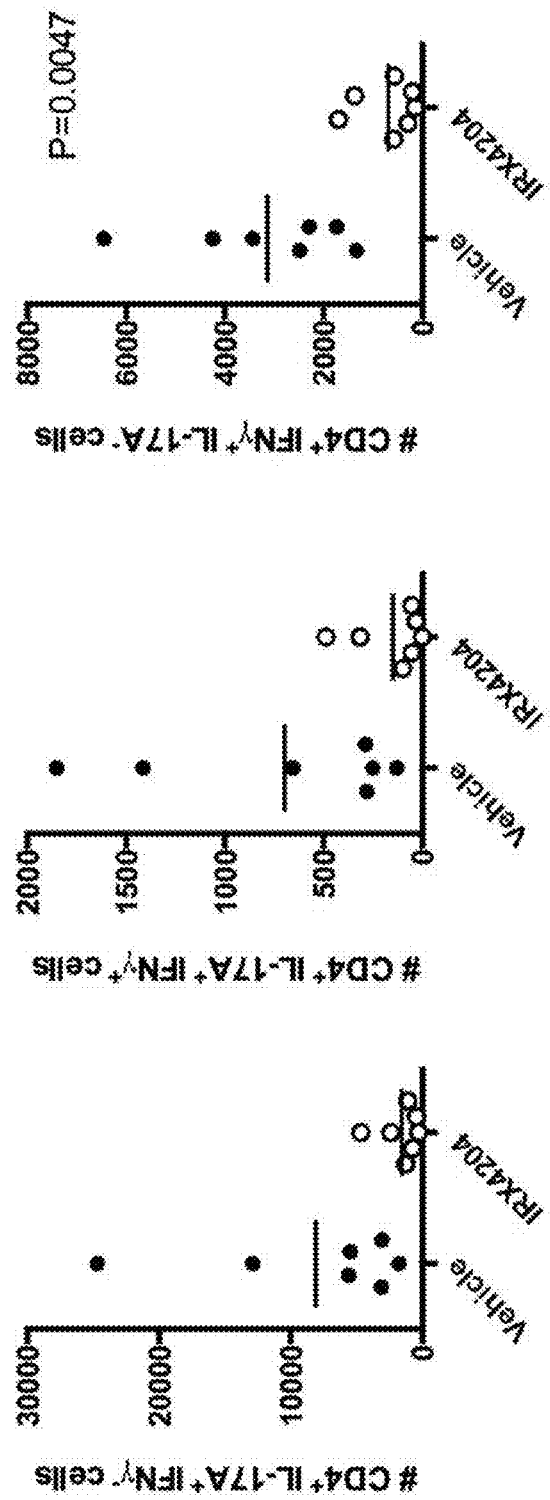

TREATMENT OF AUTOIMMUNE DISEASES WITH COMBINATIONS OF RXR AGONISTS AND THYROID HORMONES

RELATED APPLICATIONS

This application is a divisional of U.S. patent application Ser. No. 16/083,799, filed Sep. 10, 2018, now U.S. Pat. No. 10,946,001, which is a 35 U.S.C. 371 national phase entry of PCT/US2016/059772, filed Oct. 31, 2016, which claims priority to U.S. Provisional Patent Application No. 62/306,479, filed on Mar. 10, 2016. The entire content of each of these applications is herein incorporated by reference.

FIELD

The present disclosure is directed to methods of treating autoimmune diseases using Retinoid X Receptor (RXR) agonists in combination with thyroid hormones.

BACKGROUND

Compounds which have retinoid-like biological activity are well known in the art and are described in numerous United States patents including, but not limited to, U.S. Pat. Nos. 5,466,861; 5,675,033; and 5,917,082, all of which are herein incorporated by reference. Preclinical studies with rexinoids, which are agonists of RXRs, suggest that selective activation of Retinoid X Receptors (RXR), which modulate functions associated with differentiation, inhibition of cell growth, apoptosis and metastasis, may be useful in treating a variety of diseases associated with RXR.

Attempts to treat autoimmune disorders have met with limited success. This is due, in part, to the fact that the etiology of autoimmune disorders is a complex response based in part on a combination of factors, including, without limitation, genetic make-up of individual, gender or hormonal status, bacterial or viral infection, metal or chemical toxin exposure, vaccinations or immunizations, stress, trauma, smoking and/or nutritional deficiencies. Therefore, compounds, compositions, and methods that can reduce a symptom associated with an autoimmune disorder, inflammation associated with an autoimmune disorder, and/or a transplant rejection would be highly desirable.

There are two main types of receptors that mediate the effects of derivatives of vitamin A in mammals (and other organisms), the Retinoic Acid Receptors (RARs) and the RXRs. Within each type there are three subtypes designated RAR alpha, RAR beta, and RAR gamma for the RAR family and RXR alpha, RXR beta, and RXR gamma for the RXR family. These receptor types are evolutionarily related but are functionally distinct. The ligands that activate the RARs, referred to as retinoids, and the ligands that activate the RXRs, referred to as rexinoids, elicit quite different biological effects. Retinoic acid (RA), the physiological hormone for all three RARs, has been shown to enhance the in vitro differentiation of Treg cells that suppress immunity. RA can also inhibit the differentiation of pro-inflammatory Th17 cells that have been causally implicated in the development of many human autoimmune diseases. Based on this ability to restore a normal Th17/Treg cell ratio by decreasing Th17 cells while simultaneously increasing Treg cells, RAR agonists have been proposed as effective therapeutic compounds for the treatment of inflammatory and autoimmune disorders. However, recent findings have identified retinoid signaling through RARs as being required for the initial development of Th17 cell mediated immune responses and inflammation. These counteracting effects of RAR pan agonists on Th17 cell development bring into question the value of such compounds as anti-inflammatory and immunosuppressive agents.

Although RAR agonists like RA have been used to treat autoimmune disorders associated with inflammation, their usefulness in clinical practice has been limited due to unwanted side effects and counter-therapeutic inflammatory effects. Thus, what are needed are compounds and compositions that maintain the ability to inhibit Th17 cell formation and function and to promote Treg cell formation, but not possess any pro-inflammatory activities and other unwanted side effects associated with RAR pan agonists like RA. Such compounds will be of considerable therapeutic value as immunomodulatory agents.

SUMMARY

The activation of Retinoic Acid Receptors (RAR) by non-selective Retinoic X Receptor (RXR) agonists decreases the efficacy of the RXR agonists in autoimmune diseases. As such, the efficacy of RXR agonists in autoimmune diseases can be improved by administering the RXR agonist at a dose which activates RXR, while activating RAR minimally or not at all. It is now proposed that a RXR agonist at a dose which specifically activates only RXRs gives optimal anti-autoimmune disease activity when combined with administration of a thyroid hormone. Based on this proposal, novel methods of treating a patient with autoimmune diseases are disclosed herein.

Thus, disclosed herein is a method of treating an autoimmune disease, the method comprising administering to an individual in need thereof a therapeutically effective amount of a RXR agonist and a thyroid hormone, wherein administration of the RXR agonist and thyroid hormone treats the autoimmune disease in the individual more effectively than treatment with either the RXR agonist or thyroid hormone alone.

In certain embodiments, the RXR agonist is a selective RXR agonist having the structure of Formula II

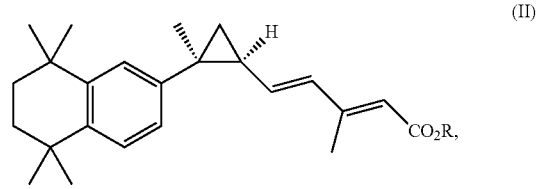

wherein R is H or lower alkyl of 1 to 6 carbons.

In some embodiments, the RXR agonist is a selective RXR agonist comprising 3,7-dimethyl-6(S),7(S)-methano, 7-[1,1,4,4-tetramethyl-1,2,3,4-tetrahydronaphth-7-yl]2(E),4(E) heptadienoic acid. In other embodiments, the RXR agonist is 3,7-dimethyl-6(S),7(S)-methano,7-[1,1,4,4-tetramethyl-1,2,3,4-tetrahydronaphth-7-yl]2(E),4(E) heptadienoic acid ethyl ester. In yet other embodiments, the RXR agonist is bexarotene. And, in still other embodiments, the RXR agonist is LG268. In some embodiments, the thyroid hormone is thyroxine.

In some embodiments, the therapeutically effective amount of the RXR agonist is about 0.001 mg/day to about 1000 mg/day. In other embodiments, the therapeutically effective amount of the ester of a RXR agonist is about 0.001 mg/day to about 1000 mg/day. In yet other embodiments, the therapeutically effective amount of the RXR agonist is about 10 mg/day to about 1000 mg/day, about 1.0 mg/day to about 100 mg/day, or about 1 mg/day to about 20 mg·day. In some embodiments, the dose of thyroxine is about 12.5 µg/day to about 250 µg/day.

In some embodiments, the RXR agonist is administered by nasal administration. In other embodiments, the RXR agonist and thyroxine are both administered by nasal administration. In other embodiments, the RXR agonist is administered orally. In yet other embodiments, the thyroxine is administered orally. In some embodiments, the thyroxine is administered subcutaneously.

In certain embodiments, the RXR agonist and the thyroxine are both administered substantially simultaneously. In other embodiments, the RXR agonist and thyroxine are administered on different schedules.

In certain embodiments, the method treats an autoimmune disease selected from the group consisting of acute disseminated encephalomyelitis (ADEM), Addison's disease, an allergy, allergic rhinitis, anti-phospholipid antibody syndrome (APS), an arthritis, asthma, acquired immunodeficiency syndrome (AIDS), autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastrointestinal disorder, a glomerulonephritis, Goodpasture's syndrome, Graves' disease, Guillain-Barré syndrome (GBS), Hashimoto's thyroiditis, hidradenitis suppurativa, idiopathic thrombocytopenic purpura, interstitial nephritis, interstitial cystitis, a lupus, morphea, multiple sclerosis (MS), myasthenia gravis, a myopathy, myositis, narcolepsy, neuromyotonia, pemphigus vulgaris, pernicious anaemia, primary biliary cirrhosis, psoriasis, psoriatic arthritis, a pulmonary fibrosis, recurrent disseminated encephalomyelitis, rheumatic fever, schizophrenia, scleroderma, Sjögren's syndrome, a skin disorder, tenosynovitis, uveitis, a vasculitis, or vitiligo.

In certain embodiments, the disease is not multiple sclerosis.

In certain embodiments, the arthritis is monoarthritis, oligoarthritis, polyarthritis, osteoarthritis, rheumatoid arthritis, juvenile idiopathic arthritis, septic arthritis, spondyloarthropathy, gout, pseudogout, or Still's disease.

In some embodiments, the gastrointestinal disorder is an irritable bowel disease or an inflammatory bowel disease. In other embodiments, the inflammatory bowel disease is Crohn's disease or ulcerative colitis.

In some embodiments, the lupus is discoid lupus erythematosus, drug-induced lupus erythematosus, lupus nephritis, neonatal lupus, subacute cutaneous lupus erythematosus, or systemic lupus erythematosus.

In some embodiments, the myopathy is dermatomyositis, inclusion body myositis, or polymyositis.

In some embodiments, the skin disorder is dermatitis, eczema, stasis dermatitis, hidradenitis suppurativa, psoriasis, rosacea, or scleroderma.

In some embodiments, the vasculitis is Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, or Wegener's granulomatosis.

In yet other embodiments, the autoimmune disease is multiple sclerosis, psoriasis, rheumatoid arthritis, glomerulonephritis, pulmonary fibrosis, interstitial nephritis, or an inflammatory bowel disease.

Also disclosed herein is a method of treating an autoimmune disease comprising of administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid, and thyroxine; and wherein administration of the combination reduces the severity of the autoimmune disease in the individual and more effectively than either the RXR agonist or thyroxine alone.

BRIEF DESCRIPTION OF THE DRAWINGS

FIG. 3A depicts the number of CD4$^+$ cells and FIG. 3B depicts the number of CD11c$^+$ CD11b$^+$ cells (myeloid DC) in mice treated with the selective RXR agonist IRX4204 (4204) versus the vehicle control.

FIGS. 11A-D depicts re-stimulation of the infiltrating lymphocytes of FIG. 10 to determine expression of interferon gamma (IFNγ) (FIG. 11A), IL-17A (FIG. 11B), tumor necrosis factor (TNF) (FIG. 11C), and IL-4 (FIG. 11D).

FIGS. 12A-C depicts the quantification of co-expression of IFNγ and IL-17A by CD4 T cells of FIG. 10 expressing IL-17A and not IFNγ (FIG. 12A), IL-17A and IFNγ (FIG. 12B), IFNγ and not IL-17A (FIG. 12C).

FIG. 15B: 1 nM IRX4204; FIG. 15C: 0.1 nM IRX4204). *P<0.0001; P<0.01.

FIG. 16A depicts remyelination in the hippocampus and FIG. 16B depicts remyelination in the cortex.

FIG. 20A depicts the myelinated axons per CC unit; FIG. 20B depicts the density of myelinated axons (per 10,000 µm$^2$); and FIG. 20C depicts the density of SM132+ ovoids (per 250,000 µm$^2$).

DETAILED DESCRIPTION

Figure 1:
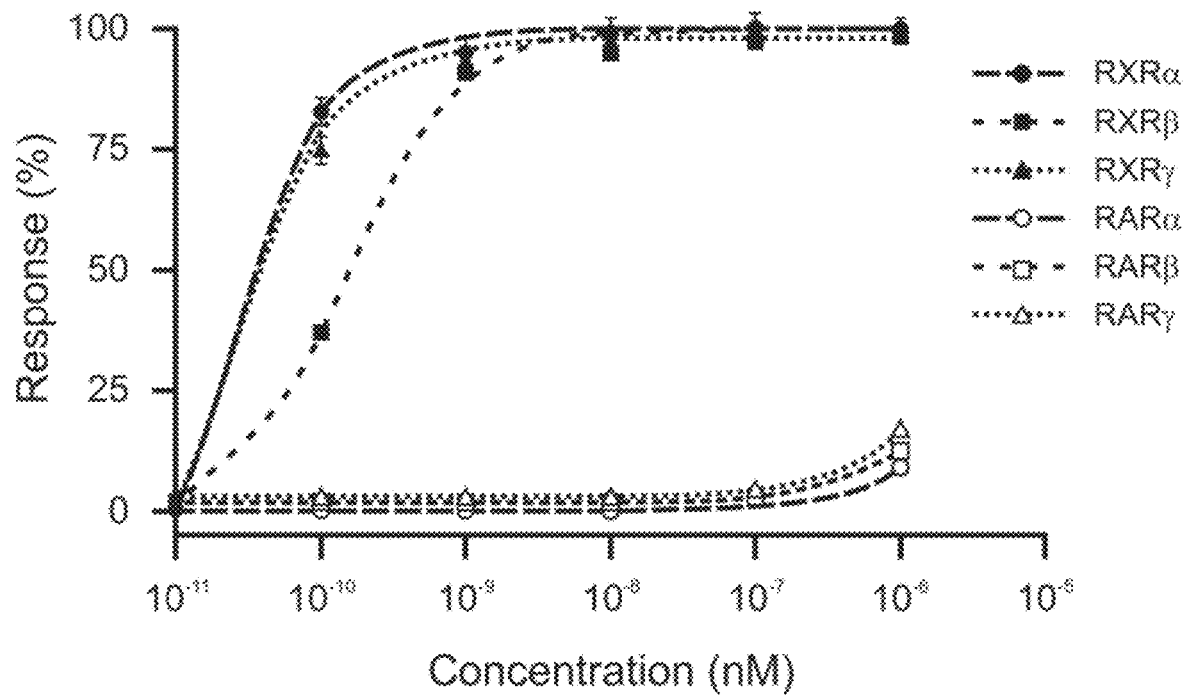
FIG. 1 shows RXR agonist activation of transcription from RXRα, RXRβ, RXRγ, RARα, RARβ, and RARγ using transactivation assays.

Preclinical studies with rexinoids suggest that selective activation of Retinoid X Receptors (RXR), which modulate functions associated with differentiation, inhibition of cell growth, apoptosis and metastasis, may be useful in treating a variety of diseases.

The RARs and RXRs and their cognate ligands function by distinct mechanisms. RAR means one or more of RAR α, β and γ. RXR generally means one or more of RXR α, β, and γ. A RAR biomarker is a distinctive biological, biochemical or biologically derived indicator that signifies patient RAR activity. RAR biomarkers include, but are not limited to, CYP26 levels, CRBPI levels and the like and combinations thereof.

RAR activation threshold means one or more of (1) a CYP26 level which is 25% increased over baseline and (2) a CRBPI level 25% increased over baseline. The RARs always form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, RXR agonists do not activate RAR/RXR heterodimers. RXR heterodimer complexes like RAR/RXR can be referred to as non-permissive RXR heterodimers as activation of transcription due to ligand-binding occurs only at the non-RXR protein (e.g., RAR); activation of transcription does not occur due to ligand binding at the RXR. RXRs also interact with nuclear receptors other than RARs and RXR agonists may elicit some of its biological effects by binding to such RXR/receptor complexes.

These RXR/receptor complexes can be referred to as permissive RXR heterodimers as activation of transcription due to ligand-binding could occur at the RXR, the other receptor, or both receptors. Examples of permissive RXR heterodimers include, without limitation, peroxisome proliferator activated receptor/RXR (PPAR/RXR), farnesyl X receptor/RXR (FXR/RXR), nuclear receptor related-1 protein/RXR (Nurr1/RXR) and liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids, such as pro-inflammatory responses or mucocutaneous toxicity, are mediated by activation of one or more of the RAR receptor subtypes. Stated another way, biological effects mediated via RXR pathways would not induce pro-inflammatory responses, and thus, would not result in unwanted side effects.

Thus, aspects of the present specification provide, in part, a RXR agonist. As used herein, the term "RXR agonist" is synonymous with "RXR selective agonist" and refers to a compound that selectively binds to one or more RXR receptors like a RXRα, a RXRβ, or a RXRγ in a manner that elicits gene transcription via an RXR response element. As used herein, the term "selectively binds," when made in reference to a RXR agonist, refers to the discriminatory binding of a RXR agonist to the indicated target receptor like a RXRα, a RXRβ, or a RXRγ such that the RXR agonist does not substantially bind with non-target receptors like a RARα, a RARβ or a RARγ. In some embodiments, the term "RXR agonist" includes esters of RXR agonists.

In one embodiment, the selective RXR agonist does not activate to any appreciable degree the permissive heterodimers PPAR/RXR, FXR/RXR, and LXR/RXR. In another embodiment, the RXR agonist activates the heterodimer Nurr1/RXR. One example of such a selective RXR agonist is 3,7-dimethyl-6(S),7(S)-methano,7-[1,1,4,4-tetramethyl-1, 2,3,4-tetrahydronaphth-7-yl]2(E),4(E) heptadienoic acid (IRX4204) disclosed herein, the structure of which is shown in Formula III. In other aspects of this embodiment, the RXR agonists, activates the permissive heterodimers PPAR/RXR, FXR/RXR, or LXR/RXR by about 1% or less, about 2% or less, about 3% or less, about 4% or less, about 5% or less, about 6% or less, about 7% or less, about 8% or less, about 9% or less, or about 10% or less relative to the ability of activating agonists to the non-RXR receptor to activate the same permissive heterodimer. Examples of RXR agonists, which activates one or more of PPAR/RXR, FXR/RXR, or LXR/RXR include LGD1069 (bexarotene) and LGD268.

IRX4204, like some other RXR ligands, does not activate non-permissive heterodimers such as RAR/RXR. However, IRX4204 is unique in that it specifically activates the Nurr1/RXR heterodimer and does not activate other permissive RXR heterodimers such as PPAR/RXR, FXR/RXR, and LXR/RXR. Other RXR ligands generally activate these permissive RXR heterodimers. Thus, all RXR ligands cannot be classified as belonging to one class. IRX4204 belongs to a unique class of RXR ligands which specifically activate RXR homodimers and only one of the permissive RXR heterodimers, namely the Nurr1/RXR heterodimer.

Binding specificity is the ability of a RXR agonist, to discriminate between a RXR receptor and a receptor that does not contain its binding site, such as a RAR receptor.

More specifically, disclosed herein are esters of RXR agonists. An ester may be derived from a carboxylic acid of C1, or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Thus, disclosed herein are RXR agonists, or esters thereof, having the structure of formula I:

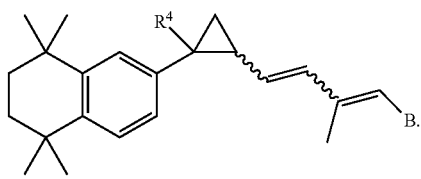

(I)

where $R^4$ is lower alkyl of 1 to 6 carbons; B is —COOR$^8$ where $R^8$ is hydrogen or a lower alkyl of 1 to 6 carbons, and the configuration about the cyclopropane ring is cis, and the configuration about the double bonds in the pentadienoic acid or ester chain attached to the cyclopropane ring is trans in each of the double bonds.

In an exemplary embodiment, an ester of a RXR agonist is a compound having the structure of formula II:

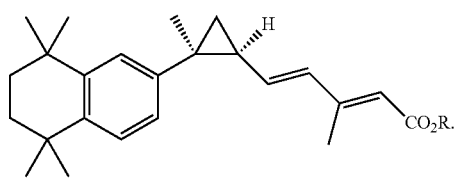

(II)

wherein R is H or lower alkyl of 1 to 6 carbons.

In a further exemplary embodiment, a RXR agonist may be a selective RXR agonist comprising 3,7-dimethyl-6(S),7(S)-methano,7-[1,1,4,4-tetramethyl-1,2,3,4-tetrahydronaphth-7-yl]2(E),4(E) heptadienoic acid (IRX4204), and has the structure of formula III, and esters thereof:

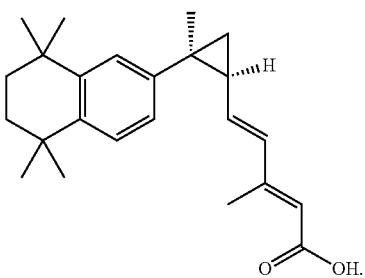

(III)

In certain embodiments, the RXR agonist may be bexarotene (TARGRETIN®, 4-[1-(3,5,5,8,8-pentamethyl-6,7-dihydronaphthalen-2-yl)ethenyl]benzoic acid, LGD1069, Mylan Pharmaceuticals, Inc.), or esters thereof, and has the structure of formula IV:

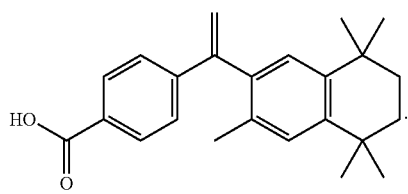

(IV)

In other embodiments, the RXR agonist may be LG268 (LG100268, LGD268, 2-[1-(3,5,5,8,8-pentamethyl-5,6,7,8-tetrahydro-2-naphthyl)cyclopropyl]pyridine-5-carboxylic acid), or esters thereof and has the structure of formula V:

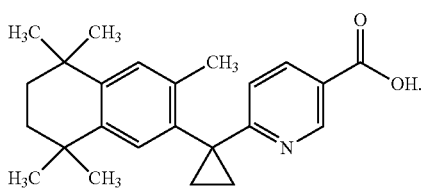

(V)

Pharmaceutically acceptable salts of RXR agonists, or esters thereof, can also be used in the disclosed method. Compounds disclosed herein which possess a sufficiently acidic, a sufficiently basic, or both, functional group, and accordingly can react with any of a number of organic or inorganic bases, and inorganic and organic acids, to form a salt.

Administration of RXR agonists, or esters thereof, may lead to the suppression of serum thyroid hormones and possibly to hypothyroidism and related conditions. In some embodiments, a thyroid hormone may be used in combination with the RXR agonists, or esters thereof. As used herein, the term "thyroid hormone" refers to thyroxine and triiodothyronine. Thyroxine (thyroid hormone $T_4$, levothyroxine sodium) is a tyrosine-based hormone produced by the thyroid gland and is primarily responsible for regulation of metabolism. Thyroxine is a prohormone for triiodothyronine ($T_3$). RXR agonists are known to suppress thyroid function. However, supplementation of RXR agonist therapy with thyroid hormones has not been utilized therapeutically to enhance the anti-autoimmune effects of the RXR agonist.

Aspects of the present specification provide, in part, a composition comprising a RXR agonist, or esters or other derivatives thereof, and a thyroid hormone. Exemplary RXR agonists are IRX4204, bexarotene, and LG268. Exemplary esters of RXR agonists are IRX4204 ethyl ester (IRX4204EE), an ester of bexarotene, and an ester of LG268.

Aspects of the methods of the present disclosure include, in part, treatment of a mammal. A mammal includes a human, and a human can be a patient. Other aspects of the present disclosure provide, in part, an individual. An individual includes a mammal and a human, and a human can be a patient.

RXR agonists, or esters thereof, disclosed herein, or a composition comprising an RXR agonists or esters thereof, or a combination of RXR agonists, or esters thereof, and a thyroid hormone, such as thyroxine, is generally administered to an individual as a pharmaceutical composition.

Pharmaceutical compositions may be prepared by combining a therapeutically effective amount of at least one RXR agonist, as an active ingredient, with conventional acceptable pharmaceutical excipients, and by preparation of unit dosage forms suitable for therapeutic use. As used herein, the term "pharmaceutical composition" refers to a therapeutically effective concentration of an active compound, such as any of the compounds disclosed herein. Preferably, the pharmaceutical composition does not produce an adverse, allergic, or other untoward or unwanted reaction when administered to an individual. A pharmaceutical composition disclosed herein is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition produced using the methods disclosed herein may be a liquid formulation, semi-solid formulation, or a solid formulation. A formulation disclosed herein can be produced in a manner to form one phase, such as, but not limited to an oil or a solid. Alternatively, a formulation disclosed herein can be produced in a manner to form two phases, such as an emulsion. A pharmaceutical composition disclosed herein intended for such administration may be prepared according to any method known to the art for the manufacture of pharmaceutical compositions.

Liquid formulations suitable for parenteral injection or for nasal sprays may comprise physiologically acceptable sterile aqueous or nonaqueous solutions, dispersions, suspensions or emulsions and sterile powders for reconstitution into sterile injectable solutions or dispersions. Formulations suitable for nasal administration may comprise physiologically acceptable sterile aqueous or nonaqueous solutions, dispersions, suspensions or emulsions. Examples of suitable aqueous and nonaqueous carriers, diluents, solvents or vehicles include, but are not limited to, water, ethanol, polyols (propylene glycol, polyethyleneglycol (PEG), glycerol, and the like), suitable mixtures thereof, vegetable oils (such as olive oil or peanut oil) and injectable organic esters such as ethyl oleate. Proper fluidity can be maintained, for example, by the use of a coating such as lecithin, by the maintenance of the required particle size in the case of dispersions and by the use of surfactants.

Aqueous suspensions may include pharmaceutically acceptable excipients such as, but not limited to, a) suspending agents, as for example, sodium carboxymethyl cellulose, methylcellulose, hydroxypropylmethylcellulose, sodium alginate, polyvinylpyrrolidone, gum tragacanth and gum acacia; b) dispersing or wetting agents, as for naturally occurring phosphatide or lecithin, or condensation products of an alkylene oxide with fatty acids, such as, but not limited to, polyoxyethylene stearate, or condensation products of ethylene oxide with long chain aliphatic alcohols, such as, but not limited to, heptadecaethylene-oxycetanol, or condensation products of ethylene oxide with partial esters derived from fatty acids and a hexitol, such as polyoxyethylene sorbitol monoleate or condensation products of ethylene oxide with partial esters derived from fatty acids and hexitol anhydrides, such as, but not limited to, polyoxyethylene sorbitan monoleate. The aqueous suspensions can also contain one or more preservatives, ethyl- or -n-propyl-p-hydroxy benzoate, one or more coloring agents, one or more flavoring agents and one or more sweetening agents, such as, but not limited to, sucrose, saccharin or sodium or calcium cyclamate.

Pharmaceutical formulations suitable for administration by inhalation include fine particle dusts or mists, which may be generated by means of various types of metered, dose pressurized aerosols, nebulizers, or insufflators.

Semi-solid formulations suitable for topical administration include, without limitation, ointments, creams, salves, and gels. In such solid formulations, the active compound may be admixed with at least one inert customary excipient (or carrier) such as, but not limited to, a lipid and/or polyethylene glycol.

Solid formulations suitable for oral administration include capsules, tablets, pills, powders and granules. In such solid formulations, the active compound may be admixed with at least one inert customary excipient (or carrier) such as, but not limited to, sodium citrate or dicalcium phosphate or (a) fillers or extenders, for example but not limited to, starches, lactose, sucrose, glucose, mannitol and silicic acid, (b) binders, for example but not limited to, carboxymethylcellulose, alignates, gelatin, polyvinylpyrrolidone, sucrose and acacia, (c) humectants, for example, but not limited to, glycerol, (d) disintegrating agents, for example, but not limited to, agar-agar, calcium carbonate, potato or tapioca starch, alginic acid, certain complex silicates and sodium carbonate, (e) solution retarders, for example, but not limited to, paraffin, (f) absorption accelerators, for example, but not limited to, quaternary ammonium compounds, (g) wetting agents, for example, but not limited to, cetyl alcohol and glycerol monostearate, (h) adsorbents, for example, but not limited to, kaolin and bentonite, and (i) lubricants, for example, but not limited to, talc, calcium stearate, magnesium stearate, solid polyethylene glycols, sodium lauryl sulfate or mixtures thereof. In the case of capsules, tablets and pills, the dosage forms may also comprise buffering agents.

In liquid and semi-solid formulations, a concentration of an RXR agonist typically may be between about 50 mg/mL to about 1,000 mg/mL. In aspects of this embodiment, a therapeutically effective amount of a therapeutic compound disclosed herein may be from about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, about 600 mg/mL to about 1,000 mg/mL, or any other range bound by these values.

In semi-solid and solid formulations, an amount of a RXR agonist may be between about 0.01% to about 45% by weight. In aspects of this embodiment, an amount of a therapeutic compound disclosed herein may be from about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, about 25% to about 30% by weight, or any other range bound by these values.

A pharmaceutical composition disclosed herein may optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent.

Any of a variety of pharmaceutically acceptable carriers may be used including, without limitation, aqueous media such as water, saline, glycine, hyaluronic acid and the like; solid carriers such as starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wilkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, $4^{th}$ edition 2003). These protocols are routine and any modifications are well within the scope of one skilled in the art and from the teaching herein.

A pharmaceutical composition disclosed herein may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH may be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed.

Pharmaceutically acceptable antioxidants include, without limitation, sodium metabisulfite, sodium thiosulfate, acetylcysteine, butylated hydroxyanisole, and butylated hydroxytoluene. Useful preservatives may include, but not limited to, benzalkonium chloride, chlorobutanol, thimerosal, phenylmercuric acetate, phenylmercuric nitrate, a stabilized oxy chloro composition, sodium chlorite and chelants, DTPA or DTPA-bisamide, calcium DTPA, and CaNaDTPA-bisamide. Tonicity adjustors useful in a pharmaceutical composition may include, but are not limited to, salts such as sodium chloride, potassium chloride, mannitol or glycerin and other pharmaceutically acceptable tonicity adjustor. The pharmaceutical composition may be provided as a salt and can be formed with many acids, including, but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful herein.

The compounds disclosed herein, such as a combination of an RXR agonist and thyroxine, may also be incorporated into a drug delivery platform in order to achieve a controlled compound release profile over time. Such a drug delivery platform may comprise the combination disclosed herein dispersed within a polymer matrix, typically a biodegradable, bioerodible, and/or bioresorbable polymer matrix. As used herein, the term "polymer" refers to synthetic homo- or copolymers, naturally occurring homo- or copolymers, as well as synthetic modifications or derivatives thereof having a linear, branched or star structure. Copolymers can be arranged in any form, such as random, block, segmented, tapered blocks, graft, or triblock. Polymers are generally condensation polymers. Polymers can be further modified to enhance their mechanical or degradation properties by introducing cross-linking agents or changing the hydrophobicity of the side residues. If crosslinked, polymers are usually less than 5% crosslinked, usually less than 1% crosslinked.

Suitable polymers may include, but are not limited to, alginates, aliphatic polyesters, polyalkylene oxalates, polyamides, polyamidoesters, polyanhydrides, polycarbonates, polyesters, polyethylene glycol, polyhydroxyaliphatic carboxylic acids, polyorthoesters, polyoxaesters, polypeptides, polyphosphazenes, polysaccharides, and polyurethanes. The polymer usually comprises at least about 10% (w/w), at least about 20% (w/w), at least about 30% (w/w), at least about 40% (w/w), at least about 50% (w/w), at least about 60% (w/w), at least about 70% (w/w), at least about 80% (w/w), or at least about 90% (w/w) of the drug delivery platform. Examples of biodegradable, bioerodible, and/or bioresorbable polymers and methods useful to make a drug delivery platform are described in U.S. Pat. Nos. 4,756,911; 5,378,475; 7,048,946; and U.S. Patent Publication Nos. 2005/0181017; 2005/0244464; 2011/0008437; each of which is incorporated by reference for all it discloses regarding drug delivery.

In aspects of this embodiment, a polymer composing the matrix may be a polypeptide such as, but not limited to, silk fibroin, keratin, or collagen. In other aspects of this embodiment, a polymer composing the matrix may be a polysaccharide such as, but not limited to, cellulose, agarose, elastin, chitosan, chitin, or a glycosaminoglycan like chondroitin sulfate, dermatan sulfate, keratan sulfate, or hyaluronic acid. In yet other aspects of this embodiment, a polymer composing the matrix may be a polyester such as D-lactic acid, L-lactic acid, racemic lactic acid, glycolic acid, caprolactone, and combinations thereof.

One of ordinary skill in the art appreciates that the selection of a suitable polymer for forming a suitable disclosed drug delivery platform depends on several factors. The more relevant factors in the selection of the appropriate polymer(s), include, without limitation, compatibility of polymer with drug, desired release kinetics of drug, desired biodegradation kinetics of platform at implantation site, desired bioerodible kinetics of platform at implantation site, desired bioresorbable kinetics of platform at implantation site, in vivo mechanical performance of platform, processing temperatures, biocompatibility of platform, and patient tolerance. Other relevant factors that, to some extent, dictate the in vitro and in vivo behavior of the polymer include the chemical composition, spatial distribution of the constituents, the molecular weight of the polymer and the degree of crystallinity.

A drug delivery platform may include both a sustained release drug delivery platform and an extended release drug delivery platform. As used herein, the term "sustained release" refers to the release of a compound disclosed herein over a period of about seven days or more. As used herein, the term "extended release" refers to the release of a compound disclosed herein over a period of time of less than about seven days.

In aspects of this embodiment, a sustained release drug delivery platform may release a RXR agonist disclosed herein, or the combination an RXR agonist and a thyroid hormone, with substantially first order release kinetics over a period of about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a compound disclosed herein with substantially first order release kinetics over a period of at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform may release a RXR agonist disclosed herein, and a thyroid hormone, with substantially first order release kinetics over a period of about 1 day after administration, about 2 days after administration, about 3 days after administration, about 4 days after administration, about 5 days after administration, or about 6 days after administration. In other aspects of this embodiment, a drug delivery platform releases a compound disclosed herein with substantially first order release kinetics over a period of at most 1 day after administration, at most 2 days after administration, at most 3 days after administration, at most 4 days after administration, at most 5 days after administration, or at most 6 days after administration.

Aspects of the present disclosure include, in part, administering a RXR agonist, or a RXR agonist in combination with a thyroid hormone, such as thyroxine. As used herein, the term "administering" means any delivery mechanism that provides a compound, a composition, or a combination disclosed herein to an individual that potentially results in a clinically, therapeutically, or experimentally beneficial result.

Administration of a RXR agonist, in combination with a thyroid hormone, disclosed herein may include individually a variety of enteral or parenteral approaches including, without limitation, oral administration in any acceptable form, such as tablet, liquid, capsule, powder, or the like; topical administration in any acceptable form, such as drops, spray, creams, gels or ointments; buccal, nasal, and/or inhalation administration in any acceptable form; rectal administration in any acceptable form; vaginal administration in any acceptable form; intravascular administration in any acceptable form, such as intravenous bolus injection, intravenous infusion, intra-arterial bolus injection, intra-arterial infusion and catheter instillation into the vasculature; pen- and intra-tissue administration in any acceptable form, such as intraperitoneal injection, intramuscular injection, subcutaneous injection, subcutaneous infusion, intraocular injection, retinal injection, or sub-retinal injection or epidural injection; intravesicular administration in any acceptable form, such as catheter instillation; and by placement device, such as an implant, a stent, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A compound, a composition, or a combination disclosed herein may be administered to a mammal using a variety of routes. Routes of administration suitable for treating an autoimmune disease as disclosed herein include both local and systemic administration. Local administration results in significantly more delivery of a compound, a composition, or a combination disclosed herein to a specific location as compared to the entire body of the mammal, whereas, systemic administration results in delivery of a compound, a composition, or a combination to essentially the entire body of the individual.

The actual route of administration of a compound, a composition, or a combination disclosed herein used can be determined by a person of ordinary skill in the art by taking into account factors, including, without limitation, the duration of treatment desired, the degree of relief desired, the duration of relief desired, the particular compound, composition, or combination, the rate of excretion of the compound, composition, or combination used, the pharmacodynamics of the compound, composition, or combination used, the nature of the other compounds to be included in the composition or combination, the particular route of administration, the particular characteristics, history and risk factors of the individual, such as, age, weight, general health and the like, the response of the individual to the treatment, or any combination thereof. An effective dosage amount of a compound, a composition, or a combination disclosed herein can thus readily be determined by the person of ordinary skill in the art considering all criteria and utilizing his best judgment on the individual's behalf.

In an embodiment, a compound, a composition, or a combination disclosed herein is administered systemically to a mammal. In another embodiment, a compound, a composition, or a combination disclosed herein is administered locally to a mammal. In an aspect of this embodiment, a compound, a composition, or a combination disclosed herein is administered to the site of an autoimmune disorder in the mammal.

In other embodiments, RXR agonists may be administered orally, buccally, by nasal, and/or inhalation administration, intravascularly, intravenously, by intraperitoneal injection, intramuscularly, subcutaneously, intraocularly injection, by epidural injection, or by intravesicular administration; and thyroxine may be administered orally or subcutaneously or by another route. The RXR agonists, and the thyroid hormone do not need to be administered by the same route or on the same administration schedule.

Aspects of the present specification provide, in part, administering a therapeutically effective amount of a RXR agonist in combination with a thyroid hormone. As used herein, the term "therapeutically effective amount" is synonymous with "therapeutically effective dose" and when used in reference to treating an autoimmune disease means a dose of a compound, a composition, or a combination necessary to achieve the desired therapeutic effect and includes a dose sufficient to reduce tumor burden or place a patient into a clinical remission. The amount of active component in a compound, composition, or combination disclosed herein for treating an autoimmune disorder may be varied so that a suitable dosage is obtained.

Additionally, where repeated administration of a compound, a composition, or a combination disclosed herein is used, the actual effect amount of compound, composition, or combination disclosed herein will further depend upon factors, including, without limitation, the frequency of administration, the half-life of the compound, composition, or combination disclosed herein. It is known by a person of ordinary skill in the art that an effective amount of a compound or a composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a RXR agonist disclosed herein to a mammal, a therapeutically effective amount generally may be in the range of about 0.001 mg/day to about 3000 mg/day. In aspects of this embodiment, an effective amount of a compound or a composition disclosed herein may be about 0.01 mg/day to about 0.1 mg/day, about 0.03 mg/day to about 3.0 mg/day, about 0.1 mg/day to about 3.0 mg/day, about 0.3 mg/day to about 3.0 mg/day, about 1 mg/day to about 3 mg/day, about 3 mg/day to about 30 mg/day, about 10 mg/day to about 30 mg/day, about 10 mg/day to about 100 mg/day, about 30 mg/day to about 100 mg/day, about 100 mg/day to about 1000 mg/day, about 100 mg/day to about 300 mg/day, about 1000 mg/day to about 3000 mg/day, about 1 mg/day to about 100 mg/day, or about 1 mg/day to about 20 mg/day. In yet other aspects of this embodiment, a therapeutically effective amount of a compound or a composition disclosed herein may be at least 0.001 mg/kg/day, at least 0.01 mg/day, at least 0.1 mg/day, at least 1.0 mg/day, at least 3.0 mg/day, at least 10 mg/day, at least 30 mg/day, at least 100 mg/day, at least 300 mg/day, or at least 1000 mg/day. In yet other aspects of this embodiment, a therapeutically effective amount of a compound or a composition disclosed herein may be at most 0.001 mg/day, at most 0.01 mg/day, at most 0.1 mg/day, at most 1.0 mg/day, at most 3.0 mg/day, at most 10 mg/day, at most 30 mg/day, at most 100 mg/day, at most 300 mg/day, at most 1000 mg/day, or at most 3000 mg/day.

Suitable thyroxine doses are generally from about 12.5 µg/day to about 250 µg/day orally initially with an increase in dose of about 12.5 to about 25 µg daily increments every 2-4 weeks as needed. In other embodiments, the suitable thyroxine dose is from about 5 µg/day to about 225 µg/day, from about 7.5 µg/day to about 200 µg/day, from about 10 µg/day to about 175 µg/day, from about 12.5 µg/day to about 150 µg/day, from about 15 µg/day to about 125 µg/day, from about 17.5 µg/day to about 100 µg/day, from about 20 µg/day to about 100 µg/day, from about 22.5 µg/day to about 100 µg/day, from about 25 µg/day to about 100 µg/day, from about 5 µg/day to about 200 µg/day, from about 5 µg/day to about 100 µg/day, from about 7.5 µg/day to about 90 µg/day, from about 10 µg/day to about 80 µg/day, from about 12.5 µg/day to about 60 µg/day, or from about 15 µg/day to about 50 µg/day. Increases in dose are generally made in increments of about 5 µg/day, about 7.5 µg/day, about 10 µg/day, about 12.5 µg/day, about 15 µg/day, about 20 µg/day, or about 25 µg/day. In certain embodiments, the suitable thyroid hormone dose is a dose able to produce serum levels of T4 in the top 50%, the top 60%, the top 70%, the top 80%, or the top 90% of the normal range for the testing laboratory. As the normal range of T4 levels may vary by testing laboratory, the target T4 levels are based on normal ranges determined for each particular testing laboratory.

Dosing may be single dosage or cumulative (serial dosing), and may be readily determined by one skilled in the art. For instance, treatment of an autoimmune disease may comprise a one-time administration of an effective dose of a compound, composition, or combination disclosed herein. As a non-limiting example, an effective dose of a compound, composition, or combination disclosed herein can be administered once to a mammal as a single injection or deposition at or near the site exhibiting a symptom of an autoimmune disease or a single oral administration of the compound, composition, or combination. Alternatively, treatment of an autoimmune disease may comprise multiple administrations of an effective dose of a compound, composition, or combination disclosed herein carried out over a range of time periods, such as daily, once every few days, weekly, monthly or yearly.

As a non-limiting example, a compound, a composition, or a combination disclosed herein may be administered once or twice weekly to a mammal. The timing of administration can vary from mammal to mammal, depending upon such factors as the severity of a mammal's symptoms. For example, an effective dose of a compound, composition, or combination disclosed herein can be administered to a mammal once a month for an indefinite period of time, or until the mammal no longer requires therapy. A person of ordinary skill in the art will recognize that the condition of the mammal can be monitored throughout the course of treatment and that the effective amount of a compound, composition, or combination disclosed herein that is administered can be adjusted accordingly.

In other embodiments, the method may further include measuring the patient's $C_{max}$ of the RXR agonist and adjusting the dose to maintain the patient's $C_{max}$ at an optimal level.

In one embodiment, the RXR agonist is 3,7-dimethyl-6(S),7(S)-methano,7-[1,1,4,4-tetramethyl-1,2,3,4-tetrahydron-aphth-7-yl]2(E),4(E) heptadienoic acid or esters thereof. In another embodiment, the RXR agonist is TARGRETIN® or esters thereof. In another embodiment, the RXR agonist may be may be LG268 (LG100268, LGD268, 2-[1-(3,5,5,8,8-pentamethyl-5,6,7,8-tetrahydro-2-naphthyl)cyclopropyl]pyridine-5-carboxylic acid), or esters thereof.

In some embodiments, the method further includes treating the patient with one or more triglyceride lowering agents.

The autoimmune disorder can be a systemic autoimmune disorder or an organ-specific autoimmune disorder. Non-limiting examples of an autoimmune disorder that can be treated using a compound, composition, or combination disclosed herein include acute disseminated encephalomyelitis (ADEM), Addison's disease, an allergy, allergic rhinitis, anti-phospholipid antibody syndrome (APS), an arthritis such as, e.g., monoarthritis, oligoarthritis, or a polyarthritis like osteoarthritis, rheumatoid arthritis, juvenile idiopathic arthritis, septic arthritis, spondyloarthropathy, gout, pseudogout, or Still's disease, asthma, acquired immunodeficiency syndrome, acquired immunodeficiency syndrome (AIDS), autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, a gastrointestinal disorder such as, e.g., an irritable bowel disease or an inflammatory bowel disease like Crohn's disease or ulcerative colitis, a glomerulonephritis, Goodpasture's syndrome, Graves' disease, Guillain-Barré syndrome (GBS), Hashimoto's thyroiditis, hidradenitis suppurativa, idiopathic thrombocytopenic purpura, interstitial nephritis, interstitial cystitis, a lupus, such as, e.g., discoid lupus erythematosus, drug-induced lupus erythematosus. lupus nephritis, neonatal lupus, subacute cutaneous lupus erythematosus, or systemic lupus erythematosus, morphea, multiple sclerosis (MS), myasthenia gravis, a myopathy such as, e.g., dermatomyositis, inclusion body myositis, or polymyositis, myositis, narcolepsy, neuromyotonia, pemphigus vulgaris, pernicious anaemia, primary biliary cirrhosis, psoriasis, psoriatic arthritis, a pulmonary fibrosis, recurrent disseminated encephalomyelitis, rheumatic fever, schizophrenia, scleroderma, Sjögren's syndrome, a skin disorder such as, e.g., dermatitis, eczema, stasis dermatitis, hidradenitis suppurativa, psoriasis, rosacea or scleroderma, tenosynovitis, uveitis, a vasculitis such as, e.g., Buerger's disease, cerebral vasculitis, Churg-Strauss arteritis, cryoglobulinemia, essential cryoglobulinemic vasculitis, giant cell arteritis, Golfer's vasculitis, Henoch-Schonlein purpura, hypersensitivity vasculitis, Kawasaki disease, microscopic polyarteritis/polyangiitis, polyarteritis nodosa, polymyalgia rheumatica (PMR), rheumatoid vasculitis, Takayasu arteritis, Wegener's granulomatosis, or vitiligo.

In some embodiments, the disease is not multiple sclerosis.

In certain embodiments, the autoimmune disease is psoriasis, glomerulonephritis, pulmonary fibrosis, rheumatoid arthritis, or an inflammatory bowel disease.

Aspects of the present disclosure includes, in part, reducing at least one symptom associated with an autoimmune disorder. The actual symptoms associated with an autoimmune disorder disclosed herein are well known and can be determined by a person of ordinary skill in the art by taking into account factors, including, without limitation, the location of the autoimmune disorder, the cause of the autoimmune disorder, the severity of the autoimmune disorder, the tissue or organ affected by the autoimmune, and the inflammation associated with the autoimmune disorder. Non-limiting examples of a symptom reduced by a method of treating an autoimmune disorder disclosed herein include inflammation, fatigue, pain, cognitive deficits, neurologic deficits, dizziness, malaise, elevated fever and high body temperature, extreme sensitivity to cold in the hands and feet, weakness, soreness, and/or stiffness in muscles and joints, weight changes, digestive or gastrointestinal problems, breathing problems, low or high blood pressure, irritability, anxiety, or depression, infertility or reduced sex drive (low libido), blood sugar changes, and depending on the type of autoimmune disease, an increase in the size of an organ or tissue, or the destruction of an organ or tissue. Non-limiting examples of an inflammation symptom reduced by a method of treating an autoimmune disorder disclosed herein include pain, loss of neurologic function, loss of cognitive function, edema, hyperemia, erythema, bruising, tenderness, stiffness, swollenness, fever, a chill, congestion of the respiratory tract including nose, and bronchi, congestion of a sinus, a breathing problem, fluid retention, a blood clot, a loss of appetite, an increased heart rate, a formation of granulomas, fibrinous, pus, or non-viscous serous fluid, a formation of an ulcer, or pain.

In certain embodiments, treatment with a combination of an RXR agonist and a thyroid hormone reduces at least one symptom, at least two symptoms, at least three symptoms, at least four symptoms, or at least five symptoms of an autoimmune disorder.

In other embodiments, the method may help to treat or alleviate conditions, symptoms, or disorders related to autoimmune diseases. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss. In other embodiments, the administration of the combination of the RXR agonist with the thyroid hormone prolongs the survival of the individual being treated.

In some embodiments of the method, the mammal may experience improvements from the autoimmune disease as a result of treatment with the combination of RXR agonist and a thyroid hormone.

In some embodiments, the method may treat rheumatoid arthritis. Rheumatoid arthritis is a chronic inflammatory disorder which causes pain and swelling in a patient's joints, generally effecting joints in the hands, wrist, feet, elbows, knees, hips, shoulders, and ankles. Rheumatoid arthritis is an autoimmune disease believed to be caused by the patient's immune system attacking the patient's joints causing inflammation and joint damage. Inflammation may cause damage to the cartilage and bone of the joint. Such damage can cause narrowing of joint spacing and leading the joints to become loose, unstable, painful, and immobile.

Clinical diagnosis of rheumatoid arthritis may be measured through the disease activity score (DAS). The DAS is a clinical index to measure rheumatoid arthritis disease activity by combining information measured from swollen joints, tender joints, the acute phase response, and general health. The DAS has a continuous scale ranging from 0-10. The level of disease activity may be interpreted as low (DAS<2.4), moderate (2.4<DAS<3.7), or high (DAS>3.7). A DAS<1.6 corresponds to a state of remission according to the American Rheumatism Association (ARA) criteria. The DAS28 is a variation of DAS. DAS28 consists of a 28 tender joint count, a 28 swollen joint count (range 0-28), erythrocyte sedimentation rate (ESR), and an optional general health assessment on a visual analogue scale (range 0-100). The level of disease activity can be interpreted as low (DAS28<3.2), moderate (3.2<DAS28<5.1), or high (DAS28>5.1). The DAS28 has a scale ranging from 0 to 9.4. DAS and DAS28 values cannot be directly compared.

In some embodiments, the treatment of rheumatoid arthritis by the method may result in the amelioration or improvement of at least one of the symptoms related to rheumatoid arthritis. These symptoms may include, but are not limited to, joint pain, stiffness, tenderness, deformity, and swelling, loss of joint range, rheumatoid nodules, fatigue, and fever. In other embodiments, the method may help to reduce inflammation and damage caused to the affected joint's cartilage and bone. In some embodiments, the method may help to prevent or reduce the disease progression of rheumatoid arthritis.

In some embodiments, the method may result in the mammal having a reduced DAS score as compared to prior to treatment. In other embodiments, the mammal may experience a DAS score reduced by 1, 2, 3, 4, 5, 6, 7, 8, 9, or 10 units. In some embodiments, the method may result in the mammal having a reduced DAS28 score as compared to prior to treatment. In other embodiments, the mammal may experience a DAS28 score reduced by 1, 2, 3, 4, 5, 6, 7, 8, or 9 units.

In some embodiments, the method may be used to treat psoriasis and/or psoriatic arthritis. Psoriasis is a chronic, autoimmune disease caused by the immune system attacking skin cells which then causes abnormally accelerated growth of skin cells. As a result, an unusually high number of old skin cells and white blood cells are pushed to the skin's surface causing itchy patches of red skin and silvery scales and systemic inflammation. Psoriasis often affects the elbows, knees, scalp, lower back, face, palms, feet, fingernails, toenails, and mouth. Psoriasis episodes can be triggered by a number of factors, including infections, medications, injuries, and stress. Types of psoriasis include plaque, guttate, inverse, pustular, and erythrodermic. Psoriasis is typically diagnosed by a dermatologist or other medical professional who considers the patient's medical history and examines the affected skin, scalp, and/or nails. Affected skin may also be examined under a microscope; skin affected by psoriasis generally looks thicker and inflamed as compared to non-affected skin. Psoriasis is also associated with psoriatic arthritis which is an inflammatory-type of arthritis. Psoriatic arthritis can generally affect any joint and can cause soreness, stiffness, swelling, and can lead to joint damage.

The current standard for assessment of extensive psoriasis has been the Psoriasis Area and Severity Index (PASI). The PASI is a measure of the average redness, thickness, and scaliness of the lesions (each graded on a 0-4 scale), weighted by the area of involvement.

In some embodiments, the treatment of psoriasis and/or other conditions associated with psoriasis by the method may result in the amelioration or improvement of at least one of the symptoms related to psoriasis and/or other conditions associated with psoriasis, such as psoriatic arthritis. These symptoms may include, but are not limited to, itchiness, patches of skin, dry cracked skin, pain, pustules, rash, inflammation, hypothermia, dehydration, malnutrition, burning, soreness; thickened, pitted, or ridged nails; leukonychia, subungual hyperkeratosis, loosened nails, nail crumbling, splinter hemorrhage, spotted lunula, onychornycosis, paronychia, hair loss, swollen and/or stiff joints, nail discoloration, joint pain, redness, swelling, reduced range of joint motion, iritis, uveitis, spondylitis, and skin bleeding. In some embodiments, the method may reduce the number and/or duration of psoriatic episodes experienced by the patient.

In some embodiments, the method may be used to treat glomerulonephritis (nephritis). Glomerulonephritis is a condition where the glomeruli of the kidney become inflamed. The glomeruli remove excess fluid, electrolytes, and waste from the bloodstream to be excreted in urine. Glomerulonephritis can be acute, such as from infection or injury, or of gradual/chronic onset. Primary glomerulonephritis occurs without cause from another condition while secondary glomerulonephritis is caused by another disease, such as lupus, diabetes, Goodpasture's syndrome, Wegener's disease, or polyarteritis nodosa. Severe or prolonged inflammation associated with glomerulonephritis can damage the kidneys and lead to kidney failure. Non-proliferative forms of glomerulonephritis include, but are not limited to, Minimal Change Disease (MCD, or Nil Lesions, Nil Disease, or lipoid nephrosis), focal segmental glomerulosclerosis, membranous gomerulonephritis, and thin basement disease. Proliferative forms of glomerulonephritis may include, but are not limited to, IgA nephropathy (Berger's disease), post-infectious glomerulonephritis, membranoproliferative glomerulonephritis, and rapidly progressive glomerulonephritis.

In some embodiments, the treatment of glomerulonephritis by the method may result in the amelioration or improvement of at least one symptom associated with the glomerulonephritis or subsequent kidney dysfunction. These symptoms may include, but are not limited to, edema, swelling, hematuria, proteinuria, decreased urination, increased nighttime urination, darkened urine, abdominal pain, nosebleeds, high blood pressure, foamy urine, decrease/lack of appetite, nausea, vomiting, tiredness, difficulty sleeping/insomnia, dry and itchy skin, nighttime muscle cramps, reduced kidney function, electrolyte imbalances, blood in vomit or stools, cough and shortness of breath, diarrhea, fever, joint or muscle aches, and urinary tract infections (UTIs). In other embodiments, treatment of glomerulonephritis may help to treat or prevent complications due to glomerulonephritis such as, but not limited to, acute kidney failure, chronic kidney failure, congestive heart failure, malignant hypertension, and susceptibility to other infections.

In some embodiments of the method, the patient may show improved kidney function. Improved kidney function may be shown through laboratory tests, such as through urinalysis testing. In other embodiments, the patient may return to what is considered medically normal urinalysis after treatment with the method. In some embodiments, the patient may have creatinine clearance levels of about 75 mL/min to about 150 mL/min for men and about 80 mL/min to about 130 mL/min for women, urine specific gravity of about 1.000 to about 1.050, urine RBC levels of about four RBCs or less per sample, urine osmolality levels of about 50 mOsm/kg and about 1250 mOsm/kg, blood iron levels of about 50 µg/dL to about 170 µg/dL in men and about 35 µg/dL to about 165 µg/dL in women, an albumin level of about 3.0 g/dL to about 5.0 g/dL, an average urea nitrogen level of about 4 mg/dL to about 6 mg/dL or about 5 mg/dL for low protein diets (e.g., about 0.5 g/kg body weight daily protein intake), about 10 mg/dL to about 15 mg/dL or about 12 mg/dL for average protein diets (e.g., about 1 g/kg body weight daily protein intake), or about 20 mg/dL to about 25 mg/dL or about 22 mg/dL for high protein diets (e.g., about 2 g/kg body weight daily protein intake), or a blood creatinine level of about 0.5 to about 1.5 mg/dL.

In some embodiments, the method may be used to treat pulmonary fibrosis. Fibrosis is a condition which general leads to excessive accumulation and deposition of extracellular matrix (ECM), immune components, connective, and/or scar tissue within the body. Fibrosis can lead to scarring, inflammation, or damage and possibly the ultimate failure of the tissue or organ where the fibrosis occurs. In the case of pulmonary fibrosis, the scar tissue accumulates in the lung's air sac walls, thickening the air sac walls, and making it difficult for oxygen to enter the blood. Pulmonary fibrosis is not known to have one specific cause (i.e., idiopathic), however, it may be a secondary condition caused by other exposure. Some risk factors which have been associated with pulmonary fibrosis include cigarette smoking, viral infections, environmental pollutants (e.g., silica, hard metal dusts, bacterial/animal proteins, gas/fumes, asbestos fibers, grain dust, bird and animal droppings, etc.), certain medications, genetics, and gastroesophageal reflux disease (GERD). Certain autoimmune diseases have been associated with the development of pulmonary fibrosis, including, but not limited to, Churg-Strauss syndrome, lupus, polymyositis/dermatomyositis, polyangiitis, rheumatoid arthritis, and scleroderma.

Pulmonary fibrosis is generally diagnosed through evaluation of patient history and physical examination, computerized tomography (CT) scan, removal of lung tissue (biopsy), and pulmonary function tests. Pulmonary functions tests may include spirometry, pulse oximetry, arterial blood gas test, and exercise testing; abnormal pulmonary function may be the result of restriction vital capacity (VC) often with an increased forced expiratory volume in 1 sec ($FEV_1$)/forced vital capacity (FVC) ratio and/or impaired gas exchange (increased alveolar-arterial oxygen gradient ($AaPo_2$) with rest or exercise or decreased diffusing capacity of the lung for carbon monoxide ($DL_{CO}$).

In some embodiments, the treatment of pulmonary fibrosis by the method may result in the amelioration or improvement of at least one symptom associated with pulmonary fibrosis. These symptoms may include, but are not limited to, exertional dyspnea, non-productive/dry cough, shortness of breath, weight loss, low-grade fivers, fatigue, arthralgias, myalgias, fine bibasilar inspiratory crackles (Velcro crackles), digital clubbing, apnea, or pulmonary hypertension. In some embodiments, the treatment of pulmonary fibrosis by the method may result in the amelioration or prevention of at least one complication associated with pulmonary. These complications may include, but are not limited to, heart attack, stroke, pulmonary embolism, respiratory failure, heart failure, or lung infections.

In some embodiments, the patient may show a decrease in existing fibrotic tissue or a decrease in the formation of new fibrotic tissue after treatment with the method. In other embodiments, the patient may have improved lung function after treatment with the method. In some embodiments, the patient may have a FVC and $FEV_1$, which is repeatable to within 0.15 L upon repeat efforts, or if the largest value for either FVC or $FEV_1$ less than 1 L, then the patient may have a repeatability to within 0.1 L of the largest value. In other embodiments, the patient after treatment with the method may have a peripheral capillary oxygen saturation ($SpO_2$) of greater than about 90%, an arterial blood gas test with a partial pressure of oxygen ($PaO_2$) of about 70 mmHg to about 100 mmHg or about 10 kPa to about 13 kPa, a partial pressure of carbon dioxide ($PaCO_2$) of about 30 mmHg to about 50 mmHg, or about 4 kPa to about 6 kPa; a pH of about 7.3 to about 7.5, a bicarbonate ($HCO_3$) level of about 20 mEq/L or mmol/L to about 30 mEq/L or mmol/L, or an oxygen content ($O_2CT$) level of about 20 mL/100 mL of blood to about 25 mL/100 mL of blood or about 6 mmol/L.

In some embodiments, the method may be used to treat an inflammatory bowel disease (IBD). IBD comprises a group of conditions associated with chronic inflammation in the digestive tract. Inflammation is caused by a cell-mediated immune response in the gastrointestinal mucosa which may be caused by genetic predisposition, viral illness, or environmental factor. IBD can include such diseases as ulcerative colitis, Crohn's disease, collagenous colitis, diversion colitis, Behçet's disease, indeterminate colitis, and lymphocytic colitis.

In some embodiments, the treatment of IBD by the method may result in the amelioration or improvement of at least one symptom associated with IBD. These symptoms may include, but are not limited to, diarrhea, rectal bleeding, abdominal pain, urgent need to move bowels, sensation of incomplete evacuation, constipation, cramping, constipation, loss of appetite, fever, weight loss, nausea, vomiting, malaise, fatigue, night sweats, loss of normal menstrual cycle, anemia, ulcers, hematochezia, arthralgias, growth delays or failed sexual maturity in children, arthritis, uveitis, liver disease, bloody stools, perianal disease, abscesses, joint pain, skin rashes, eye pain, or mouth sores. In some embodiments, the treatment of inflammatory bowel disease by the method may result in the amelioration or prevention of at least one complication associated with IBD. These complications may include, but are not limited to, malnutrition, colon cancer, fistulas, strictures, fissures, intestinal rupture, or bowel obstruction. IBD is generally diagnosed through patient history and elimination of other diseases through blood tests (e.g., complete blood cell tests, electrolyte panel, liver function tests, etc.), and endoscopic and imaging procedure.

A compound, composition, or combination disclosed herein as disclosed herein can also be administered to a mammal in combination with other therapeutic compounds to increase the overall therapeutic effect of the treatment. The use of multiple compounds to treat an indication can increase the beneficial effects while reducing the presence of side effects.

Aspects of the present specification may also be described as follows:

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating an autoimmune disease using a RXR agonist disclosed herein, in combination with a thyroid hormone, uses of a RXR agonist disclosed herein and a thyroid hormone to manufacture a medicament to treat an autoimmune disease.

Example 1

Selective RXR Agonist, IRX4204, Exerts its Biological Effects Through RXR Signaling To determine whether a RXR agonist can mediate its effects via RXRα receptor homodimers, RXRβ receptor homodimers, RXRγ receptor homodimers, or any combination thereof, or the corresponding RAR/RXR heterodimers, receptor-mediated transactivation assays were performed. For transactivation assays assessing RXR homodimer signaling, CV-1 cells were transfected with 1) an expression construct including a full length RXRα, RXRβ, or RXRγ; and 2) a rCRBPII/RXRE-tk-Luc reporter construct that included RXR homodimer-specific RXRE/DR1 responsive element linked to a luciferase gene. For transactivation assays assessing RAR/RXR heterodimer signaling, CV-1 cells were transfected with 1) an expression construct comprising a fusion protein including an estrogen receptor (ER) DNA binding domain linked to the ligand binding domain of RARα, RARβ, or RARγ and 2) a ERE-tk-Luc reporter construct that included an estrogen receptor responsive element linked to a luciferase gene. The ER-RAR fusion proteins provided an accurate readout of only the transfected ER-RAR. After transfection, CV-1 cells were treated with RXR agonist IRX4204 at increasing concentrations for 20 hours before measuring luciferase activity. Luciferase activity is expressed as percent of maximal activity obtained using 1 μM RXR agonist IRX4204 for RXRs and 1 μM all-trans-retinoic acid (ATRA) for RARs (Table 1). Data are mean values ±SE from five independent experiments.

TABLE 1

| RXR Agonist Potencies in Activating RXRs and RARs | | | | | | | |
|---|---|---|---|---|---|---|---|
| | | $EC_{50}$ (nM) Efficacy (% of 1 μM IRX4204) | | | $EC_{50}$ (nM) Efficacy (% of 1 μM ATRA) | | |
| Compound | Structure | RXRα | RXRβ | RXRγ | RARα | RARβ | RARγ |
| IRX4204 | | 0.08 ± 0.01 100 | 0.47 ± 0.05 100 | 0.09 ± 0.01 100 | >1,000 | >1,000 | >1,000 |

These results indicate that RXR agonist IRX4204 activated RXR receptors with very high potency ($EC_{50}$<0.5 nM) for all three RXR subtypes (Table 1). In contrast, $EC_{50}$ of the RXR agonist for RARs was >1,000 nM with minimal activity detected at ≥1 μM. This difference represents >2,000-fold selectivity for RXRs over RARs in functional transactivation assays. Additionally, these data demonstrate that RXR agonist IRX4204 was more than 1,000-fold more potent in activating RXR receptors rather than RAR receptors. These results indicate that the biological effects of selective agonists such as IRX4204 are mediated through a RXR signaling pathway and not via a RAR signaling pathway. Also, using appropriate receptor and reporter constructs, RXR agonist IRX4204 was shown not to transactivate so called "permissive RXR heterodimers" PPAR/RXR, FXR/RXR and LXR/RXR (FIGS. 1A-C). In this regard, RXR agonist IRX4204 is distinct from other RXR agonists. Additionally, IRX4204 selectively activates the Nurr1/RXR permissive heterodimer (FIG. 1D). Thus, RXR agonist IRX4204 has a unique profile in that it selectively activates only RXR homodimers and Nurr1/RXR heterodimers.

Example 2

Binding Affinity of RXR Agonists

To determine the binding affinity for a RXR agonist, competitive displacement assays were performed. RXRα, RXRβ, RXRγ, RARα, RARβ, or RARγ were expressed in SF21 cells using a baculovirus expression system and the resulting proteins were purified. To determine the binding affinity for a RXR agonist for an RXR, purified RXRα, RXRβ, and RXRγ were separately incubated with 10 nM [$^3$H]-9CRA, and the binding affinity of the RXR agonist IRX4204 was determined by competitive displacement of [$^3$H]-9CRA from the receptor. To determine the binding affinity for a RXR agonist for an RAR, purified RARα, RARβ, and RARγ were incubated with 5 nM [$^3$H]-ATRA, and the binding affinity of the RXR agonist IRX4204 was determined by competitive displacement of [$^3$H]-ATRA from the receptor. Ki values are mean values of at least two independent experiments (Table 2). Standard errors (±) among independent experiments are indicated.

As shown in Table 2, RXR agonist IRX4204 displayed high affinity for RXRα, RXRβ, and RXRγ with $K_i$ values being 1.7, 16, and 43 nM, respectively. In contrast, the RXR agonist IRX4204 bound with very low affinity to each of the RARs (Ki values being >1,000 nM). These data indicate that IRX4204 is highly selective for the RXRs relative to the RARs.

buffered saline (PBS). Mice were also given 200 ng of pertussis toxin in PBS administered by inter-peritoneal (i.p.) injection on the same day as MOG emulsion injection (day 0) and 2 days later (day 2). Starting on day 7 after immunization, mice were given the RXR agonist IRX4204 (50 μg i.p.), vehicle control (i.p.), thyroxine (T4), or IRX4204+ thyroxine every other day for the duration of the experiment (n=6-7 mice/group). Statistics show the results of a Mann Whitney test (analyzed from start of treatment to the end of the experiment). Mice were scored using the following scale: 0—Mice have no disease, 1—Mice have distal limp tail or rear leg weakness (paresis), 1.5—Mice have distal limp tail and rear leg weakness, 2—Mice have complete limp tail and rear leg weakness, 2.5—Mice have complete limp tail and weakness in both rear legs, 3—Mice have complete limp tail and paralysis in both rear legs, 3.5—Mice have complete limp tail, paralysis in both rear legs, and forelimb weakness. Mice receiving a score of 3.5 were immediately euthanized.

Figure 2:
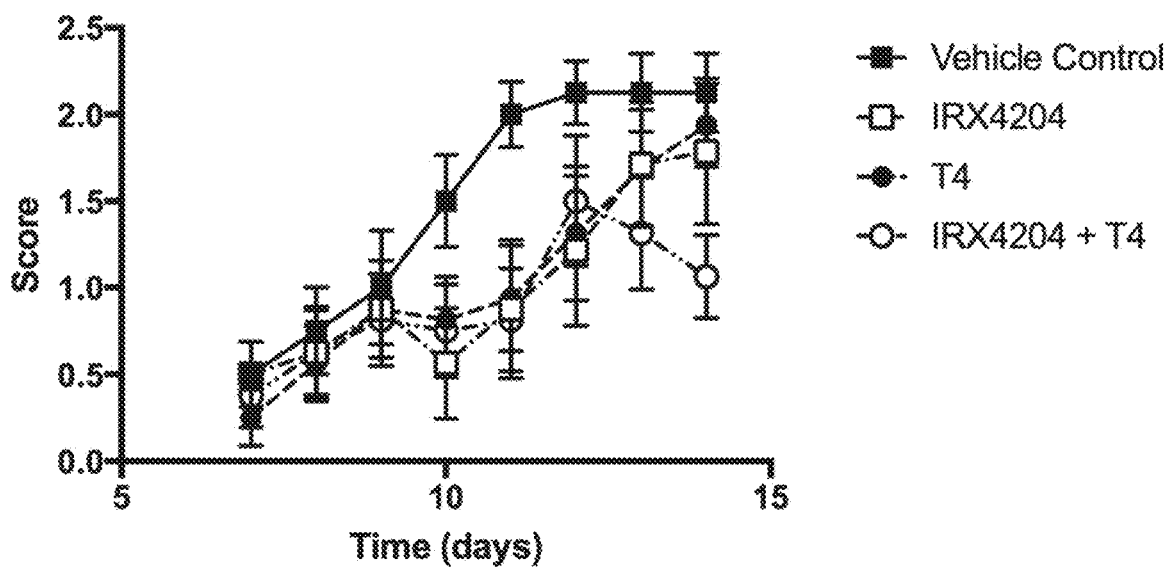
FIG. 2 shows that RXR agonists combined with thyroid hormone attenuate experimental autoimmune encephalomyelitis (EAE) in C57BL/6 mice.

FIG. 2 depicts scores of disease severity over time. The results indicate that administration of the RXR agonist IRX4204 at 50 μg significantly reduces the symptoms of EAE in mice. Efficacy of the RXR agonist was observed after the first administration (day 7) and maintained throughout the course of the study (day 20). However, the combination of IRX4204 and thyroxine reduced the symptoms of EAE in mice to an even greater degree (FIG. 2).

A dose titration experiment was also conducted in EAE mice. EAE was induced in 28 B6 mice with MOG/CFA and PT as above. Mice were scored on day 7 as indicated above and divided into groups by score so means are as equal as possible. Starting day 8, mice were scored and injected with a vehicle control or IRX4204 (50 μg, 100 μg, or 200 μg) every day.

TABLE 2

RXR Agonist Binding Affinities

| Compound | Structure | RXR Binding Affinity Ki (nM) | | | RAR Binding Affinity Ki (nM) | | |
|---|---|---|---|---|---|---|---|
| | | RXRα | RXRβ | RXRγ | RXRα | RXRβ | RXRγ |
| IRX4204 | 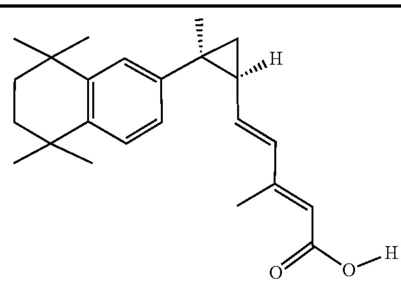 | 1.7 ± 0.1 | 16 ± 1.0 | 43 ± 3.0 | 6344 ± 674 | 7552 ± 638 | 4742 ± 405 |

Example 3

RXR Agonists Attenuate EAE in B6 Mice

Figure 7:
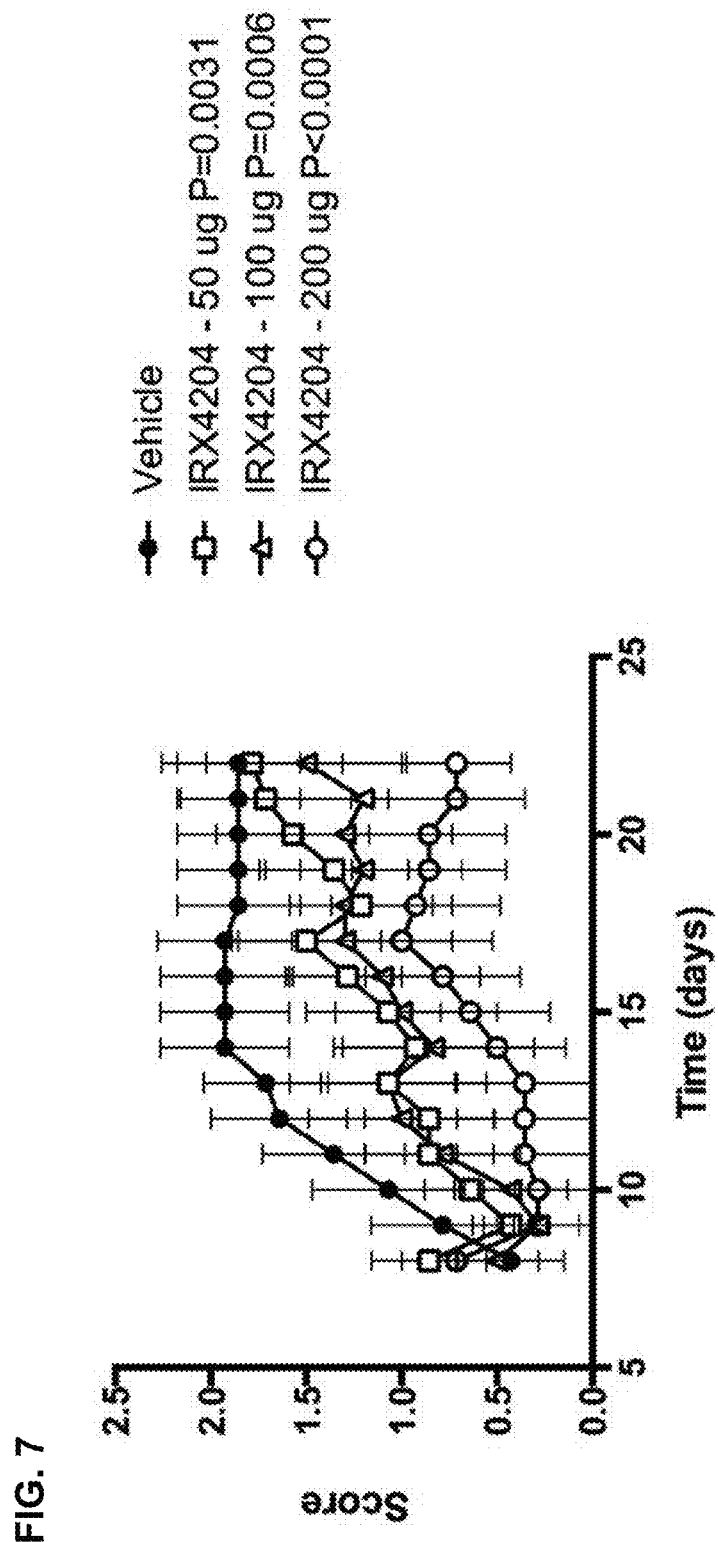
FIG. 7 depicts effects of selective RXR agonist IRX4204 on EAE in mice.

To determine whether a RXR agonist can attenuate multiple sclerosis, C57BL/6 (B6) mice were immunized (day 0) to induce experimental autoimmune encephalomyelitis (EAE) by subcutaneous (s.c.) injection at the base of their spine with 200 μL of adjuvant containing 125 μg myelin oligodendrocyte glycoprotein peptide (35-55) (MOG peptide; Peptides International, Louisville, Ky.) and 400 μg non-viable M. tuberculosis H37 desiccate emulsified in a mixture of incomplete Freund's adjuvant and phosphate The mice were weighed at the beginning of experiment and every day they had a score of 2.5 or higher and mice were euthanized if they lost 15% or more of their start weight. All mice that were treated with IRX4204 had significantly less disease overall (FIG. 7). At the completion of the experiment, the vehicle control and 200 μg/day groups were euthanized and spleen and CNS samples obtained.

Figure 8A:
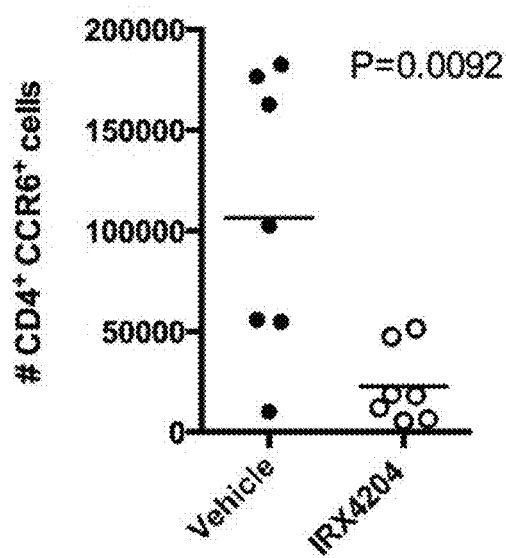
FIGS. 8A-B depicts expression of CCR6 (FIG. 8A) and CD49d (FIG. 8B) on splenocytes from EAE mice treated with 200 µg/day of IRX4204 or control.
Figure 8B:
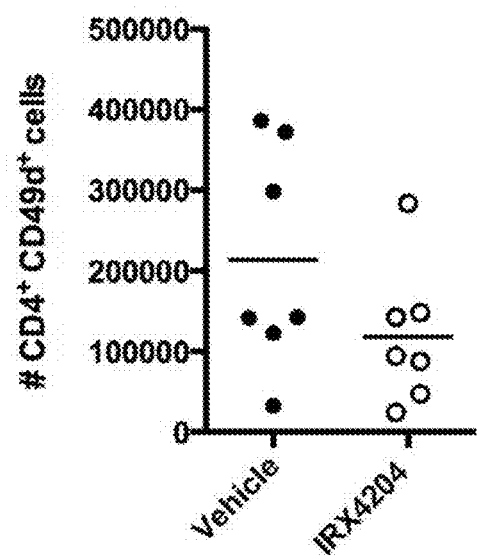
Figure 9A:
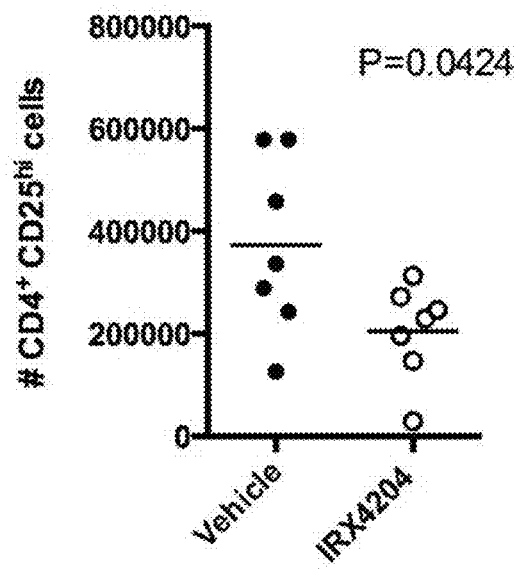
FIGS. 9A-D depicts quantification (FIG. 9A) and frequency (FIG. 9B) of CD4+CD25hi cells, total number of effector and memory CD4 T cells (FIG. 9C), and total number of activated CD4 T cells (FIG. 9D) in splenocytes from EAE mice treated with 200 µg/day of IRX4204 or control.
Figure 9B:
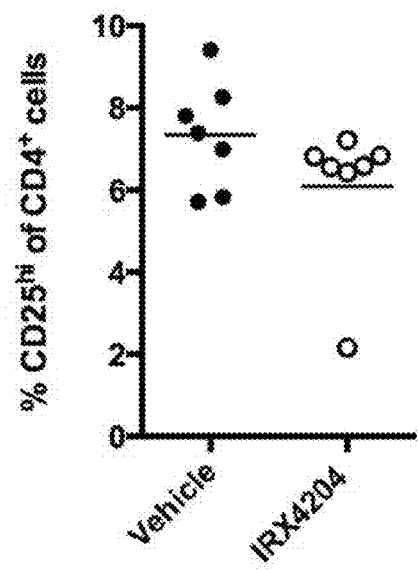
Figure 9C:
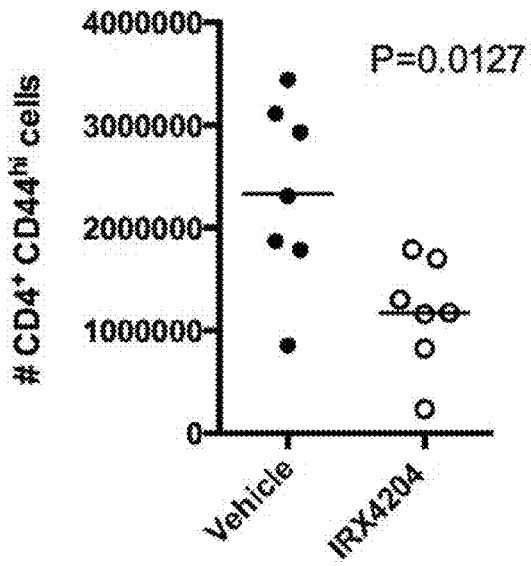

The spleen samples were evaluated for CD49d (FIG. 8A) and CCR6 (FIG. 8B), and IRX4204 treatment lowered CCR6, but not CD49d, expression on CD4 T cells. Additionally, CD4+ CD25hi cells (generally consisting of TReg) were reduced, although the frequency was not altered (FIGS. 9A and 9B). The total number of effector and memory CD4

Figure 9D:
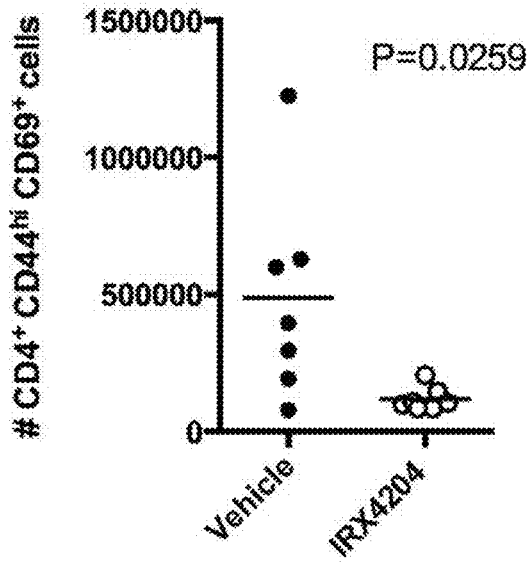

T cells, as indicated by CD44 expression, decreased with IRX4204 treatment (FIG. 12C) and the total number of recently activated CD4 T cells, as indicated by expression of both CD69 and CD44, was also decreased with IRX4204 treatment (FIG. 9D).

Figure 10:
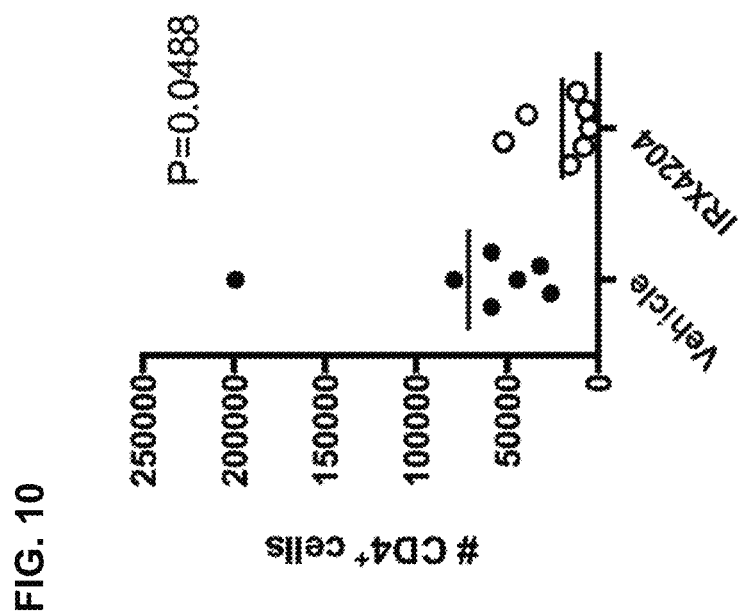
FIG. 10 depicts the total number of infiltrating CD4 T cells in the CNS of EAE mice treated with 200 µg/day of IRX4204 or control.

In the CNS, the total the total number of infiltrating CD4 T cells was reduced with IRX4204 treatment (FIG. 10). Restimulation with PMA/Ionomycin was used to help detect the cytokine production. Both IFNγ (FIGS. 11A and 11B) and TNF (FIGS. 11C and 11D) were significantly reduced with treatment. Co-expression of IFNγ and IL-17A by CD4 T cells in CNS was quantified, but was not significantly different between groups (FIG. 12A-12C).

Example 4

RXR Agonist-Treated Mice have Reduced Central Nervous System Infiltrating Cells

To determine whether a RXR agonist can reduce central nervous system (CNS) infiltrating cells, C57BL/6 (B6) mice were treated as described in Example 6. On day 20 after immunization, mice were sacrificed and perfused with phosphate buffered saline (PBS). Brain and spinal cord tissue was isolated, digested with DNase and Liberase DL (Roche Diagnostics, Indianapolis, Ind.) for 30 minutes, and homogenized through 70 micron nylon mesh filters. Resulting cells were placed over a Percoll gradient to remove myelin. The remaining cells (microglia and CNS infiltrating cells) were counted, stained for molecules of interest, and run on a flow cytometer. Based on the frequencies obtained by FACS of these cell populations, total cell numbers of CNS infiltrating leukocytes expressing CD45, including CD4$^+$ T cells and CD11c$^+$ CD11b$^+$ myeloid dendritic cells (DC), were calculated.

Figure 3A:
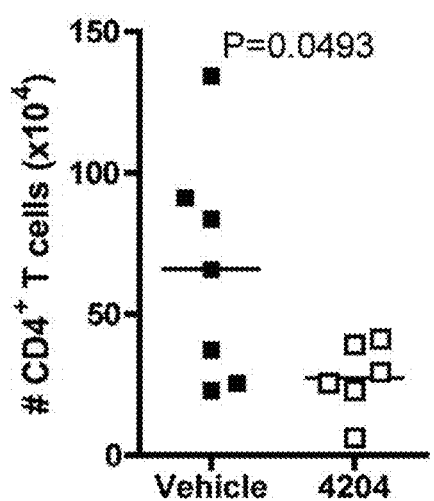
FIGS. 3A-B shows that RXR agonists reduce leukocyte infiltration into the central nervous system.
Figure 3B:
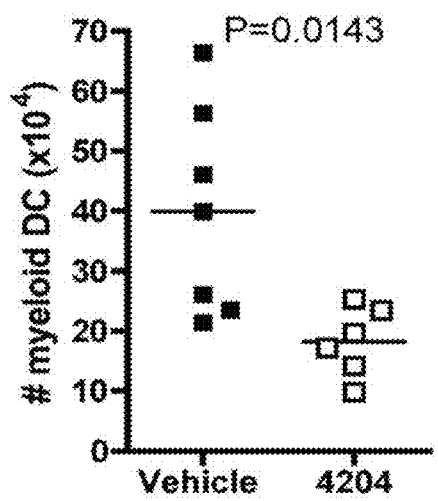

FIG. 3 compares the number of CD4$^+$ cells or CD11c$^+$ CD11b$^+$ cells (myeloid DC) in mice treated with the RXR agonist 194204 verses the vehicle control. There was a significant reduction in the infiltration of both CD4$^+$ cells and CD11c$^+$ CD11b$^+$ cells in animals treated with a RXR agonist as compared to the control. As disease is propagated in the CNS through the CD4$^+$ cells infiltrating the CNS and becoming re-activated by CD11c$^+$ CD11b$^+$ cells, this suggests that part of the mechanism of action in this model is to limit the presence of the cells in the CNS.

Example 5

RXR Agonists Attenuate EAE in SJL Mice

To determine whether a RXR agonist can attenuate multiple sclerosis, SJL mice were immunized to induce EAE by s.c. injection at the base of their spine with 200 μL of adjuvant containing 200 μg proteolipid proteins (139-151) (PLP peptide; Peptides International, Louisville, Ky.) and 400 μg of non-viable *M. tuberculosis* H37 desiccate emulsified in a mixture of incomplete Freund's adjuvant and PBS. Mice were also given 150 ng of pertussis toxin in PBS i.p. on the same day as PLP emulsion injection and 2 days later. Starting day 7 after immunization, mice were given the RXR agonist IRX4204 (50 μg) or vehicle control i.p. every other day for the duration of the experiment (n=6 mice/group). Mice were scored using the scale described in Example 3.

Figure 4:
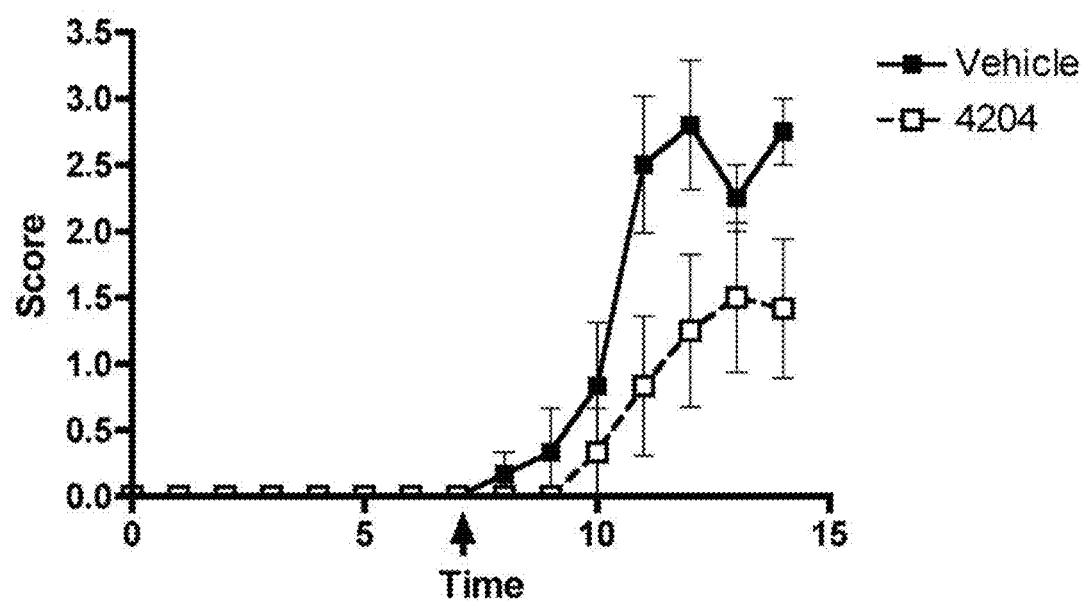
FIG. 4 shows RXR agonists attenuate EAE in SJL mice.
Figure 5A:
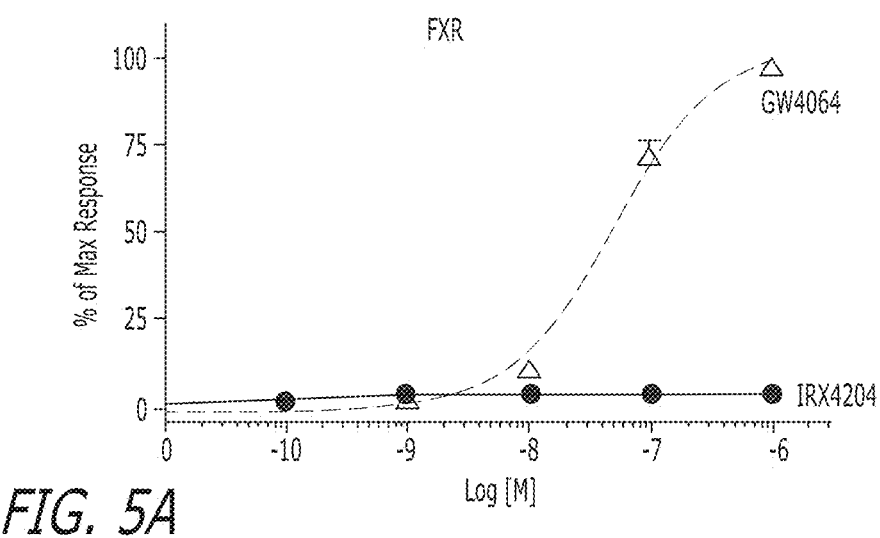
FIGS. 5A-D shows that IRX4204 selectively activates RXR-Nurr1 heterodimers. Transactivation assay of IRX4204 (194204, Formula III) for farnesoid X receptor FXR (FIG. 5A); for liver X receptors LXRα and LXRβ (FIG. 5B); for peroxisome proliferator-activated receptor PPARγ (FIG. 5C); and for Nurr1 receptor in the presence or absence of RXR (FIG. 5D).
Figure 5B:
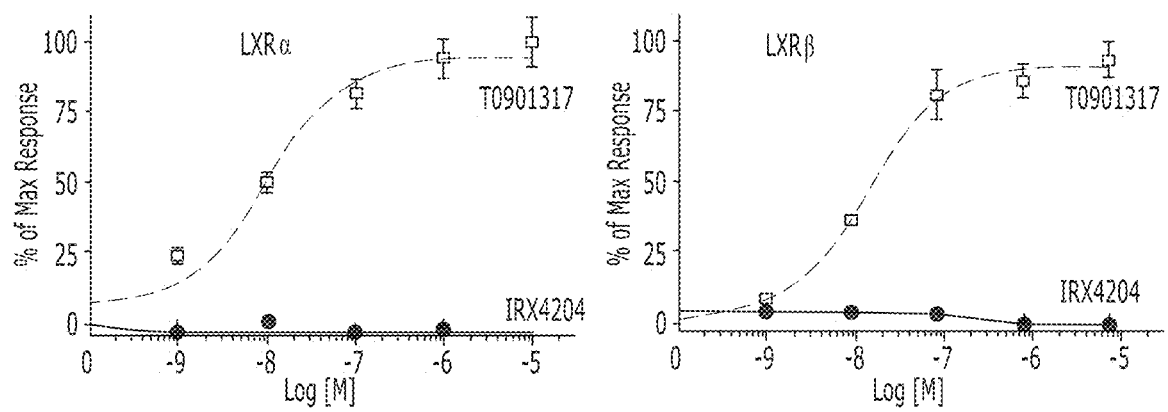
Figure 5C:
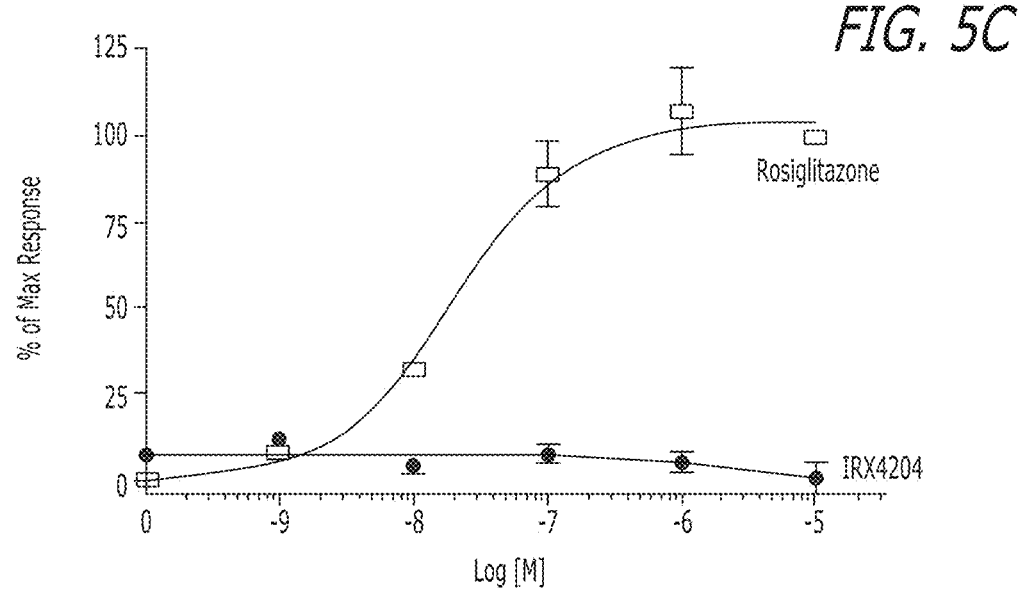
Figure 5D:
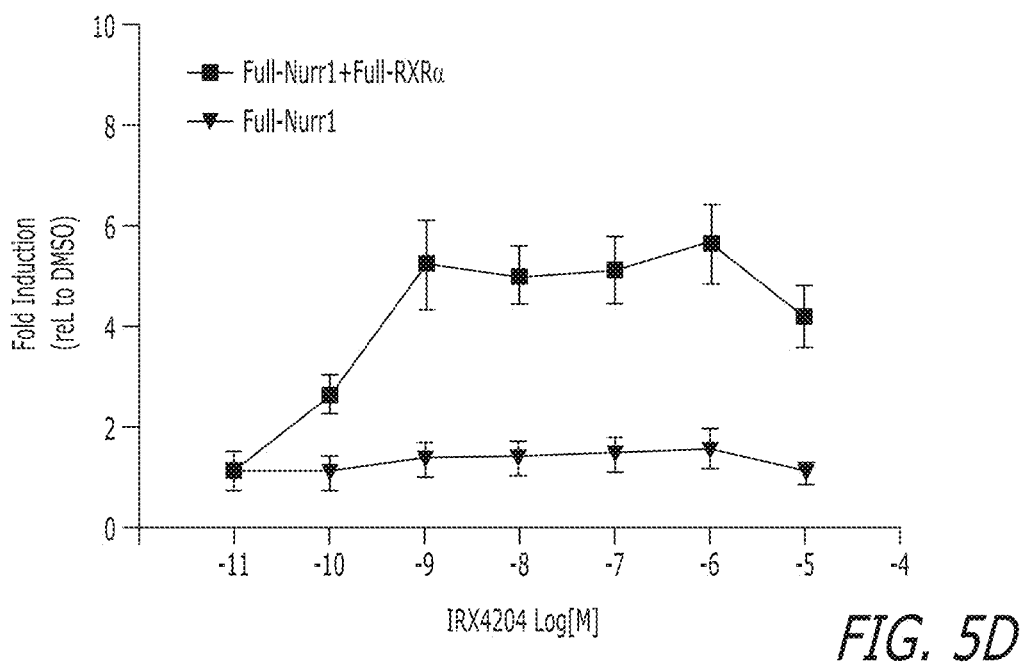

The results indicate that administration of the RXR agonist IRX4204 significantly reduces the symptoms of EAE in mice. Table 3 shows the features of a RXR agonist IRX4204 treatment in SLJ mice. FIG. 4 depicts scores of disease severity over time. Efficacy of the RXR agonist was observed after the second administration (day 8) and maintained throughout the course of the study (day 14). It is expected that if administration of IRX4204 was combined with thyroxine treatment, there would be a further reduction in the symptoms of EAE and disease severity scores.

TABLE 3

RXR agonist treatment in SJL mice

| Clinical Features | Vehicle | IRX4204 |
| --- | --- | --- |
| Mean Maximum Score | 3.2 ± 0.6 | 1.5 ± 1.4 |
| Disease Incidence | 6/6 | 4/6 |
| Death from Disease | 4/6 | 0/6 |

Example 6

RXR Agonist IRX4204 as a Selective Activator of Nurr1/RXR Permissive Heterodimer In order to determine which permissive RXR heterodimer is activated by the RXR agonist IRX4204, receptor trans-activation assays were carried out as follows for PPARγ/RXR, FXR/RXR, LXRα/RXR, LXRβ/RXR, and Nurr1/RXR. For PPARγ: CV-1 cells were transfected with 3×(rAOX/DR1)-tk-Luc reporter gene and an expression vector for PPARγ. For FXR:CV-1 cells were transfected with 3×(IBABP/IRI)-tk-Luc reporter gene and vectors for FXR and RXRα. For LXR:CV-1 cells were transfected with 3×(PLTP/LXRE)-tk-Luc reporter gene with vectors for LXRα or LXRβ. For Nurr1: COS7 cells were transfected with 3×NBRE-tk-luc reporter gene and full length Nurr-1 with or without full-length RXRα plasmid. Cells were then treated with vehicle or IRX4204 for 20 hr. Luciferase data were normalized to co-transfected β-gal activity. Luciferase activity was expressed as percent of maximal activity obtained using specific agonists. Rosiglitazone (PPARγ), GW4064 (FXR), T0901317 (LXR). The data indicate that IRX4204 does not activate FXR/RXR (FIG. 2A), LXRα/RXR or LXRβ/RXR (FIG. 2B), or PPARγ/RXR (FIG. 2C). In contrast, IRX4204 potently (EC$_{50}$<1 nm) activates the Nurr1/RXR heterodimer (FIG. 2D). These data collectively indicate that IRX4204 is a unique RXR agonist in that it selectively activates the Nurr1/RXR heterodimer but not the PPARγ/RXR, FXR/RXR or LXR/RXR heterodimers.

Example 7

Effect of RXR Agonists on Oligodendrocyte Precursor Cell Differentiation

Figure 6:
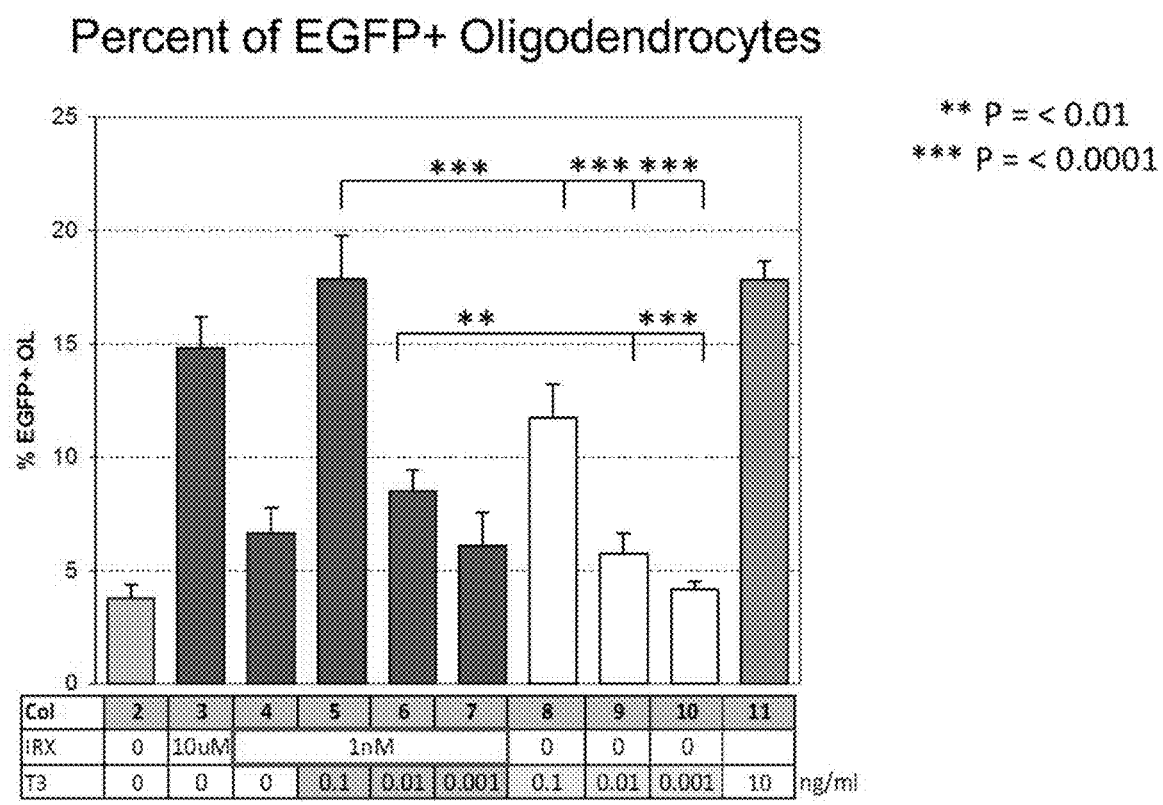
FIG. 6 shows the percentage of green fluorescent protein (EGFP) positive oligodendrocytes after culture of oligodendrocyte precursor cells derived from embryonic mouse brains with IRX4204 and thyroid hormone.

The goal of this study was to evaluate the effect of IRX4204 on differentiation of oligodendrocyte precursor cells (OPCs) into oligodendrocytes. OPCs were generated from a neurosphere culture of E14.5 PLP-EGFP (on C57BL/6J background) mouse brains. The isolated OPCs were treated with IRX4204 and/or T3 to evaluate the expression of green fluorescent protein (EGFP), which correlates with differentiation of OPCs into oligodendrocytes. The EGFP expressing cells were quantified with Cellomics Neuronal Profiling Algorithm. The positive (T3) control demonstrated differentiation of OPCs as expected. The results demonstrate that IRX4204 promotes OPC differentiation into oligodendrocytes as shown by the increase in the number of the EGFP positive cells compared to negative control (DMSO). All tested concentrations showed a significant increase in OPC differentiation into oligodendrocytes (FIG. 6). However, addition of T3 to the IRX4204-treated cultures induced even higher levels of EGFP+ oligodendrocytes demonstrating the significant benefit of the combination of IRX4204 and thyroid hormone.

The EGFP expressing cells in controls and all compounds were quantified with Cellomics Neuronal Profiling Algorithm. The experiment was successful as demonstrated by the significant increase in % EGFP cells in positive control (T3; 8.5%) compared to the negative control (DMSO 2.3%). IRX4204 promotes OPC differentiation into oligodendrocytes as demonstrated by the dose dependent increase in the number of the EGFP positive cells compared to negative control (DMSO). IRX4204 did not show any differences in total cell number and pyknotic cells compared to controls. The results from this study demonstrate that IRX4204 promotes OPC differentiation. The data show a dose-dependent increase in the percentage of EGFP cells compared to the negative control. These date indicate that IRX4204 promotes the growth of myelin-forming cells in cell culture.

Example 8

IRX4204 Enhances Central Nervous System (CNS) Remyelination in an In Vivo Model by Acting Directly on the Remyelination Process A focal toxin (ethidium bromide) induced rat model of demyelination is used to ascertain the direct effects of IRX4204 on acute demyelination independent of the immunomodulatory effects of IRX4204. The experiment uses rats of relatively advanced age (1 year) since such rats undergo remyelination in a less efficient manner, thereby providing data that are more relevant to the clinical treatment of human patients with multiple sclerosis or other demyelination disorders.

Focal demyelination is induced in one year old rats (approximately 300 g in weight) by injecting stereotactically 5 µl of ethidium bromide solution (0.01% vol/vol in saline) in a bilateral manner into the caudal cerebellar peduncles (CCP). Starting seven days after injection of the ethidium bromide, the rats are treated by oral gavage for fourteen days (day 7 to day 21 post-ethidium bromide treatment) with 10 mg/kg/day of IRX4204 (in DMSO and corn oil), or the same dose of oral IRX4204 plus 20 ng/g of subcutaneous thyroxine, or vehicles (DMSO and corn oil plus thyroxine vehicle) for fourteen days. The rats are killed on day 24 post-ethidium bromide treatment for analysis of remyelination by quantitative polymerase chain reaction (qPCR) and microscopy.

Analysis of the lesions revealed the following: the densities of Olig2+ oligodendrocyte lineage cells and CC1+ differentiated oligodendrocytes increased in IRX4204-treated animals relative to vehicle treated animals and increased further in the IRX4204 plus thyroxine animals; Nkx2.2+oligodendrocyte precursor cells (OPCs) increased in IRX4204-treated lesions relative to vehicle treated lesions and were highest in IRX4204 plus thyroxine treated lesions. Also, real-time qPCR analysis of lesion samples show an increase in Mbp expression and an increase in Pdgfra expression indicating higher levels of myelin regeneration in IRX4204-treated animals with highest levels of Mbp and Pdgfra expression seen in IRX4204 plus thyroxine animals. Ultrastructural analyses of CCP lesions further demonstrate that IRX4204 plus thyroxine treatment results in more remyelinated axons in animals than IRX4204 only treatment which in turn leads to more remyelinated axons than vehicle treatment. AG-ratio analysis (this ratio is that of axon diameter to myelinated axon) also shows that IRX4204-treated animals have a lower G-ratio than vehicle treated animals and that this lower ratio is due to the formation of thicker remyelinated sheaths surrounding axons in IRX4204-treated animals. The G-ratio was further reduced in animals treated with the combination of IRX4204 and thyroxine. All these findings are consistent with an increase in CNS remyelination in IRX4204-treated animals and an optimal increase in IRX4204 plus thyroxine treated animals.

Example 9

IRX4204 in Combination with Thyroid Hormone Accelerates Remyelination in the Cuprizone/Rapamycin Mouse Model of Toxic Demyelination The cuprizone (bis-cyclohexanone oxaldihydrazone) model facilitates reliable, reproducible and unequivocal analysis of myelin parameters in both white and grey matter. The cuprizone model is a model for toxic demyelination. In this model, young mice are fed with the copper chelator cuprizone, leading to oligodendrocyte death and a subsequent reversible demyelination. Cuprizone-fed mice with rapamycin, a drug that blocks mTOR and spontaneous remyelination, allows for better quantification of oligodendrocyte turnover. In the acute cuprizone paradigm, male C57BL/6 mice at 6 to 9 weeks of age are fed a diet of chow mixed with 0.2% cuprizone over the course of 6 weeks. By the third week of cuprizone feeding, consistent demyelination can be observed in the corpus callosum, the largest white matter tract in the mouse brain. Demyelination reaches a maximum at 5 or 6 weeks. Chronic demyelination can be induced if C57BL/6 mice are maintained on a diet with cuprizone for 12 weeks.

The goal of this study was to evaluate the remyelination potential of IRX4204 in a mouse model of toxic demyelination. Previous studies have demonstrated efficacy of IRX4204 in an EAE model of MS. Also, previous data demonstrates that IRX4204 can induce significant oligodendrocyte precursor cell (OPC) differentiation in vitro. The current study is conducted to further investigate the CNS effects of IRX4204 in a cuprizone model of MS on remyelination and neuroprotection.

The animals (8 week-old male C57BL/6J mice) were subjected to cuprizone diet plus rapamycin injections (CR, 10 mg/kg)) for 12 weeks to induce demyelination in white matter (CC, corpus callosum). After 12 weeks, CR was discontinued and subsets of animals were treated daily for 6 weeks with either vehicle (oral IRX4204 vehicle) or IRX4204 (10 mg/kg, PO). All animals were sacrificed after 12 weeks of CR or after further 6 weeks of treatment to evaluate myelin in white matter (corpus callosum) and gray matter (hippocampus and cortex). In addition, the size of myelinated axons was quantified and the large myelinated axons were further assessed by 3D-electron microscopy (3D-EM).

Demyelinating diseases, such as MS, are characterized by myelin loss, chronic inflammation, and axonal and oligodendrocyte loss in the CNS. Although the etiology of MS remains unknown, the disease generally starts with sporadic, acute episodes and develops over time into a chronic and progressive state. The acute and chronic demyelinated lesions of MS can be demonstrated in cuprizone-diet induced mouse models that depend for severity upon the duration of cuprizone administration. Cuprizone induces extensive demyelination in adult mouse brain and simultaneous administration of rapamycin blocks the differentiation of oligodendrocytes and prevents spontaneous remyelination during the demyelination phase. This model also demonstrates the hippocampal demyelination in MS. When cuprizone+rapamycin (CR) is discontinued, there is quantifiable spontaneous remyelination in this model, which can be modified by drug intervention in the remyelination process. The 12-week CR model of demyelination provides an opportunity to evaluate the therapeutic potential of new drugs to promote remyelination in the mouse brain.

A total of 40 animals were included in the study, where all 40 animals received CR demyelination for 12 weeks. After demyelination, a subset (n=10) of animals are sacrificed to serve as controls to assess baseline demyelination. The remaining animals are divided into groups (n=15) which are treated daily with oral IRX4204 (10 mg/kg) or oral vehicle for IRX4204 for six weeks.

There was no significant difference in any of the groups with regard to body weight.

Figure 16A:
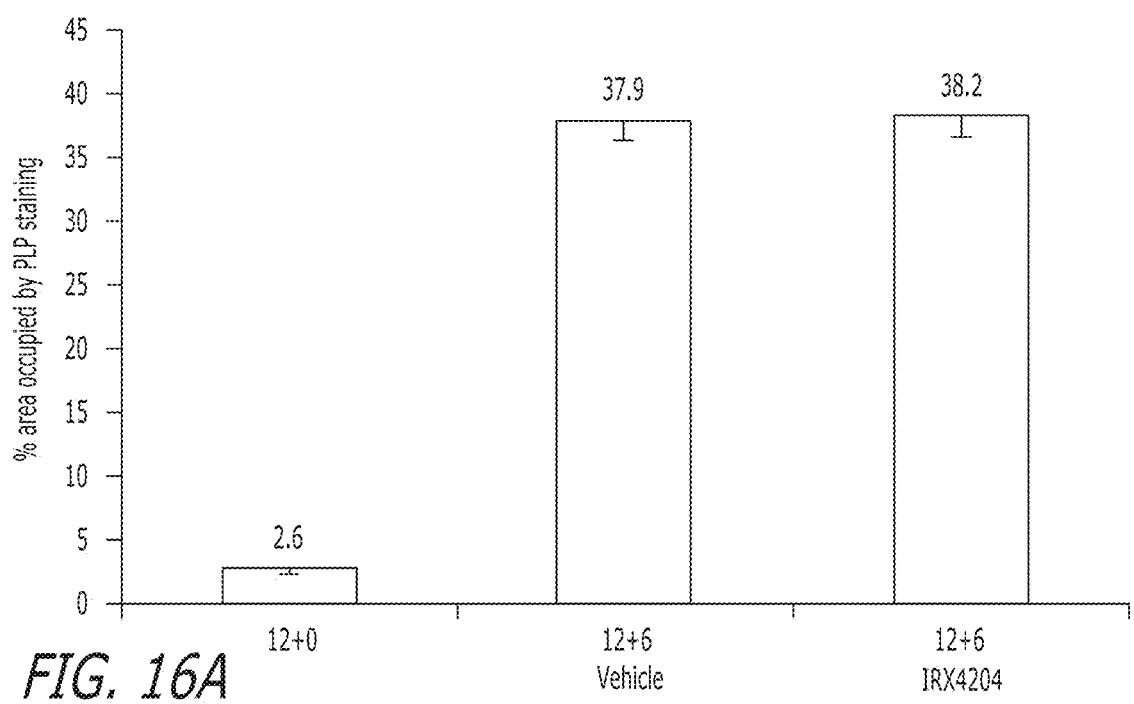
FIGS. 16A-B depicts the effect of IRX4204 on remyelination in a cuprizone-induced demyelination model.
Figure 16B:
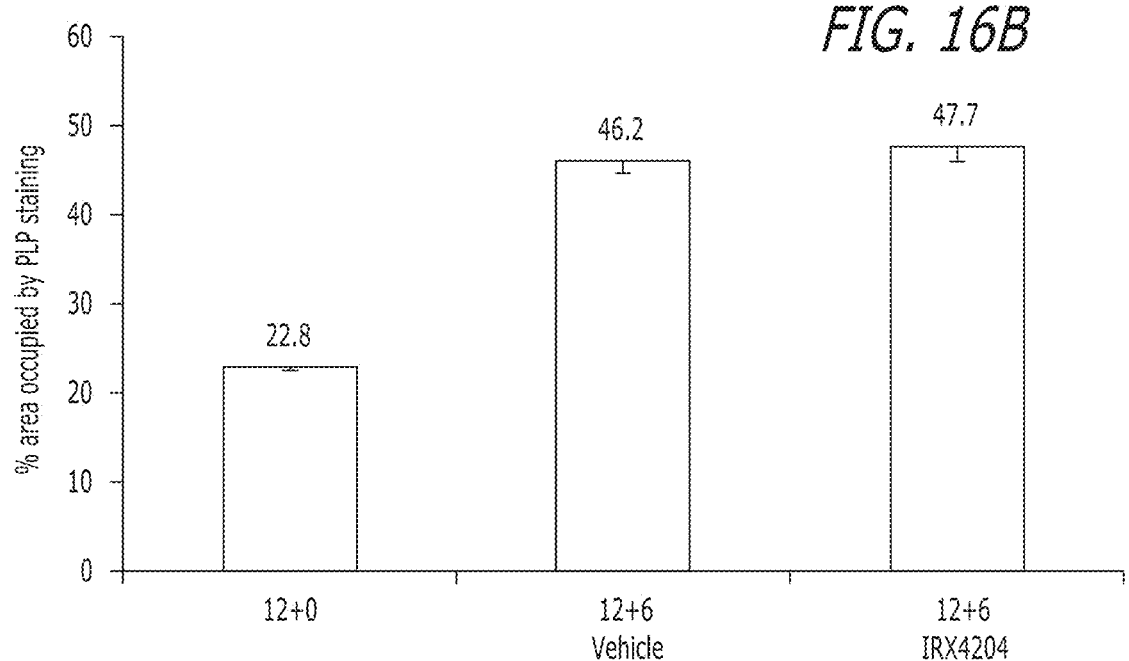

Floating brain sections are immunostained with myelin prolipid protein (PLP) to visualize and quantify myelin in gray matter, hippocampus (FIG. 16A) and cortex (FIG. 16B). The percentage area covered by PLP staining in animals treated with vehicles only after discontinuation of the demyelination regimen is significantly greater than in animals who were sacrificed immediately after CR demyelination demonstrating the occurrence of spontaneous remyelination.

Figure 17A:
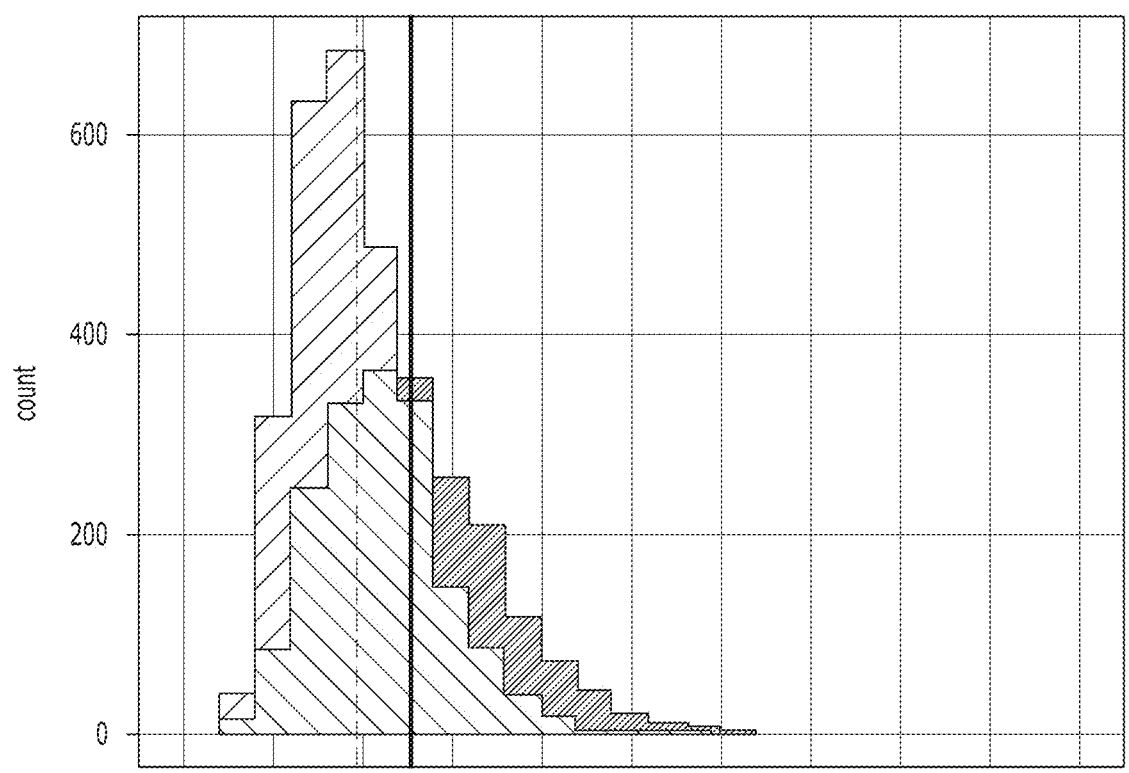
FIGS. 17A-B depicts quantitation of the size of myelinated axons. The size of myelinated axons after 6 weeks of treatment were quantified by Image J. Histogram of axon size distribution demonstrates a shift in distribution to larger axon diameter in IRX4204-treated axons (FIG. 17A). Examination of the 3rd quartile date of axons about 0.7 µm demonstrates a significant increase (P<0.0001) in the size of axons in the upper quartile (FIG. 17B).
Figure 17B:
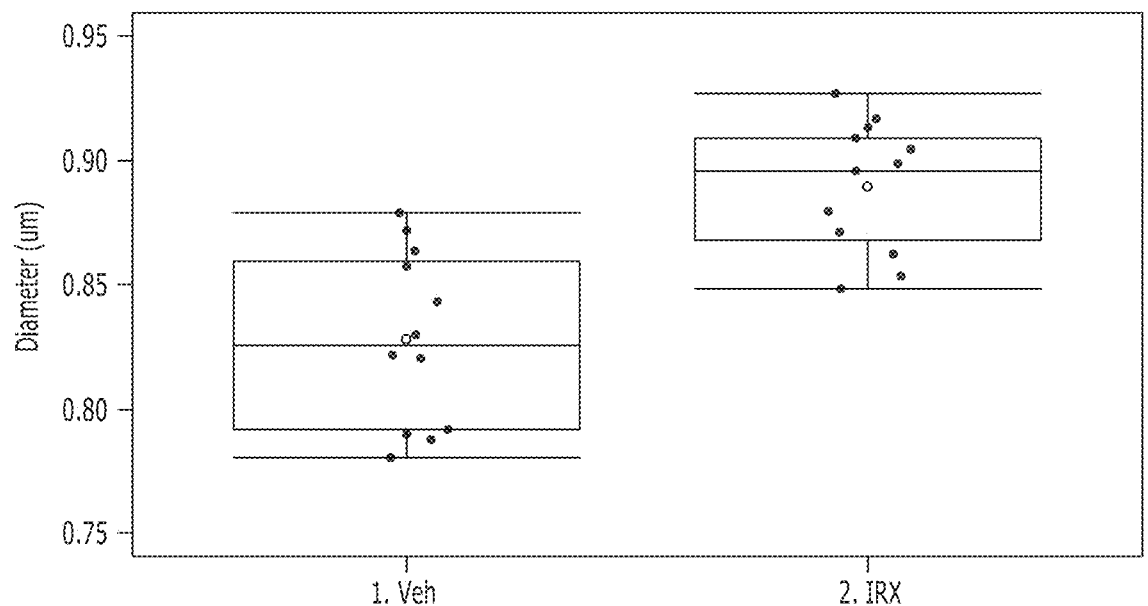
Figure 18:
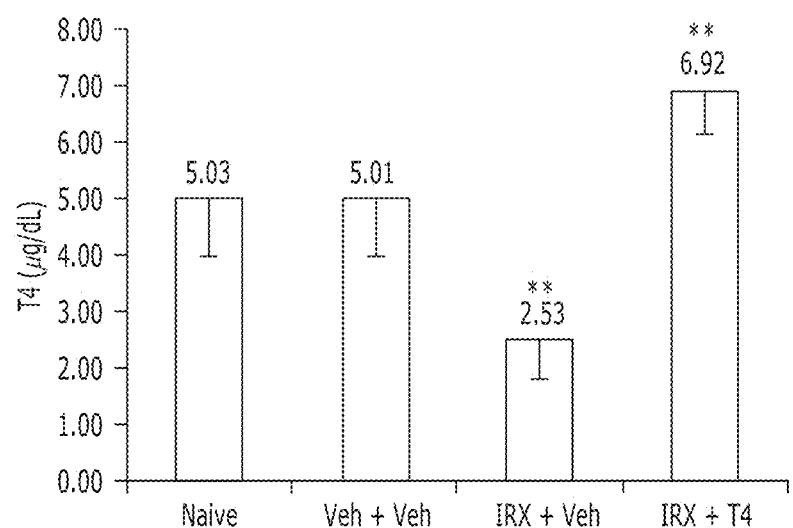
FIG. 18 depicts terminal circulating serum T4 levels in animals that received vehicle, IRX4204, or IRX4204 and T4 (**P<0.005 vs vehicle and naïve control).

In this study, the 12-week demyelination model is used to assess CNS effects of IRX4204, with and without thyroid hormone supplementation, following 6-weeks of treatment. The results from this study demonstrate that IRX4204 significantly increases the size of myelinated axons in the corpus callosum (FIG. 17). In addition, these large myelinated fibers demonstrate a healthy phenotype. Thus, IRX4204 and has a neuroprotective effect on myelinated neurons.

Additionally, IRX4204 plus thyroxine increases the number and density of myelinated axons in white and gray matter in addition to increasing the size of myelinated axons in the corpus callosum.

Example 10

Figure 19:
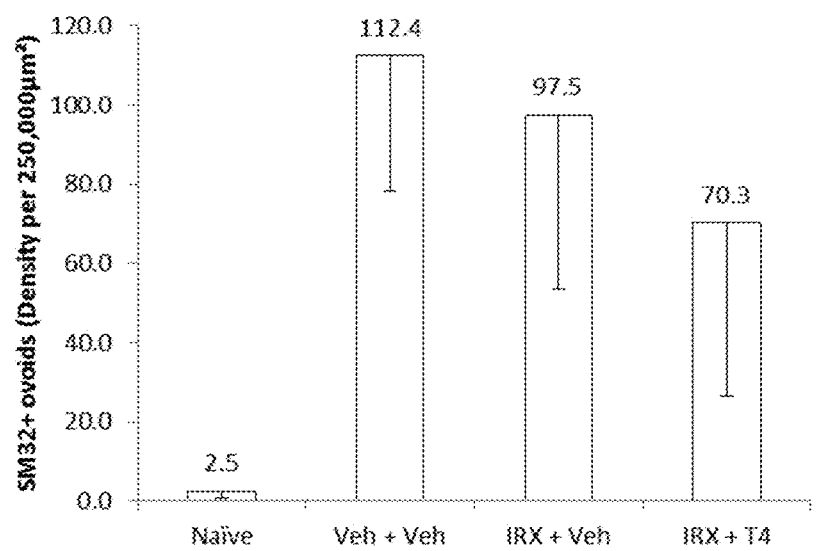
FIG. 19 depicts a quantification of SMI32 positive ovoids in corpus callosum in animals that received vehicle, IRX4204, or IRX4204 and T4 for 6 weeks (*P<0.05 vs Veh+Veh Control).

Evaluation of the Neuroprotective Potential of IRX4204 and IRX4204+Thyroxine in a Mouse Model of Non-Immune Mediated Demyelination The modified cuprizone model (cuprizone+rapamycin) facilitates reliable, reproducible and unequivocal analysis of neurodegeneration caused by demyelination. SMI-32 immunostaining enables the visualization and quantification of swollen and transected axons (ovoids) in the corpus callosum and enables the assessment of the extent of axonal degeneration. There were four groups of mice in the study: cuprizone+rapamycin (CR) only (n=6), CR+vehicles (n=12), CR+IRX4204 (n=12), and CR+IRX4204+thyroxine (n=12). The test articles were administered concurrently with CR for 6 weeks. IRX4204 was administered orally once daily at 10 mg/kg body weight. Thyroxine (T4) treatment was initiated one day after initiation of the IRX4204 treatment. T4 was administered subcutaneously (SC) once daily at 20 ng/g body weight. The CR+vehicles group received the IRX4204 vehicle (oral) and the T4 vehicle (SC). All animals were subjected to terminal blood collection to determine plasma T4 levels. After sacrifice, the density of SMI-32 positive ovoids per unit area was determined for each group. The higher the SMI-32 positive ovoid density, the greater the extent of axonal degeneration. There was a 13.3% reduction in SMI-32+ovoids in the IRX4204 group relative to the vehicles group indicating some neuroprotection by IRX4204 alone. However, the IRX4204+thyroxine group gave a 37.5% reduction relative to the vehicles group indicating that the IRX4204 plus thyroxine combination provides a substantial degree of neuroprotection from the CR-induced neurotoxicity by inhibition of axonal transection in the corpus callosum (FIG. 19).

Example 11

RXR Agonists Regulate T Cell Differentiation

Figure 21B:
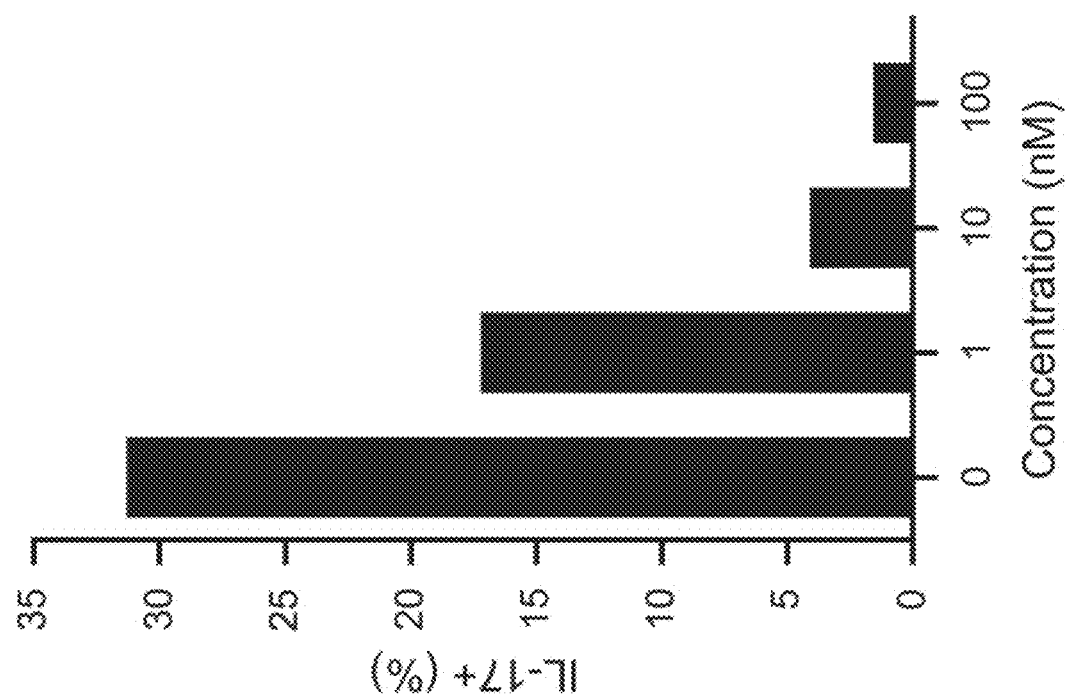
FIGS. 21A-B depicts that RXR agonists increase Treg differentiation under Th17 conditions (FIG. 21A) and inhibit Th17 differentiation under Th17 conditions (FIG. 21B).
Figure 21A:
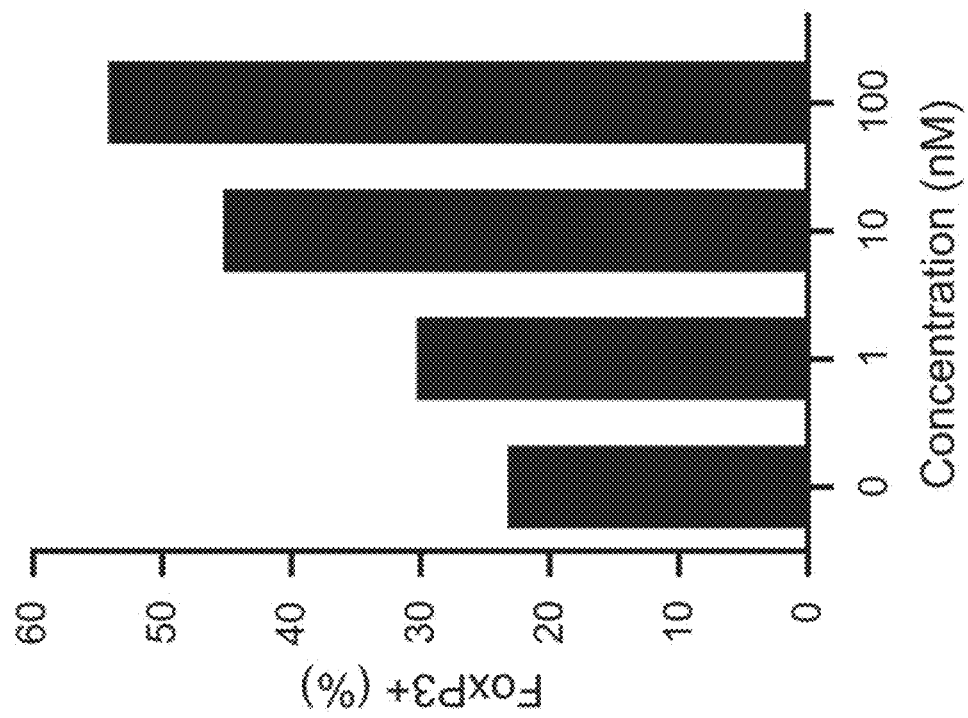

To determine whether a RXR agonist can regulate T cell differentiation, the ability of an RXR agonist to promote Treg cell differentiation and inhibit Th17 cell differentiation under Th17 cell differentiation conditions was assessed by monitoring Foxp3 and IL-17A expression. Naive $CD4^+$ $CD25^-$ $FoxP3^-$ cells were purified from a Foxp3-GFP mouse using flow cytometry by sorting and isolating based upon a $GFP^-$ phenotype. These cells were then cultured under Th17 cell differentiation conditions in media with 0 nM, 1 nM, 10 nM, and 100 nM of RXR agonist IRX4204 (194204) and the expression of Foxp3 and IL-17A was analyzed. The results indicated that as the concentration of the RXR agonist increased, Foxp3 expression increased, indicating an increased presence of Treg cells (FIG. 21A). Additionally, the data demonstrate that as the concentration of the RXR agonist increased, IL-17A expression decreased, indicating a decreased presence of Th17 cells (FIG. 21B). These results indicate that RXR agonists regulate T cell differentiation by promoting differentiation of immunosuppressive Treg cells and concurrently inhibiting differentiation of inflammatory Th17 cells from naïve T cells in vitro.

Example 12

RXR Agonists Regulate T Cell Differentiation Independent of RAR Signaling

Figure 22:
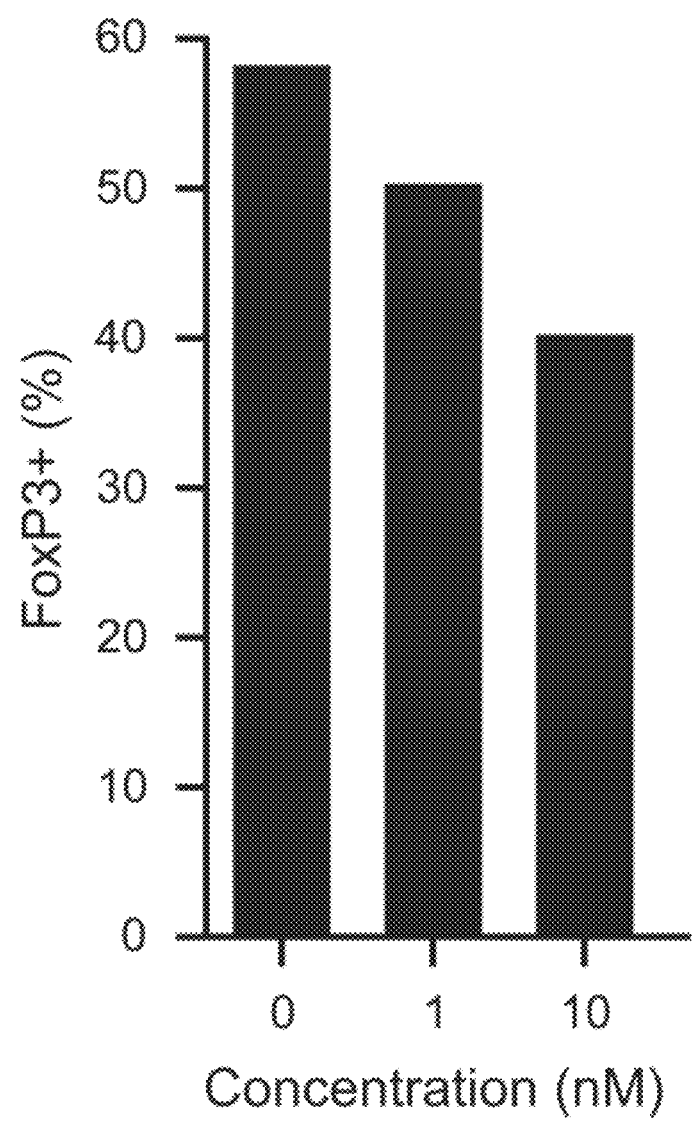
FIG. 22 depicts the effects of RAR signaling inhibition on RXR agonist inducement of Treg differentiation.

To determine whether a RXR agonist can mediate its effects via RAR/RXR receptor heterodimers, via RXR receptor homodimers, or via some other RXR containing complex, T cells were incubated with a RXR agonist in the presence of a pan-RAR antagonist and the expression of Foxp3 was assessed. Naive $CD4^+$ $CD25^-$ $FoxP3^-$ cells were purified from a Foxp3-GFP mouse using flow cytometry by sorting and isolating based upon a $GFP^-$ phenotype. These cells were then cultured under Treg cell differentiation conditions by treating the cells with αCD3 and αCD28 polyclonal antibodies in the presence of IL-2 and TGF-β. The cultured cells were incubated with RXR agonist IRX4204 (194204) at 1.0 nM together with 0 nM, 1 nM, or 10 nM of a pan-RAR antagonist 194310. The cultured cells were then assayed for the expression of Foxp3. The results indicate that the inclusion of a pan-RAR antagonist only partially blocked the induction of Foxp3 expression observed with an RXR agonist alone (FIG. 22). However, this partial inhibition of Fox3p expression may actually be due to the blocking of the effects of endogenous RA in the culture medium. As such, these results indicate that the observed conversion of T cells into Treg cells appears to occur through the use of RXR receptor homodimers and/or some other RXR containing complex, and not through a RAR-mediated mechanism.

Example 13

Effects of IRX4204 on Collagen-Induced Arthritis

Collagen-induced arthritis (CIA) is elicited in genetically susceptible strains of mice by immunization with type II collagen (CII) emulsified in complete Freund's adjuvant (CFA). The ensuing pathogenesis shares several pathological features with rheumatoid arthritis (RA), including synovial hyperplasia, mononuclear cell infiltration, cartilage degradation, and, like RA, susceptibility is linked to the expression of specific MHC class II genes.

Mice are injected intradermally in the tail with 50 µl type II collagen emulsified in Freund's complete adjuvant at a 1:1 ratio. An optional booster immunization can be used of CII emulsified in incomplete Freund's adjuvant (IFA) 14-21 days after the primary immunization. Animals exhibit signs of RA between 5 and 8 weeks after the primary immunization. Arthritis is scored according to the system in Table 4.

TABLE 4

Scoring system for subjective evaluation of arthritis severity.

| Severity score | Degree of inflammation |
|---|---|
| 0 | No evidence of erythema and swelling |
| 1 | Erythema and mild swelling confined to the tarsals or ankle joint |
| 2 | Erythema and mild swelling extending from the ankle to the tarsals |
| 3 | Erythema and moderate swelling extending from the ankle to metatarsal joints |
| 4 | Erythema and severe swelling encompass the ankle, foot and digits, or ankylosis of the limb |

Once evidence of arthritis is present, the mice are randomized into groups of four groups of five mice each; Group 1—vehicle control; Group 2—IRX4204 alone; Group 3—IRX4204 and thyroxine; and Group 4—positive control. The mice are dosed daily with the indicated drug and arthritis severity scored every other day.

Example 14

A Human Clinical Trial to Demonstrate Effects of IRX4204 in Parkinson's Disease

An open-label, single site clinical study of early Parkinson's Disease subjects treated with IRX4204 was conducted to determine whether the preclinical promise of IRX4204 as a disease modifying agent for PD will translate to the clinical setting upon treatment of early PD patients with IRX4204 as determined by Unified Parkinson's Disease Rating Scale (UPDRS) measurements and safety assessments. The changes in UPDRS scores were correlated with circulating thyroxine levels.

The objectives of this study were to further characterize the safety and tolerability of IRX4204 in early patients, particularly reduction in T4 levels, and to evaluate the effect of treatment with IRX4204 on the motor symptoms of PD measured by the UPDRS.

The study endpoints were (1) the change in motor testing scores from end of dosing period (Day 17), and (2) changes in T4 levels.

This was a single site, open-label study designed to examine efficacy (reduction in UPDRS scores) and safety of 3 dose levels of IRX4204 in cohorts of early PD patients for a period of approximately two weeks. In the three cohorts, each subject reported to the clinical research site on at least 3 occasions:

Screening (Visit 1)—Screening to determine eligibility (up to 30 days prior to Baseline Visit)

Baseline Period (Visit 2)—Treatment with IRX4204 began on Day 1.

Week 2 (Visit 3)—subjects returned to the clinic approximately 17 days after initiation of IRX4204 for safety and efficacy evaluations.

Safety and tolerability was assessed through all study visits including blood and urine samples for laboratory tests, ECGs, physical examination, neurological examination and assessments for adverse events.

To qualify for study participation, subjects were required to meet the following criteria: 40-80 years of age, inclusive; have a clinical diagnosis of PD based on the UK Brain Bank Criteria; participant has Hoehn and Yahr stage <3; participant may be treated with PD symptomatic therapy on a stable dose for at least 30 days prior to the Screening Visit. Dose levels of PD symptomatic therapies will remain stable through the study; must be willing and able to provide informed consent; females must be of either non-child bearing potential or must be willing to avoid pregnancy by using medically accepted contraception for 4 weeks prior to and 4 weeks following the last dose of study medication.

Subjects who met any of the following criteria were not included in the study: has any form of Parkinsonism other than idiopathic PD; are currently experiencing motor fluctuations (end of dose wearing off or dyskinesia) reflective of later stages of PD; has evidence of dementia or significant cognitive dysfunction; has clinically significant abnormal laboratory value and/or clinically significant unstable medical or psychiatric illness; the subject has any disorder that may interfere with drug absorption, distribution, metabolism or excretion; the subject has evidence of clinically significant gastrointestinal, cardiovascular, hepatic, pulmonary, or other disorder or disease; pregnancy or breastfeeding.

The clinical site prepared the study drug for administration by dispensing the correct dosage (20 mg/day, 10 mg/day or 5 mg/day) of IRX4204 for each subject. On Day 1, subjects received their first dose of IRX4204. After Day 1, IRX4204 drug dosing occurred at home daily. Patients took their daily dose of study medication with food approximately the same time each day, preferably between 8 AM and 10 AM. On Day 1, subjects received a 15-day supply of IRX4204 for a once daily dose of 20 mg, 10 mg, or 5 mg. Five subjects were recruited for each of the three dose levels. All fifteen subjects completed 15 days of dosing.

All subjects (n=52 total, n=12-13 per dose level) completed 15 days of dosing and returned to the clinic at the end of 2 weeks (day 15-17) for UPDRS score determination and safety assessments including determination of plasma thyroxine (T4) levels. Percent changes in Total Motor scores, Total UPDRS scores and plasma T4 values were determined according to the following:

$$\text{Percent Change} = \frac{\text{Baseline Value} - 2\text{ Week Value}}{\text{Baseline Value}} \times 100$$

The average percent changes in Total Motor and Total UPDRS scores for the three dose levels are given in Table 5. A negative score indicates an improvement in the disease as measured by the comprehensive UPDRS evaluation. The largest therapeutic response to IRX4204 treatment as measured by the Total Motor score (−31.4%) was obtained for the lowest dose of IRX4204 (5 mg/day). Surprisingly, there was less efficacy, as measured by the Total Motor sores, at each of the higher doses, 10 mg/day (11.7%) and 20 mg/day (−14.5%). Similar results were obtained when the Total UPDRS scores were considered. The best therapeutic response was obtained with the 5 mg/day cohort (−18.7%). Each of the higher doses, 10 mg/day and 20 mg/day, were progressively less efficacious with total UPDRS changes of −13.6% and 6.6%, respectively.

TABLE 5

| Dose | Total Motor Change | Total UPDRS Change |
|---|---|---|
| 20 mg/day | −14.5% | −6.6% |
| 10 mg/day | −11.7% | −13.6% |
| 5 mg/day | −31.4% | −18.7% |

The average percent changes in plasma T4 levels for the three cohorts are given in Table 6. The relationship between dose level and percentage reduction in plasma thyroxine (T4) was direct: the higher the dose of IRX4204 the greater the decrease in T4 levels. The 20 mg/day dose of IRX4204 leads to an almost complete abrogation of plasma T4 (98.8% reduction). Interestingly, this high dose of IRX4204 is associated with the least efficacy (only a 6.6% reduction in Total UPDRS scores).

TABLE 6

| Dose | Change in TSH |
|---|---|
| 20 mg/day | −98.8% |
| 10 mg/day | −36.6% |
| 5 mg/day | −28.9% |

These data in a human clinical trial clearly indicate that the reduction in thyroid hormone levels upon dosing with IRX4204 negatively impacts the therapeutic benefit of IRX4204. The clinical trial data from shows an inverse relationship between suppression of the thyroid axis (manifested by suppression of TSH, thyroid stimulating hormone) and clinical improvement from baseline in total motor scores and UPDRS.

Example 15

Effect of IRX4204 in Parkinson's Disease Model

The purpose of this study was to evaluate IRX4204 treatment for amelioration of behavioral deficits in the rat 6-OHDA induced Parkinson Disease (PD) model. The rat model of PD was produced by unilateral intra striatum injection of the neurotoxin 6-hydroxydopamine (6-OHDA). This injection produces dopaminergic (DA) neuron loss on the injected side while sparing the contralateral DA neurons. The study design is depicted in Table 7.

TABLE 7

| Group # | Group Size | Test Item | Route | Dose Level of Test Item (mg/kg) | Dose Volume of Test Item (ml/kg) | Dosing Regimen | Testing Regimen |
|---|---|---|---|---|---|---|---|
| 1 | n = 13 | Vehicle TA1 | PO | NA | 5 | Once daily from day 4 until the end of the study (day 24) | Paw Placement/ cylinder test: Day −1 (baseline), 3, 10, 17, and 24. |
|  |  | Vehicle TA2 | SC |  | 1 |  |  |
| 2 | n = 13 | TA1 | PO | 10 | 5 |  |  |
|  |  | Vehicle TA2 | SC | NA | 1 |  |  |
| 3 | n = 13 | Vehicle TA1 | PO | NA | 5 |  |  |
|  |  | TA2 | SC | T3: 1.5 µg/kg T4: 9 µg/kg | 1 |  |  |
| 4 | n = 12 | TA1 | PO | 10 | 5 |  |  |
|  |  | TA2 | SC | T3: 1.5 µg/kg T4: 9 µg/kg | 1 |  |  |

The paw placement (cylinder test) was used for assessment of the damage. This test assessed a rat's independent forelimb use to support the body against the walls of a cylindrical enclosure. The test took advantage of the animals' innate drive to explore a novel environment by standing on the hind limbs and leaning towards the enclosing walls.

To perform this test, rats were placed individually in a glass cylinder (21 cm diameter, 34 cm height) and wall exploration was recorded for 3 minutes. No habituation to the cylinder prior to recording was allowed.

The statistical analysis was performed as ratio between the intact and impaired legs (R/L ratio). The ratio was expressed as the values of intact right+both forelimbs divided by the values of impaired left+both forelimbs. A lower value of the ratio means greater healing of the 6-OHDA induced brain damage.

All treated animals gained weight throughout the study. The mean body weight of animals treated with the test item IRX4204 (TA1) with the vehicle of TA2 (group 2) or in combination with thyroxine and triiodothyronine (TA2; group 4) were significantly higher than the vehicle treated group (Group 1) on study days 17 and 24 (157.17±2.93% for Group 2 and 157.61±3.54% for Group 4 vs. 142.62±2.93% for the Vehicle group on day 24; $p<0.05$).

All animals with R/L ratio >1.5 were included in the study (ratio between the intact (R) and impaired legs (L) was expressed as the values of intact right+both forelimbs divided into the values of impaired left+both forelimbs).

Paw placement was measured prior to induction of lesion (baseline) and again 3 days after 6-OHDA injection, which was one day prior to IRX4204 treatment. Once a week during three weeks (study days 10, 17 and 24), the animals were re-tested for their performance in the paw placement test.

Animals were pre-selected based on the R/L ratio on study day 3, when the averaged ratio between the injured side and the intact side was increased relative to baseline levels (1.01±0.01 prior to surgery vs. 6.49±0.59, 3 days after surgery).

Figure 13:
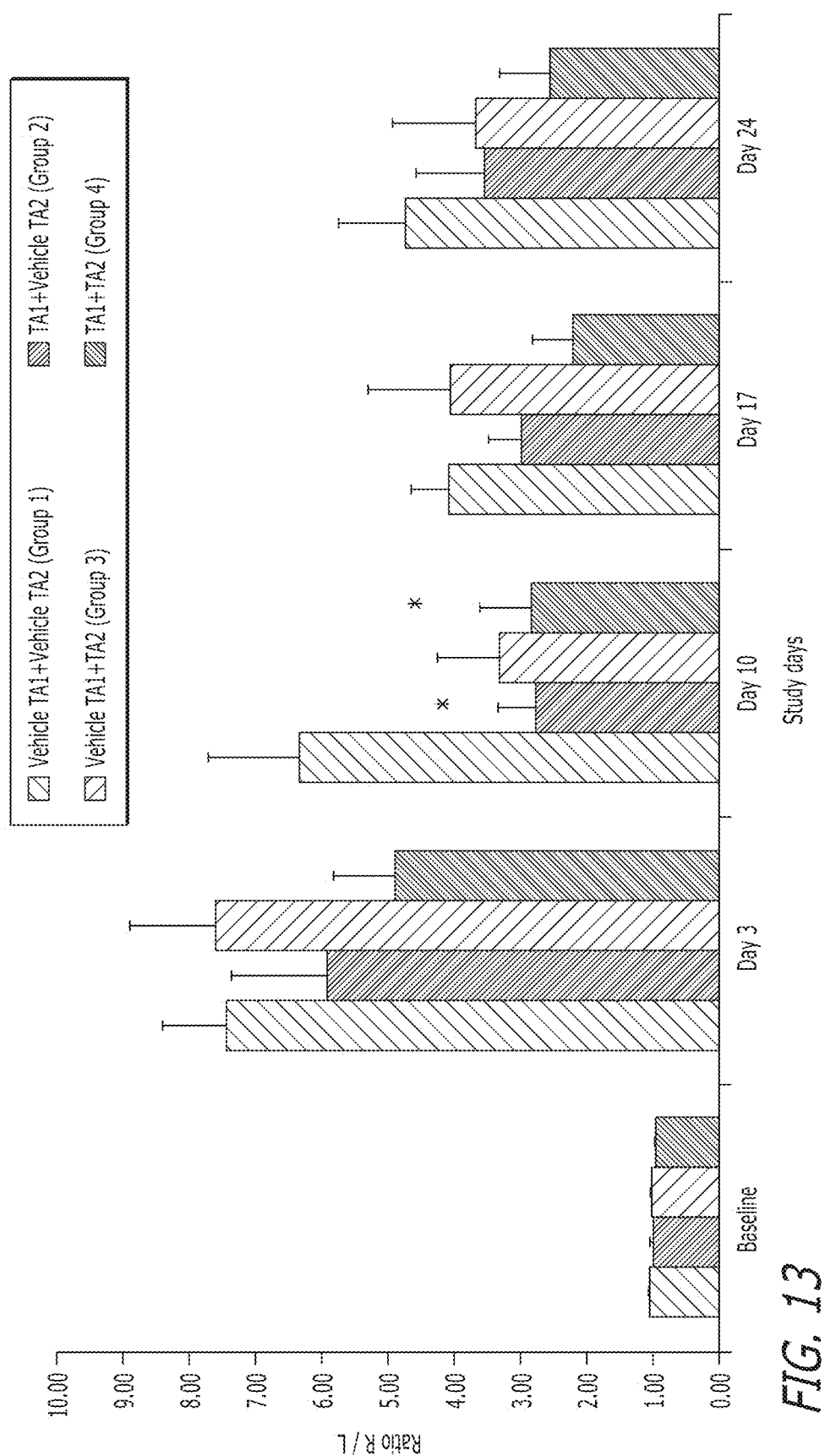
FIG. 13 depicts changes in paw placement behavior in a rat 6-OHDA-induced model of Parkinson's disease upon treatment with compounds and combinations described herein (*P<0.05 vs. vehicle using one way ANOVA followed by Dunnett test).
Figure 14:
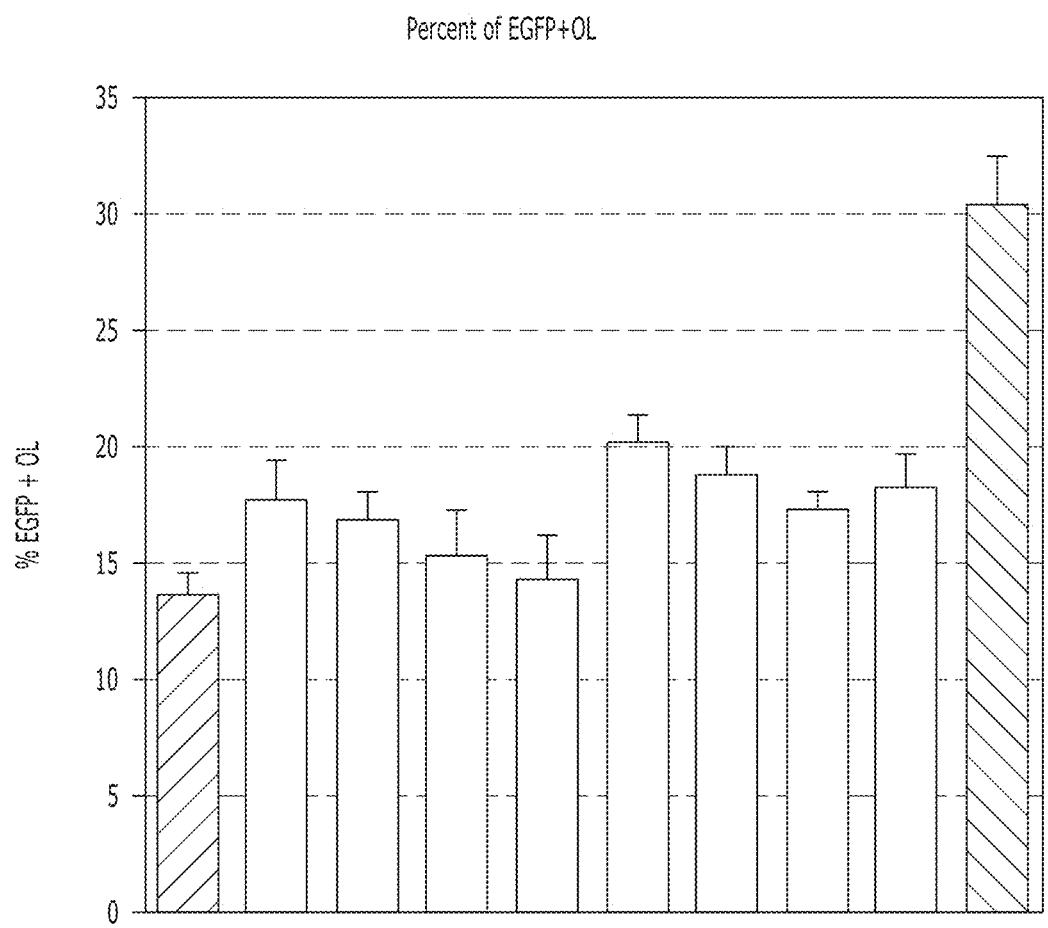
FIG. 14 depicts the percent and fold change of EGFP+ oligodendrocytes following treatment of oligodendrocytes with IRX4204, thyroid hormone, and Vitamin D (*: P<0.05, student's t-test against DMSO control; Error bar, SD).

As shown in FIG. 13, treatment with IRX4204 (TA1) with the vehicle of TA2 (group 2) or in combination with thyroxine and triiodothyronine (TA2; group 4) significantly reduced the mean calculated R/L ratio, compared to the vehicle treated group (group 1) on study day 10 (2.76±0.57 for Group 2 and 2.86±0.76 for Group 4 vs. 6.33±1.41 for the Vehicle group; $p<0.05$).

The mean calculated ratio was lower in these groups compared to the vehicle group also on study days 17 and 24, however this ratio was not statistically significant.

The average value of the ratio was calculated from the four values from days 3, 10, 17 and 24. The calculated values for group 2 and group 4 are 3.79 and 3.14, respectively. This indicates that group 4 (IRX4204 in combination with thyroxine and triiodothyronine) is more effective than group 2 (IRX4204) alone.

Example 16

Mouse Oligodendrocyte Progenitor Cell Differentiation in the Presence of Vitamin D The purpose of this study was to assess possible effects of IRX4204 in combination with vitamin D, or vitamin D and triiodothyronine (T3), on differentiation of mouse oligodendrocyte progenitor cells (OPCs) into oligodendrocytes. OPCs were derived from plp-EGFP expressing mice.

Therapeutic agents were tested in 96-well plates (6 wells per concentration). Negative and positive controls (DMSO or 10 ng/ml T3 thyroid hormone) were included in each plate. All media contained 0.1% DMSO and 0.1% EtOH. At the end of the 5-day treatment, cells were imaged on Cellomics in two channels and algorithms were used to count nuclei and EGFP+ oligodendrocytes.

Surprisingly, it was observed that different doses of vitamin D in combination with IRX4204 showed a negative effect in oligodendrocyte production (FIG. 10). The production of oligodendrocytes in response to a three regimen treatment (IRX4204, Vitamin D and T3) was slightly higher than that of the treatment without T3 (IRX4204 and Vitamin D). This suggests an additive effect of T3 in the three regimen combination.

Example 17

Mouse Oligodendrocyte Progenitor Cell Differentiation

The purpose of this study was to assess possible effects of IRX4204 in combination with triiodothyronine (T3), on differentiation of mouse oligodendrocyte progenitor cells (OPCs) into oligodendrocytes. OPCs were derived from plp-EGFP expressing mice.

Therapeutic agents were tested in 96-well plates (6 wells per concentration). Negative and positive controls (DMSO or 10 ng/ml T3 thyroid hormone) were included in each plate. All media contained 0.1% DMSO. At the end of the 5-day treatment, cells were imaged on Cellomics in two channels and algorithms were used to count nuclei and EGFP+ oligodendrocytes.

Figure 15A:
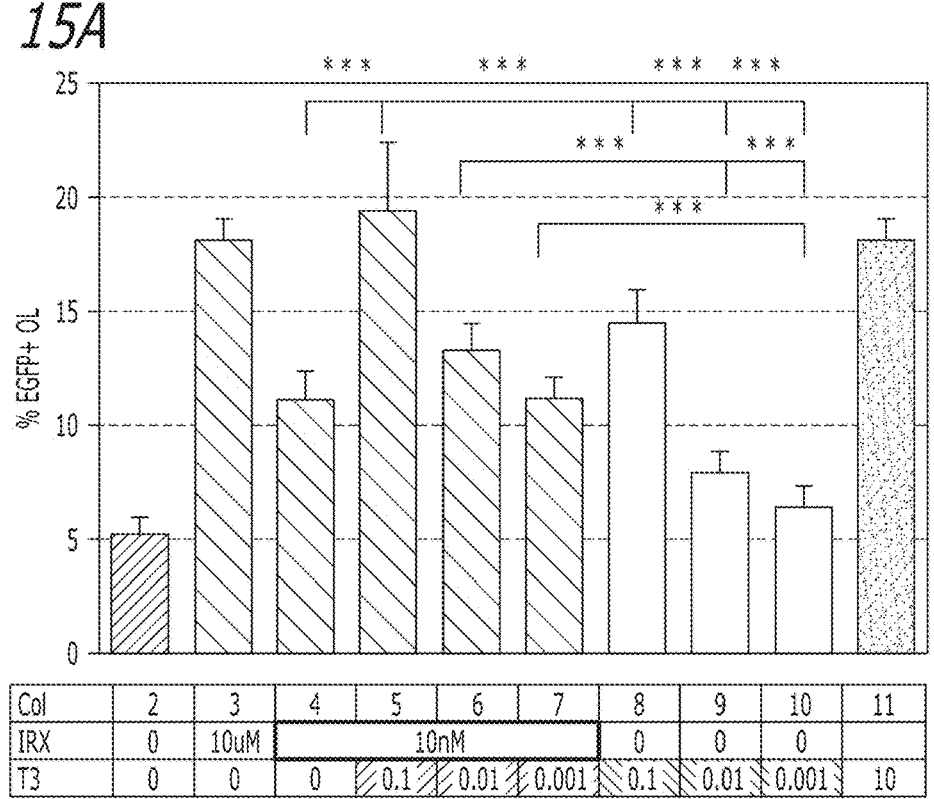
FIGS. 15A-C depicts the percent change of EGFP+ oligodendrocytes following treatment of oligodendrocytes with IRX4204 and thyroid hormone (FIG. 15A: 10 nM IRX4204.
Figure 15B:
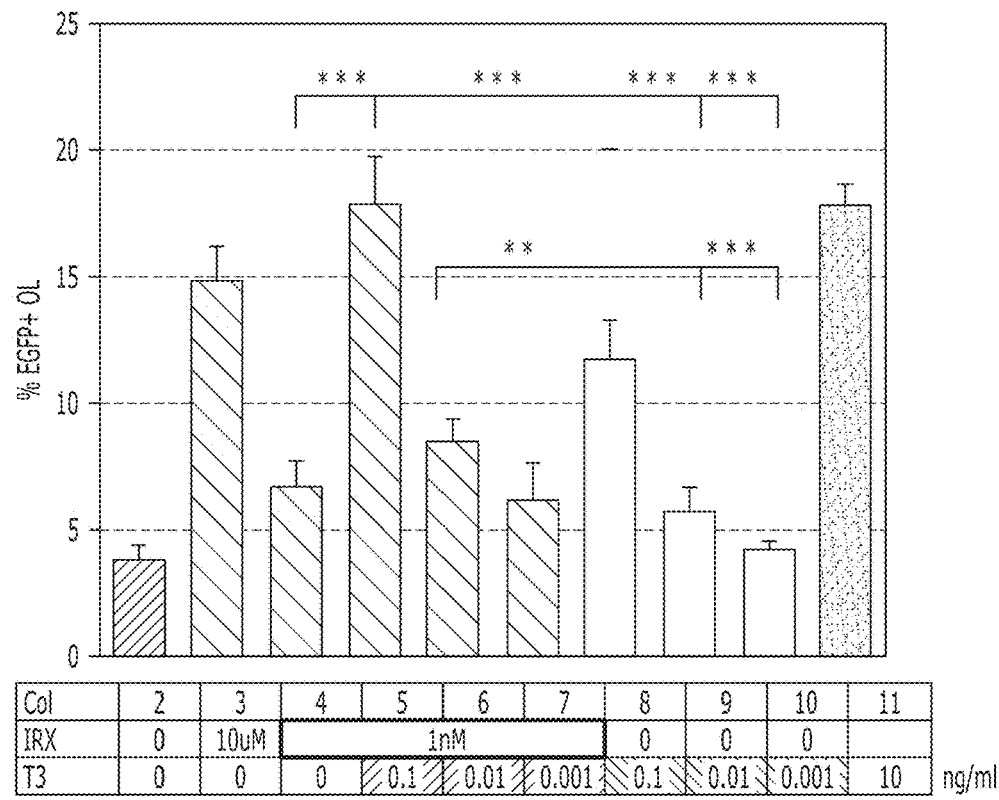
Figure 15C:
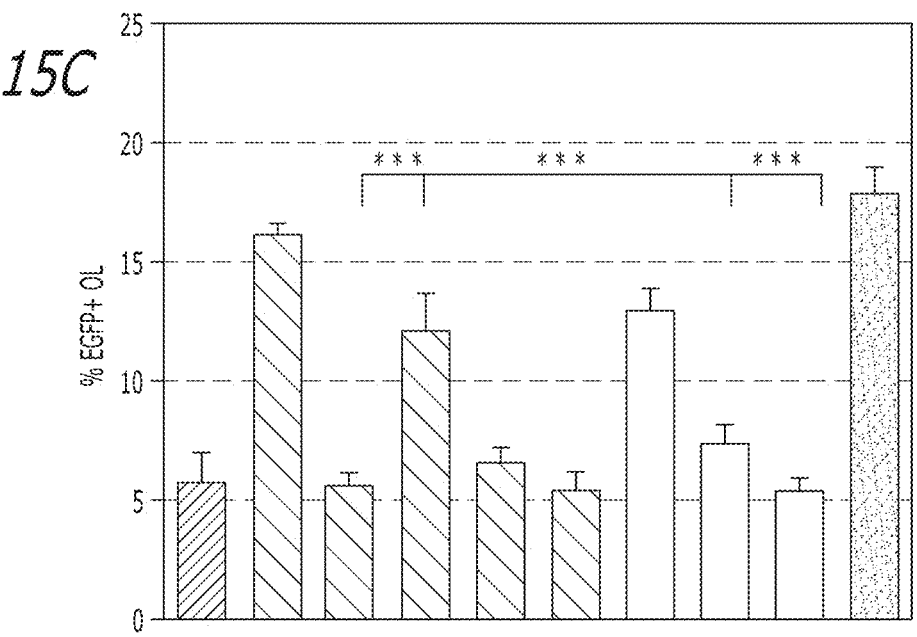

FIG. 15A-C show clear dose-responses in oligodendrocyte production in response to different doses of IRX4204 and T3. The production of oligodendrocytes in response to combination treatments of IRX4204 and T3 was more than that of individual treatment alone in all conditions. This suggests an additive, or potentially a synergistic, effect in driving oligodendrocyte precursor cell differentiation between IRX4204 and T3. Similar results were obtained when cells were stained with MBP antibody and quantified (data not shown). These data suggest that a combination of IRX4204 and T3 (or T4) will be optimal in remyelination.

Example 18

Neuroprotective Effect of IRX4204 in a Mouse Model of Demyelination

The goal of this study was to evaluate the neuroprotective effect of IRX4204 in a mouse model of non-immune mediated demyelination.

In this study, the 6-week demyelination model was used to assess neuroprotective potential of IRX4204 following 6-week concurrent treatment during demyelination. A subgroup of animals were treated with T4 along with IRX4204. The results from this study demonstrate that IRX4204 promotes neuroprotection without reducing the extent of demyelination in the corpus callosum.

Animals (8 week-old male C57BL/6J mice) were subjected to cuprizone diet plus rapamycin injections (CR) for 6 weeks to induce demyelination. Animals were treated with either vehicle or IRX4204 (10 mg/kg, PO), or IRX4204+T4 (10 mg/kg, PO, and 20 ng/g, SQ) daily for the entire 6 weeks during demyelination. All animals were sacrificed after 6 weeks of CR to evaluate axonal integrity and microglial/macrophage activity in the white matter (corpus callosum, CC). Two groups (Vehicle and IRX4204+T4) were further examined for any protective effects on the extent of myelination in the CC.

There was a significant reduction in axonal transection as shown by the decrease in the number of SMI32 positive axonal ovoids in the animals treated with IRX4204+T4. However, there was no difference in microglial/macrophage activation and the number of myelinated axons in the CC between the Vehicle and IRX4204+T4 groups. These findings support a neuroprotective role of IRX4204 mediated by a potential direct effect on demyelinated axons.

A total of 50 animals were included in the study, where 43 animals received CR demyelination for 6 weeks. During demyelination, a subset (n=7) of animals were kept on normal diet to serve as naïve age-matched controls. The remaining animals received IRX4204 (n=14) or vehicle (n=14) or IRX4204+T4 (n=15) for 6 weeks concurrently during CR. There was no mortality during the in-life phase. In addition, there were no observed health concerns during the treatment phase. All animals were alert and demonstrated proper grooming behavior. ANOVA analysis with multiple group comparison showed no significant difference in terminal body weights between IRX4204 or vehicle groups.

To assess thyroid hormone levels, terminal blood draws were taken to quantify the levels of T4. Animals treated with IRX4204 alone showed an approximate 50% decrease in T4 levels when compared to vehicle control animals. Exogenous treatment with T4 corrected the thyroid hormone levels as shown by increase in T4 levels in IRX4204+T4 group.

The floating brain sections were immunostained with SMI-32 to visualize and quantify axonal ovoids in the CC. Animals that were subjected to CR showed significantly higher numbers of SM132 stained axonal ovoids in CC compared to naïve animals. There was a significant decrease in the number of axonal ovoids in animals treated with both IRX4204 and T4 compared to Vehicle. IRX4204 alone showed a trend towards decreased number of axonal ovoids but was not statistically different from the Vehicle.

The floating brain sections were immunostained with Iba-1 to visualize and quantify microglia/macrophages in CC. Animals subjected to CR and treated with Vehicle had a robust increase in Iba1 staining in CC compared to naïve animals. There was no difference in the levels of Iba1 staining in IRX4204 or IRX4204+T4 treated animals compared to vehicle.

Semi-thin (1 μm) sections of Epon-embedded CC tissue from animals that received CR and Vehicle or IRX4204+T4 were used to visualize and quantify the number and density of myelinated axons in the CC. Animals that received CR and vehicle demonstrated robust demyelination of the CC. There was no significant difference in the number and density of myelinated axons in IRX4204+T4 treated animals when compared to vehicle.

IRX4204 treatment alone without T4 showed a trend towards decrease in axonal ovoids, but it was statistically not different from vehicle. However, when animals that received IRX4204 were supplemented with exogenous T4 there was a significant decrease in the number of axonal ovoids compared to vehicle. This data along with our previous in vivo findings support a neuroprotective effect of IRX4204. While there was a decrease in axonal ovoids, there was no significant difference in microglial/macrophage activation and myelination in the corpus callosum in Vehicle and IRX4204+T4 groups.

The finding that IRX4204 demonstrated a neuroprotective effect only in the group with supplemental T4 suggests an enhanced effect of the combination therapy over IRX4204 alone.

Figure 20A:
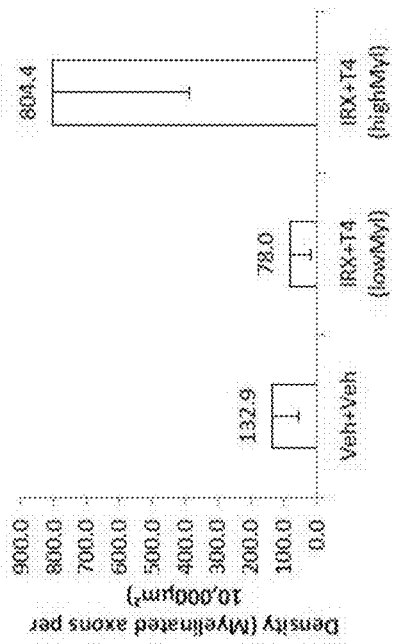
FIGS. 20A-C depicts a quantification of myelination of the corpus callosum following in vivo treatment with combinations described herein, and a separation of the data into potential responders and non-responders (one way ANOVA with Tukey's multiple comparisons, *P<0.05 P<0.01, **P<0.001).
Figure 20B:
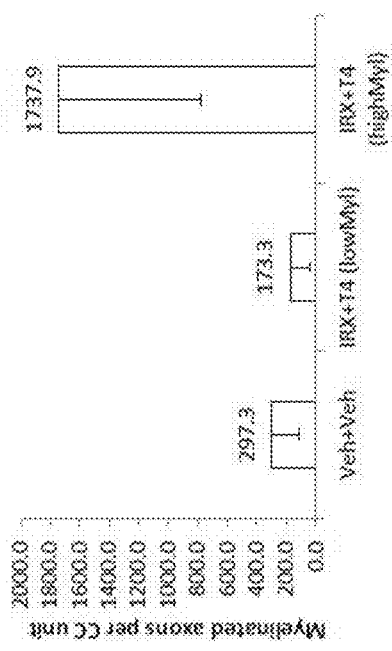
Figure 20C:
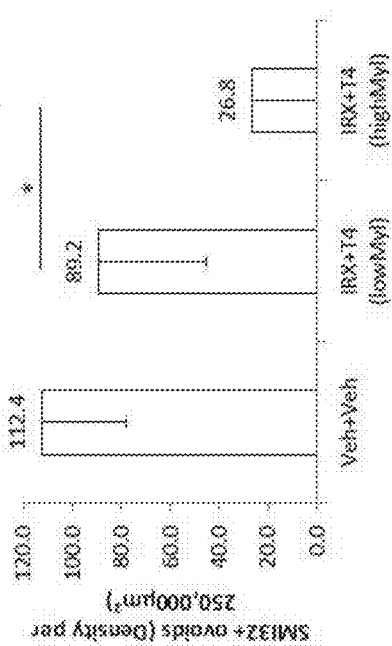

Quantification of myelinated axons in the corpus callosum shows potential responders and non-responders. FIG. 20A-C shows a high correlation between the number of axonal ovoids and myelinated axons (i.e. the animals that had very few ovoids had very high number and density of myelinated axons in the corpus callosum).

Example 19

A Human Clinical Trial to Ascertain Effects of the Combination of IRX4204 and Thyroxine on Rheumatoid Arthritis A proof of concept clinical trial of the combination of IRX4204 and thyroxine is conducted in rheumatoid arthritis (RA) patients to ascertain the direct effects of the combination in such a patient group. Patients with RA are recruited to participate in the clinical trial and are provided informed consent describing risks and potential benefits of participation. The RA patients are treated with one of several dose levels of IRX4204, ranging from 1 mg/day to 40 mg/day, administered orally as capsules, once per day and thyroxine, administered at 12.5 μg/day to 250 μg/day orally. Some patients are randomized to receive a placebo dose using matching capsules, which do not contain IRX4204 or thyroxine, or IRX4204 alone. Patients are dosed for a minimum of 30 days, and as long as 2 years. The patients' serum thyroid hormone levels are tested periodically and the thyroxine dose adjusted as necessary. Patients are assessed for RA disease activity through the DAS clinical index. Dose response relationships of the IRX4204/thyroxine combination to RA diagnostic criteria and DAS scores are analyzed across the cohorts of patients treated with various dose levels of IRX4204 and thyroxine for patient reaction and any affect on RA disease activity.

Example 20

A Human Clinical Trial to Evaluate the Effects of a Combination of IRX4204 and Thyroxine Treatment on Progression of Psoriasis A proof of concept clinical trial of the combination of IRX4204 and thyroxine is conducted in psoriasis patients to ascertain the direct effects of the combination in such a patient group. Patients with psoriasis are recruited to participate in the clinical trial and are provided informed consent describing risks and potential benefits of participation. The psoriasis patients are treated with one of several dose levels of IRX4204, ranging from 1 mg/day to 40 mg/day, administered orally as capsules, once per day and thyroxine, administered at 12.5 μg/day to 250 μg/day orally. Some patients are randomized to receive a placebo dose using matching capsules, which do not contain IRX4204 or thyroxine, or to capsules containing IRX4204 alone. Patients are dosed for a minimum of 30 days, and as long as 2 years. The patients' serum thyroid hormone levels are tested periodically and the thyroxine dose adjusted as necessary. Throughout the clinical trail, patients are assessed for psoriasis activity through physical examination by a dermatologist or a like medical professional and monitoring of psoriatic episodes. Dose response relationships of the IRX4204/thyroxine combination are analyzed across the cohorts of patients treated with various dose levels of IRX4204 and thyroxine for patient reaction and any affect on psoriasis activity.

Example 21

A Human Clinical Trial to Evaluate the Effects of a Combination of IRX4204 and Thyroxine Treatment on Progression of IBD A proof of concept clinical trial of the combination of IRX4204 and thyroxine is conducted in patients with Crohn's disease, in patients to ascertain the direct effects of the combination in such a patient group. Patients with Crohn's disease are recruited to participate in the clinical trial and are provided informed consent describing risks and potential benefits of participation. The Crohn's disease patients are treated with one of several dose levels of IRX4204, ranging from 1 mg/day to 40 mg/day, administered orally as capsules, once per day and thyroxine, administered at 12.5 μg/day to 250 μg/day orally. Some patients are randomized to receive a placebo dose using matching capsules, which do not contain IRX4204 or thyroxine. Patients are dosed for a minimum of 30 days, and as long as 2 years. The patients' serum thyroid hormone levels are tested periodically and the thyroxine dose adjusted as necessary. Throughout the clinical trail, patients are assessed for Crohn's disease activity through laboratory tests, such as, but not limited to complete blood cell tests, electrolyte panel, liver function tests, and fecal occult blood tests. Dose response relationships of the IRX4204/thyroxine combination are analyzed across the cohorts of patients treated with various dose levels of IRX4204 and thyroxine for patient reaction and any affect on Crohn's disease activity.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating an autoimmune skin disorder, the method comprising administering to an individual in need thereof a therapeutically effective amount of a RXR agonist and a thyroid hormone, wherein the RXR agonist has the structure of Formula II

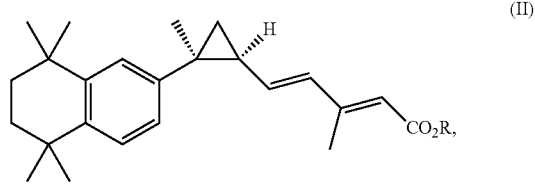

wherein R is H; or a pharmaceutically acceptable salt thereof;

wherein administration of the RXR agonist and the thyroid hormone treats the autoimmune skin disorder in the individual more effectively than either the RXR agonist or the thyroid hormone alone.

2. The method according to claim 1, wherein the RXR agonist is 3,7-dimethyl-6(S),7(S)-methano,7-[1,1,4,4-tetramethyl-1,2,3,4-tetrahydronaphth-7-yl]2(E),4(E) heptadienoic ethyl ester.

3. The method according to claim 1, wherein the thyroid hormone is thyroxine.

4. The method according to claim 1, wherein the therapeutically effective amount of the RXR agonist is about 0.001 mg/day to about 1000 mg/day.

5. The method according to claim 1, wherein the therapeutically effective amount of the RXR agonist is about 1 mg/day to about 100 mg/day.

6. The method according to claim 3, wherein the therapeutically effective amount of the thyroxine is about 12.5 µg/day to about 250 µg/day.

7. The method according to claim 1, wherein the RXR agonist is administered orally.

8. The method according to claim 1, wherein the RXR agonist is administered topically.

9. The method according to claim 3, wherein the RXR agonist and the thyroxine are both administered substantially simultaneously.

10. The method according to claim 3, wherein the RXR agonist and the thyroxine are administered on different schedules.

11. The method according to claim 3, wherein the thyroxine is administered orally.

12. The method according to claim 3, wherein the thyroxine is administered subcutaneously.

13. The method according to claim 3, wherein the RXR agonist and the thyroxine are administered topically.

14. The method according to claim 1, wherein the autoimmune skin disorder is dermatitis, eczema, bullous pemphigoid, pemphigus vulgaris, morphea, statis dermatitis, hidradenitis suppurativa, psoriasis, rosacea, scleroderma, discoid lupus erythematosus, subacute cutaneous lupus erythematosus, or vitiligo.

15. The method according to claim 14, wherein the autoimmune skin disorder is psoriasis.

16. A method of treating an autoimmune skin disorder, the method comprising administering to an individual in need thereof a therapeutically effective amount of 3,7-dimethyl-6(S),7(S)-methano,7-[1,1,4,4-tetramethyl-1,2,3,4-tetrahydronaphth-7-yl]2(E),4(E) heptadienoic acid (IRX4204) and thyroxine; and wherein administration of the IRX4204 and the thyroxine reduces severity of the autoimmune skin disorder in the individual more effectively than either the IRX4204 or the thyroxine alone.

17. The method according to claim 1, wherein treatment of the autoimmune skin disorder alleviates hair loss.

* * * * *